US006869929B2

(12) United States Patent
Oettgen et al.

(10) Patent No.: US 6,869,929 B2
(45) Date of Patent: Mar. 22, 2005

(54) USE OF TRANSCRIPTION FACTORS FOR TREATING INFLAMMATION AND OTHER DISEASES

(75) Inventors: Peter Oettgen, Brookline, MA (US); Towia Libermann, Newton, MA (US); Mary Goldring, Auburndale, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 10/393,905

(22) Filed: Mar. 20, 2003

(65) Prior Publication Data

US 2003/0229003 A1 Dec. 11, 2003

Related U.S. Application Data

(63) Continuation-in-part of application No. PCT/US01/29340, filed on Sep. 20, 2001.
(60) Provisional application No. 60/234,379, filed on Sep. 20, 2000.

(51) Int. Cl.[7] .............................................. C07K 14/00
(52) U.S. Cl. ........................................... 514/2; 530/350
(58) Field of Search ................................ 514/2; 530/350

(56) References Cited

U.S. PATENT DOCUMENTS 6,024,940 A 2/2000 Ghio et al. .................... 424/45

OTHER PUBLICATIONS

Rudders et al., "ESE–1 Is a Novel Transcriptional Mediator of Inflammation That Interacts with NF–κB to Regulate the Inducible Nitric–oxide Synthase Gene", The Journal of Biological Chemistry, 276(5):3302–3309 (2001).

Primary Examiner—Karen Cochrane Carlson
(74) Attorney, Agent, or Firm—David G. Conlin; Jennifer K. Rosenfield; Edwards & Angell, LLP

(57) ABSTRACT

The present invention provides a method of treating inflammation in a mammal comprising altering the activity of a transcription factor involved in the inflammatory response. The invention also relates to the use of transcription factors to screen compounds that are capable of reducing inflammation. The invention also relates to the use of transcription factors in methods of diagnosing the presence of an inflammatory disease in a tissue of a mammal and methods of monitoring the treatment of an inflammatory disease in a tissue of a mammal.

11 Claims, 35 Drawing Sheets

FIG. 1
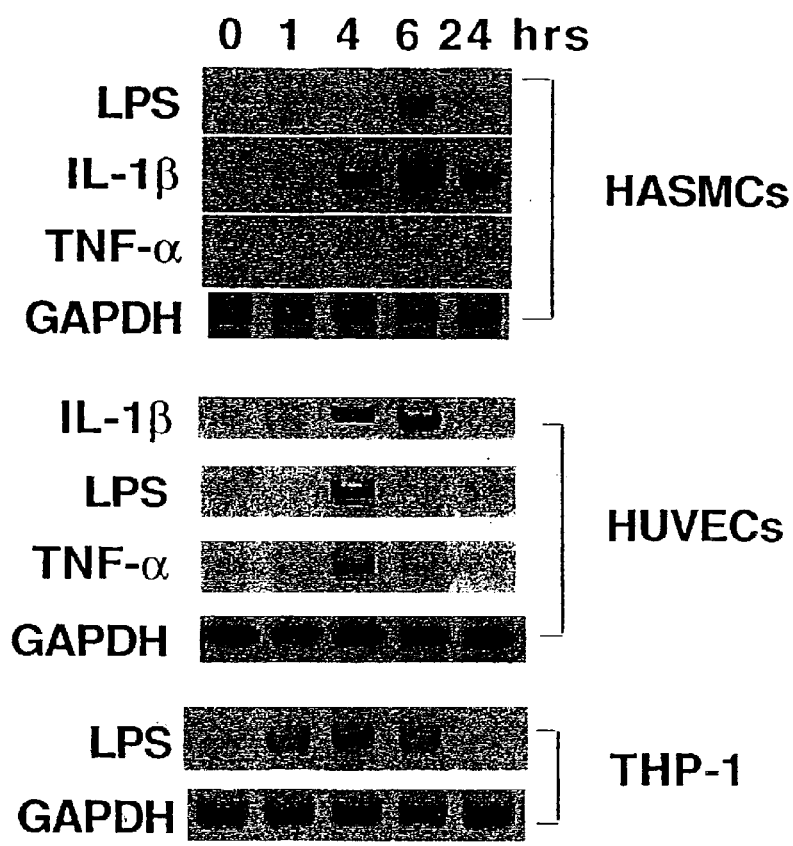
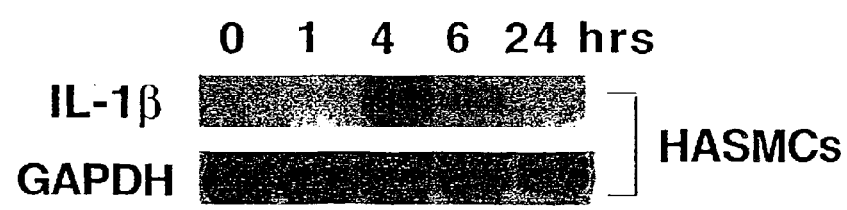

FIG. 2  ESE-1 Promoter
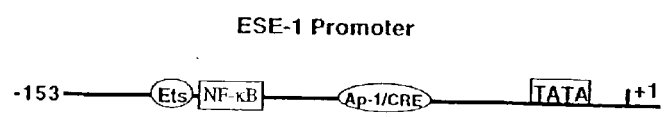
FIG. 3A
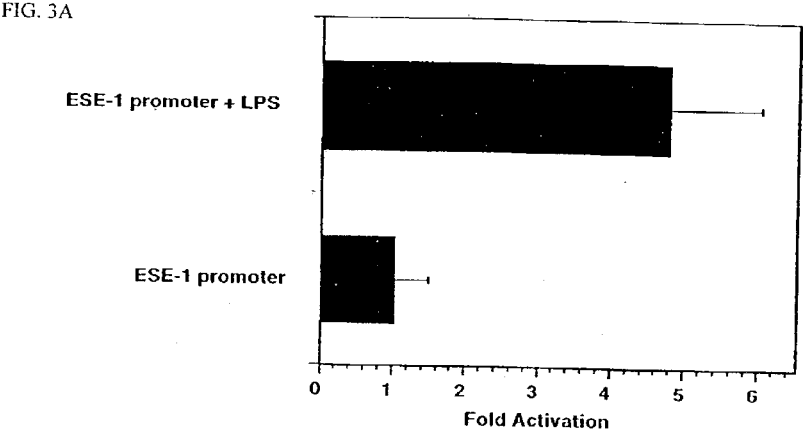
FIG. 3B
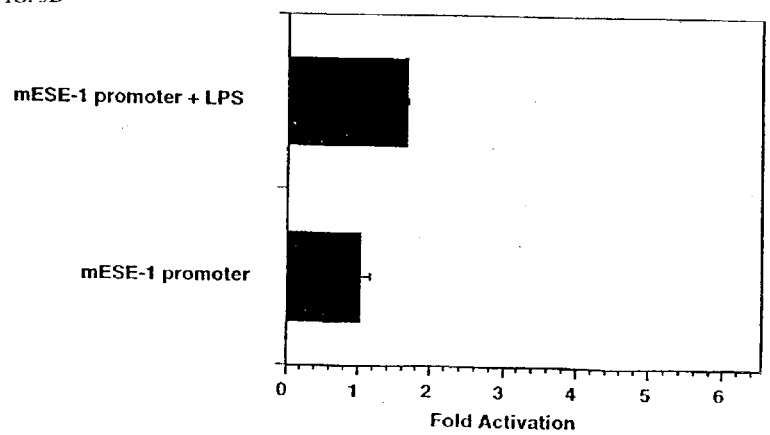

FIG. 5
A
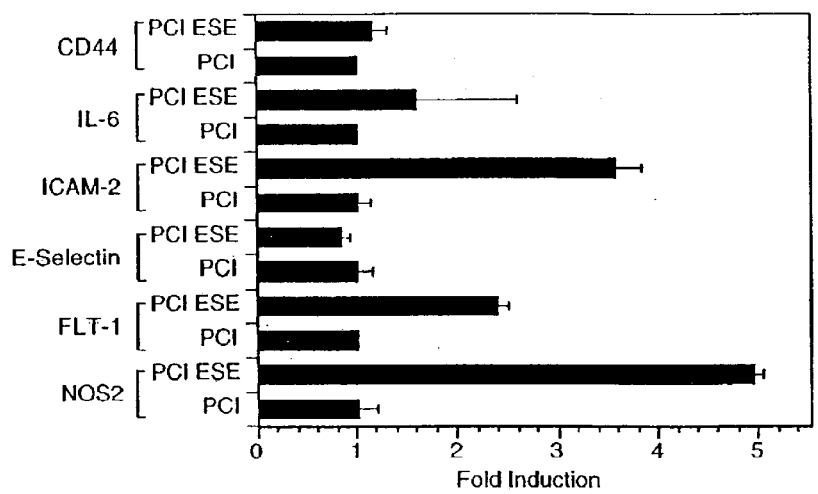
B
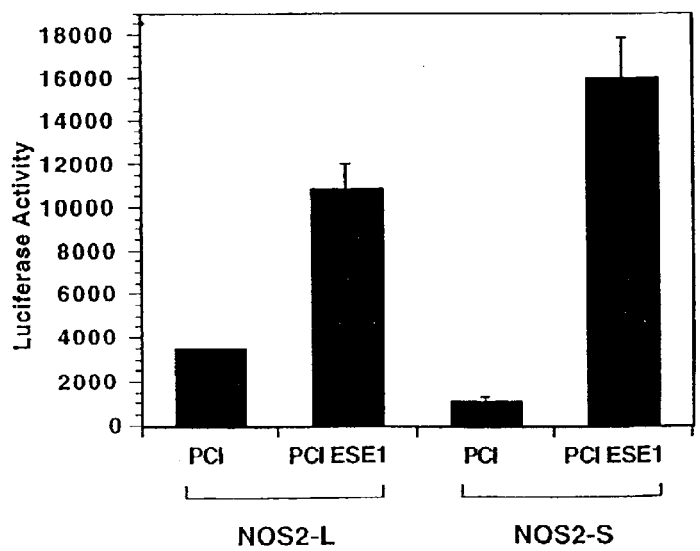

FIG. 7
A
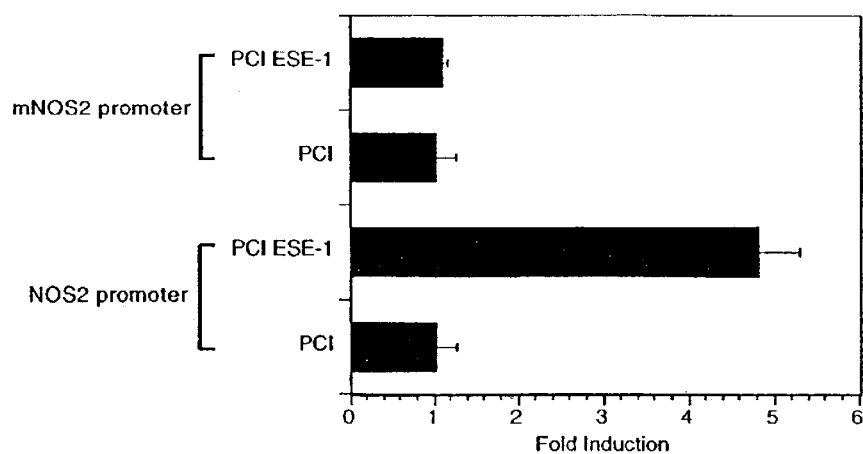
B
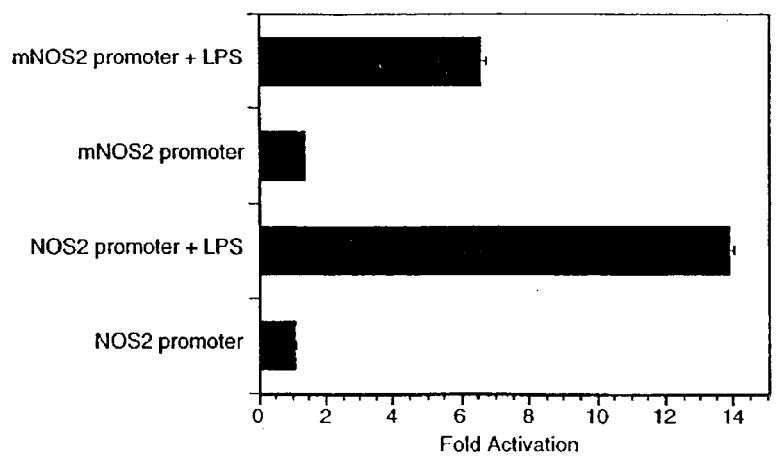

FIG. 8
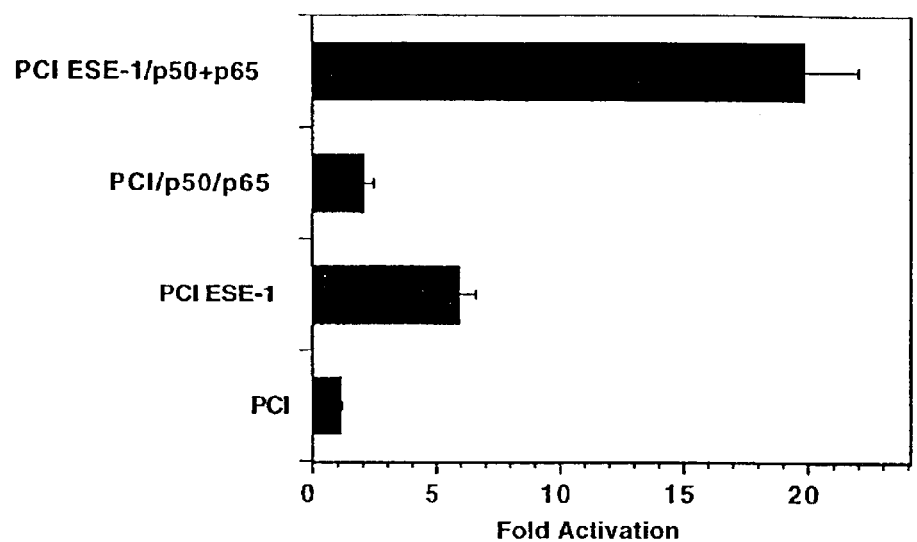
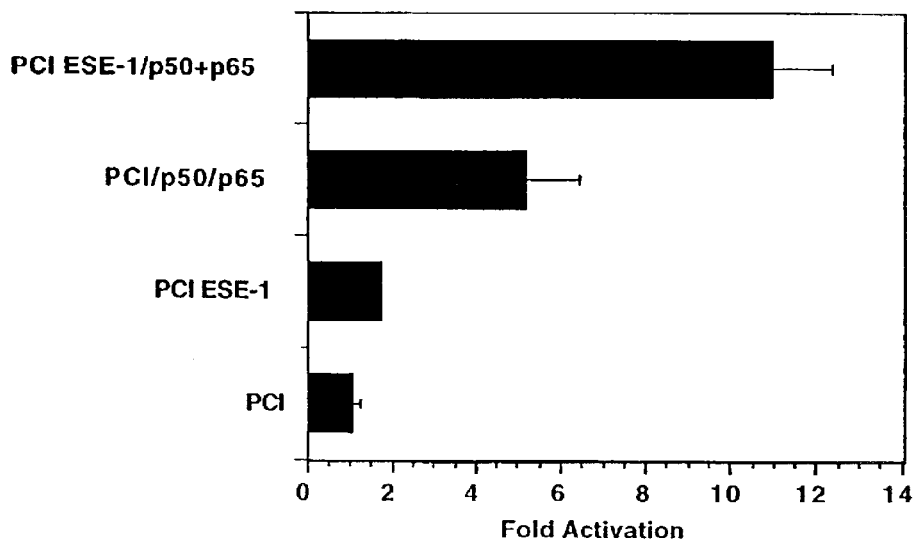

FIG. 9
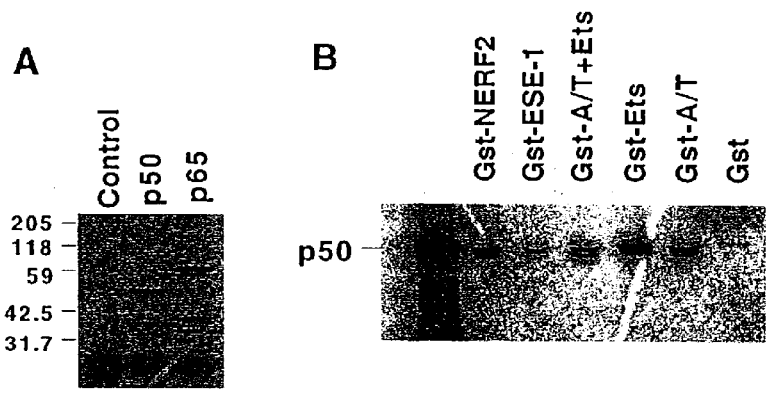
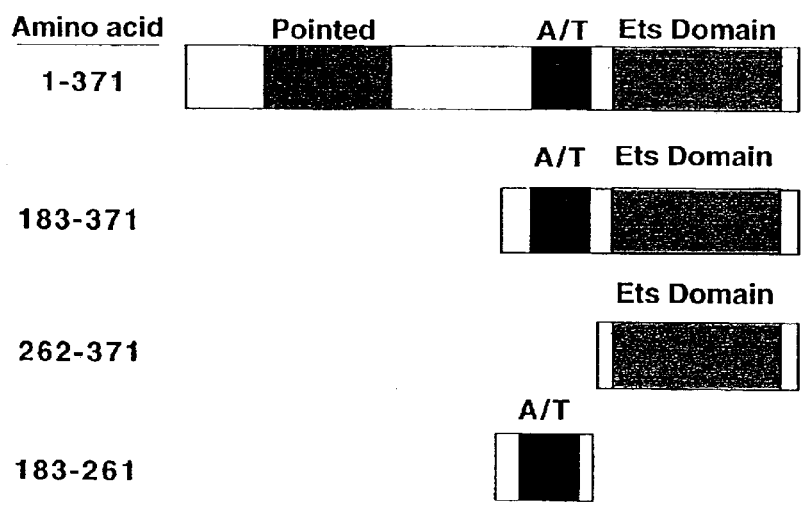

FIG. 10
Control
ESE-1
NOS2

FIG. 13

```
              ETS #5                                    AP-2            C/EBP
b)  -170  TCTC ATTTCCGT GGGTAAAAAACCCT GGCCCCACCGGC TTACGCA
                                      ETS #4/NFAT
    -124  AATTTTTTAAGGGGAGAG GAGCCAAAAAT TTGTGGGGGTACGAAA
           ETS #3 NFAT    AP-1         CRE     E-box
    -78   AC GCGGTAAGAAA CAGTCA T TTGGT CACATG GGCTTGGTTTTCAGT
             TATA    ETS #2                       +1
    -32   CT TATAAAA AGGAAGG TTCTCTCGTTAGCGAC CAATTGTCATACGA
                                                   ETS #1
    +14   CTTGCAGTGAGCGTCAGGAGCACCTC CAGGAACT CCTCAGCAGCGC

+60   CTCCTTCAGCTCCACAGCCAGACGCCCTCAGACAGCAAAGCCTACC

+106  CCCGCGCCGCGCCCTGCCCGCCGCTGCGATGCTC
```

A
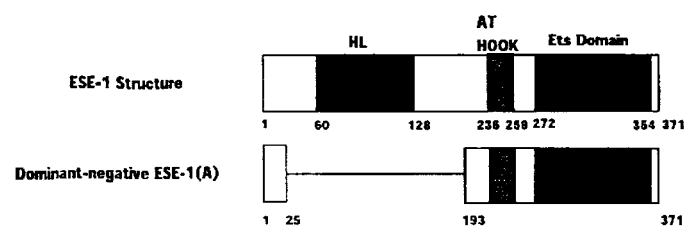
B
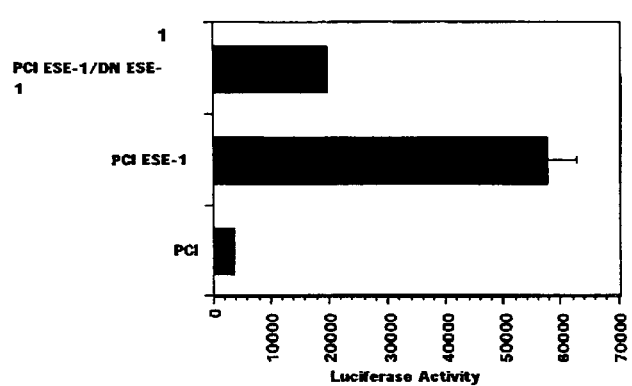
C
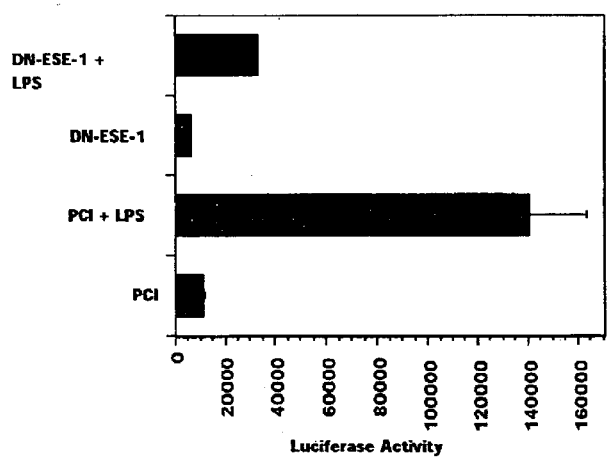
Figure 21

AMINO ACID SEQUENCE OF ESE-1 DN1 maatceisni fsnyfsamys sedstag tgasrsshss dsggsdvdld ptdgklfpsd gfrdckkgdp khgkrkrgrp rklskeywdc legkkskhap rgthlwefir dilihpelne glmkwenrhe gvfkflrsea vaqlwgqkkk nsnmtyekls ramryyykre ilervdgrrl vykfgknssg wkeeevlqsr n

FIGURE 22A

AMINO ACID SEQUENCE OF ESE-1 DN2 aatceisni fsnyfsamys sedstlasvp paatfgaddl vltlsnpqms legtekaswl geqpqfwskt qvldwisyqv eknkydasai dfsrcdmdga tlcncaleel rlvfgplgdq lhaqlrdlts sssdelswii ellekdgmaf qealdpgpfd qgspfaqell ddgqqaspyh pgscgagaps pgssdvstag tgasrsshss dsggsdvdld ptdgklfpsd g

SEQUENCE LISTING

<160> NUMBER OF SEQ ID NOS: 40

<210> SEQ ID NO 1
<211> LENGTH: 17
<212> TYPE: PRT
<213> ORGANISM: Unknown Organism
<220> FEATURE:
<223> OTHER INFORMATION: Description of Unknown Organism: Illustrative
      membrane permeable sequence

<400> SEQUENCE: 1

Ala Ala Val Ala Leu Leu Pro Ala Val Leu Leu Ala Leu Leu Ala Lys
 1               5                   10                  15

Ser

<210> SEQ ID NO 2
<211> LENGTH: 17
<212> TYPE: PRT
<213> ORGANISM: Unknown Organism
<220> FEATURE:
<223> OTHER INFORMATION: Description of Unknown Organism: Illustrative
       membrane permeable sequence

<400> SEQUENCE: 2

Val Thr Val Leu Ala Leu Gly Ala Leu Ala Gly Val Gly Val Gly Lys
 1               5                  10                  15

Ser

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
ctgagcaaag agtactggga ctgtc                                          25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
ccatagttgg gccacagcct cggagc                                         26

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
caaagttgtc atggatgacc                                                20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
ccatggagaa ggctgggg                                                  18

<210> SEQ ID NO 7
<211> LENGTH: 27
<212> TYPE: DNA
<213> ORGANISM: Mus sp.

<400> SEQUENCE: 7
tcgacgaaca tccaggaaat agggctc                                        27

<210> SEQ ID NO 8
<211> LENGTH: 27

```
<212> TYPE: DNA
<213> ORGANISM: Mus sp.

<400> SEQUENCE: 8
tcgagagccc tatttcctgg atgttcg                                        27

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
aggccaggaa atcccctcca tc                                             22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
aggccaggaa atcggatcca tc                                             22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcgacatgtg ggattttccc atgac                                          25

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gcacgtccag gaactcctca gc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gagagaacct tccttttat aa                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued

```
probe

<400> SEQUENCE: 14
cgaaaaggcg aaagaaaca gt                                          22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gagaggaggg aaaaatttgt gg                                         22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tctcatttcc gtgggtaaaa a                                          21

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 17
ctaaaggcca ggaaatcgga tccatccaat gagacac                         37

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
gctgaggagt agctggacgt gctcctgac                                  29

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 19
cagtcttata aaaccaagg ttctctcggt tagcgacc                         38

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 20
gacgaaatga ctgtttctttt gagccttttc gtacccc                        37
```

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 21
gggtttttta cccacgctaa tgagaaaatc ggaaacc                    37

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22
ctgagcaaag agtactggga ctgtc                                 25

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
ccatagttgg gccacagcct cggagc                                26

<210> SEQ ID NO 24
<211> LENGTH: 11
<212> TYPE: DNA
<213> ORGANISM: Homo sapiens

<400> SEQUENCE: 24
aggaaatccc c                                                11

<210> SEQ ID NO 25
<211> LENGTH: 11
<212> TYPE: DNA
<213> ORGANISM: Homo sapiens

<400> SEQUENCE: 25
aggaaatcgg a                                                11

<210> SEQ ID NO 26
<211> LENGTH: 310
<212> TYPE: DNA
<213> ORGANISM: Homo sapiens

<400> SEQUENCE: 26
tctcatttcc gtgggtaaaa aaccctgccc ccaccgggct tacgcaattt ttttaagggg      60
agaggaggga aaaatttgtg ggggtacga aaaggcggaa agaaacagtc atttcgtcac      120
atgggcttgg ttttcagtct tataaaaagg aaggttctct cgttagcgac caattgtcat      180
acgacttgca gtgagcgtca ggagcacgtc caggaactcc tcagcagcgc ctccttcagc      240
tccacagcca gacgccctca gacagcaaag cctaccccg cgccgcgccc tgcccgccgc      300
tgcgatgctc                                                            310

<210> SEQ ID NO 27

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgcctgcagg gaagggctaa                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tctaccgctt tccctcctcc                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccatgtcttt tccgtccttg                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
actccggcag aactccgagg                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcacgccctt cccgcctgtg                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagggcggg aagcgtgact                                                 20

<210> SEQ ID NO 33
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcatgctgca gaaaagggct aaaa                                            24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cttctaccgc tttttctcct ccct                                            24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccatgtcttt tttgtccttg                                                 20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
caactccggc ttaactccga gggg                                            24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cggcacgccc ttttcgcctg tggt                                            24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccttctaccg ctttttctcc tccc                                            24

<210> SEQ ID NO 39
<211> LENGTH: 198
<212> TYPE: PRT
```

```
<213> ORGANISM: Homo sapiens

<400> SEQUENCE: 39

Met Ala Ala Thr Cys Glu Ile Ser Asn Ile Phe Ser Asn Tyr Phe Ser
 1               5                   10                  15
Ala Met Tyr Ser Ser Glu Asp Ser Thr Ala Gly Thr Gly Ala Ser Arg
             20                  25                  30
Ser Ser His Ser Ser Asp Ser Gly Gly Ser Asp Val Asp Leu Asp Pro
         35                  40                  45
Thr Asp Gly Lys Leu Phe Pro Ser Asp Gly Phe Arg Asp Cys Lys Lys
     50                  55                  60
Gly Asp Pro Lys His Gly Lys Arg Lys Arg Gly Arg Pro Arg Lys Leu
 65                  70                  75                  80
Ser Lys Glu Tyr Trp Asp Cys Leu Glu Gly Lys Lys Ser Lys His Ala
                 85                  90                  95
Pro Arg Gly Thr His Leu Trp Glu Phe Ile Arg Asp Ile Leu Ile His
            100                 105                 110
Pro Glu Leu Asn Glu Gly Leu Met Lys Trp Glu Asn Arg His Glu Gly
        115                 120                 125
Val Phe Lys Phe Leu Arg Ser Glu Ala Val Ala Gln Leu Trp Gly Gln
    130                 135                 140
Lys Lys Lys Asn Ser Asn Met Thr Tyr Glu Lys Leu Ser Arg Ala Met
145                 150                 155                 160
Arg Tyr Tyr Tyr Lys Arg Glu Ile Leu Glu Arg Val Asp Gly Arg Arg
                165                 170                 175
Leu Val Tyr Lys Phe Gly Lys Asn Ser Ser Gly Trp Lys Glu Glu
            180                 185                 190
Val Leu Gln Ser Arg Asn
        195

<210> SEQ ID NO 40
<211> LENGTH: 230
<212> TYPE: PRT
<213> ORGANISM: Homo sapiens

<400> SEQUENCE: 40

Ala Ala Thr Cys Glu Ile Ser Asn Ile Phe Ser Asn Tyr Phe Ser Ala
 1               5                   10                  15
Met Tyr Ser Ser Glu Asp Ser Thr Leu Ala Ser Val Pro Pro Ala Ala
             20                  25                  30
Thr Phe Gly Ala Asp Asp Leu Val Leu Thr Leu Ser Asn Pro Gln Met
         35                  40                  45
Ser Leu Glu Gly Thr Glu Lys Ala Ser Trp Leu Gly Glu Gln Pro Gln
     50                  55                  60
Phe Trp Ser Lys Thr Gln Val Leu Asp Trp Ile Ser Tyr Gln Val Glu
 65                  70                  75                  80
Lys Asn Lys Tyr Asp Ala Ser Ala Ile Asp Phe Ser Arg Cys Asp Met
                 85                  90                  95
Asp Gly Ala Thr Leu Cys Asn Cys Ala Leu Glu Glu Leu Arg Leu Val
            100                 105                 110
Phe Gly Pro Leu Gly Asp Gln Leu His Ala Gln Leu Arg Asp Leu Thr
        115                 120                 125
Ser Ser Ser Ser Asp Glu Leu Ser Trp Ile Ile Glu Leu Leu Glu Lys
    130                 135                 140
Asp Gly Met Ala Phe Gln Glu Ala Leu Asp Pro Gly Pro Phe Asp Gln
```

```
                    -continued
145                 150                 155                 160

Gly Ser Pro Phe Ala Gln Glu Leu Leu Asp Asp Gly Gln Gln Ala Ser
                165                 170                 175

Pro Tyr His Pro Gly Ser Cys Gly Ala Gly Ala Pro Ser Pro Gly Ser
            180                 185                 190

Ser Asp Val Ser Thr Ala Gly Thr Gly Ala Ser Arg Ser Ser His Ser
        195                 200                 205

Ser Asp Ser Gly Gly Ser Asp Val Asp Leu Asp Pro Thr Asp Gly Lys
    210                 215                 220

Leu Phe Pro Ser Asp Gly
225             230
```

USE OF TRANSCRIPTION FACTORS FOR TREATING INFLAMMATION AND OTHER DISEASES

RELATED APPLICATIONS

This application is a continuation-in-part of PCT Application No. PCT/US01/29340 and having an international filing date of Sep. 20, 2001 and published in English under PCT Article 21(2), which claims priority to provisional application No. 60/234,379, filed Sep. 20, 2000, the entire teachings of which are incorporated herein by reference.

STATEMENT OF GOVERNMENT SUPPORT

Funding for this invention was provided in part by the Government of the United States of America National Institutes of Health Grant R01/CA76323, by National Institutes of Health Grant K08/CA 71429; Grant No. RO1/AR45378 from NIH/NIAMS, Grant No. 1RO1/AI49527-01 from NIH/NIAID and Grant No. 1RO1/CA763230-02 from NIH/NCI. The Government has certain rights in this invention.

FIELD OF THE INVENTION

This invention relates to methods of treating inflammation in a tissue comprising altering the activity of a transcription factor, which is involved in the inflammatory response. The transcription factor is preferably expressed in said tissue in response to a pro-inflammatory agent. The invention also relates to the use of transcription factors to screen compounds that are capable of reducing inflammation. The invention also relates to the use of transcription factors in methods of diagnosing the presence of an inflammatory disease in a tissue of a mammal and methods of monitoring the treatment of an inflammatory disease in a tissue of a mammal.

BACKGROUND OF THE INVENTION

Inflammatory processes generally contribute to host defense against infections and as a stress response to tissue injury. Conversely, inflammation contributes to the chronic or acute pathological processes in autoimmune and cardiovascular diseases and other conditions that lead to tissue injury and destruction. Inflammation is a hallmark of several vascular diseases including atherosclerosis, restenosis, and the vasculopathy associated with transplantation. The most common vascular disease, atherosclerosis, begins when lipoproteins, and in particular low density lipoprotein (LDL) enter the subendothelium and become oxidized. Oxidized LDL stimulates the production of interleukin-1 and other inflammatory cytokines. These cytokines activate adhesion molecules, including VCAM-1, ICAM-1, and E-selectin, on the endothelial surface, which promote the attachment of, and transmigration of monocytes. The expression of the inducible form of nitric oxide synthase (NOS2) has also been shown to be upregulated by inflammatory cytokines and endotoxin in cultured cells found in the atherosclerotic plaque including macrophages, smooth muscle cells, T lymphocytes, and endothelial cells (Esaki, T., et al. 1997. Atherosclerosis 128:39–46; Rikitake, Y., et al. 1998, Atherosclerosis 136:51–7; Xu, R., et al. 1999, Life Sci 64:2451–62). Furthermore, immunohistological studies have demonstrated the expression of NOS2 in the atherosclerotic lesions in these cell types as well (Buttery, L. D., et al. 1996, Lab Invest 75:77–85; Esaki, T., et al. 1997, Atherosclerosis 128:39–46).

The induction of the NOS2 gene is also associated with more acute forms of vascular inflammation such as endotoxemia. The generation of the potent vasodilator, nitric oxide (NO) by NOS2, is at least in part responsible for the hypotension seen in association with bacterial sepsis (Wei, 1995 #1021) (MacMicking, 1995 #1020). NOS2 gene expression is also induced in other types of vascular inflammation including restenosis and in the accelerated atherosclerosis associated with heart transplantation (Ikeda, U., et al. 1998, Clin Cardiol 21:473–6; Lafond-Walker, A., et al. 1997, Am J Pathol 151:919–25).

Rheumatoid arthritis (RA) is a prototypical immune-mediated disease characterized by chronic inflammation in the synovium and the destruction of joints, in which, similar to other inflammatory disorders, a central role for interleukin (IL)-1 and tumor necrosis factor (TNF)-α has been established. These cytokines and bacterial endotoxins have major roles in inflammatory responses via the activation of a variety of transcription factors.

Upon binding of cytokines or other inflammatory mediators to their corresponding receptors, several classes of transcription factors function as mediators of these stimuli. For example, within minutes of interleukin-1 beta (IL-1β treatment, the expression of the immediate early genes cFos and c-Jun are induced. These transcription factors are the constituent proteins for AP-1 (Conca, W., et al. 1991, J Biol Chem 266:16265–8; Conca, W., et al. 1989, J Clin Invest 83:1753–7). One of the target genes of IL-1β, the collagenase gene, can be activated by AP-1 alone (Angel, P., I. et al. 1987, Mol Cell Biol 7:2256–66). Multiple signaling pathways have been implicated in the activation of these immediate early genes by IL-1β including the Janus kinases (JAKs), MAP kinases, and protein kinase A (Hill, C. S., and R. Treisman. 1995, Cell 80:199–211; Karin, M. 1995, J Biol Chem 270:16483–6; Sadowski, H. B., et al. 1993, Science 261:1739–44; Treisman, R. 1996, Curr Opin Cell Biol 8:205–15; Wagner, B. J., et al. 1990, Embo J 9:4477–84).

The propagation of inflammation is dependent on several other transcription factors for the activation of multiple genes. The nuclear factor kappa B (NF-κB) transcription factors are dimeric proteins involved in the activation of a large number of genes in response to inflammatory stimuli. Although originally described to have been important in lymphoid cells and lymphoid specific genes, NF-κB has clearly been shown to play an important role in a whole host of other cell types and target genes. The p50 and p65 subunits of NF-κB have also been shown to bind to other transcription factors through protein interactions often resulting in synergistic transactivation of the target genes of NF-κB (Baeuerle, P. A., and D. Baltimore. 1996, Cell 87:13–20; DiDonato, J. A., et al. 1997, Nature 388:548–54).

One of the major transcriptional circuits implicated in inflammation is the NF-κB/IκB pathway. NF-κB is rapidly activated by proinflammatory cytokines and endotoxins and is involved in the regulation of a large set of inflammatory response genes including various cytokines and chemokines, acute phase proteins, cell adhesion proteins, immunoglobulins, and viral genes. Most of these genes are directly regulated by NF-κB via high affinity binding sites within their respective promoter regions. However, the regulation of a significant number of inflammatory response genes by cytokines cannot be attributed exclusively to direct interaction of NF-κB with binding sites within their regulatory regions, thereby suggesting that additional pathways play critical roles in the transcriptional regulation of these genes.

Osteoarthritis (OA) is another example of a disease having an inflammatory response. OA is a slowly progressive disease with multiple etiologies involving biomechanical, biochemical, and genetic factors, all of which may contribute to the OA lesion in cartilage by disrupting chondrocyte-matrix associations and altering metabolic responses in the chondrocyte. The central role of cytokines, particularly interleukin (IL)-1 and tumor necrosis factor (TNF)-α, in causing the destruction of articular cartilage is well established. It is generally accepted that the chondrocyte is the target of cytoline action, although the sources responsible for generating the cytokines are less clear in the context of OA pathogenesis. Even in the absence of classical inflammation characterized by infiltration of neutrophils and macrophages into joint tissues, elevated levels of proinflammatory cytokines have been measured in OA synovial fluids. Nevertheless, symptoms of local inflammation and synovitis are present in many patients and in animal models of OA. Thus, the fibroblast- and macrophage-like synovial cells, as well as the chondrocytes themselves, are potential sources of cytokines that could induce chondrocytes to synthesize and secrete cartilage-degrading proteases and other cytokines and proinflammatory mediators.

The complexity of the cytokine network that may be involved in OA has increased with the recent discoveries of additional proinflammatory and destructive, as well as inhibitory, cytokines that may amplify or modify the effects of the primary catabolic cytokines. Changes in the patterns of the production of growth factors or their receptors may also contribute to the course of the disease. Aspects of the role of the chondrocyte in OA and lessons from animal models have been reviewed recently. (Goldring M B, *Connec Tiss Res* 1999, 40:1–11; Goldring M B. *Arthritis Rheum* 2000, in press.).

Cytokines and growth factors are produced in joint tissues and released into the synovial fluid, and they act on the resident cells in an autocrine-paracrine manner. Many of these factors are necessary at low levels for normal homeostasis, but in OA their balance may be disturbed. The major proinflammatory cytokines, which are generally also catabolic, include IL-1α and β, TNF-α, IL-6, leukemia inhibitory factor (LIF), oncostatin-M (OSM), IL-8, IL-17, and IL-18. The anti-inflammatory cytokines, IL-4, IL-10, IL-11, IL-13, IL-1 receptor antagonist (IL-1ra) and IFN-γ, are classified as inhibitory cytokines, since they may block the actions of catabolic cytokines. Members of the transforming growth factor (TGF)-β/bone morphogenetic protein (BMP) family, insulin-like growth factor-I, and fibroblast growth factors (FGFs) are considered to be major anabolic factors for cartilage, since they may oppose cartilage destruction by promoting synthesis of matrix proteins. Some of these factors, such as IL-6 and TGF-β, may have dual roles. The role of cytokines in osteoarthritis is described in further detail in Goldring, M. B., *Current Rheumatology Reports*, Jul. 1, 2000, incorporated by reference in its entirety.

The Ets genes are a family of at least thirty members that function as transcription factors (Wasylyk B., H. S. L., Giovane A. 1993, Eur. J. Biochem. 211:7–18). All Ets factors share a highly conserved 80–90 amino acid long DNA binding domain, the ETS domain. Ets factors play a central role in regulating genes involved in development, cellular differentiation and proliferation. Many macrophage, B and T cell specific genes are regulated by Ets factors. The role of Ets factors in the immune system has been substantiated by experiments in mice where the genes encoding several Ets factors have been disrupted by homologous recombination. The PU.1 knockout is characterized by a lack of immune system development (Scott, E. W., et al. 1994, Science 265:1573–7). The Ets-1 knockout mice are characterized by T cell apoptosis and increased terminal B cell differentiation (Muthusamy, N., K. Barton, and J. M. Leiden. 1995, Nature 377:639–42).

Epithelial cell-specific members of the Ets transcription factor family, i.e., ESE-2, ESE-3, and PDEF have been isolated. Recently, a novel member of the Ets factor, called ESE-1, was discovered. Under normal physiological conditions ESE-1 expression is restricted to many epithelial cell types in a variety of tissues with highest expression in the gastrointestinal tract.

ESE-1 is the prototype member of a new subclass of Ets factors and has several interesting features when compared to other Ets family members. First, unlike other Ets factors which are either ubiquitously expressed or primarily expressed in lymphoid cells, ESE-1 appears to have an epithelial-specific expression pattern under basal conditions. Second, unlike all other Ets factors, ESE-1 has two DNA binding domains, a classical Ets domain and in addition an A/T hook domain also found in high mobility group (HMG) proteins. (See Oettgen, P., et al. 1996, Mol Cell Biol 16:5091–106; Oettgen, P., et al. 1999, Genomics 55:358–62; Oettgen, P., et al. 1997, Genomics 445:456–7; and Oettgen, et al., 1997, Mol. Cell Biol. 17(8):4419–33. These references are incorporated herein in their entirety).

One important medical need is the effective treatment of cardiovascular disease, inflammation, and autoimmune diseases. At the moment these diseases are treated with drugs that have inadequate safety profiles and limited efficacy. Currently, the therapeutic alternatives available to treat inflammation consist of the use of corticosteroids or non-steroidal anti-inflammatory agents (NSAIDS). Unfortunately, all of these anti-inflammatory agents are associated with significant side effects, including gastrointestinal irritation and bleeding, bone loss, and fluid retention, some of which can be life-threatening. These anti-inflammatory drugs are therefore not ideal therapeutic agents. Other drugs that target only a single gene involved in inflammatory processes are not effective enough, since only a single component of inflammation is targeted leaving all the other components untouched.

For example, experimental approaches for OA therapy have targeted production or activities of catabolic cytokines. In addition to anticytokine therapy, selective MMP inhibitors targeting enzymes that degrade cartilage-specific collagens and aggrecan also offer the potential to halt cartilage damage. Protein kinases that regulate signal transduction pathways induced by catabolic cytokines have also been proposed as therapeutic targets (Lewis A J, et al. *Curr Opin Chem Biol* 1999, 3:489–494; Badger A M, et al. *Arthritis Rheum* 2000, 43:175–183). These include the stress-activated protein kinases (SAPKs), c-Jun N-terminal kinases (JNKs) and p38 MAP kinase, and the IKK1 and IKK2 kinases that release nuclear factor (NF)-κB from its inhibitor IκB, which are known to be activated in chondrocytes by catabolic cytokines. The loss of cartilage in OA is a consequence not only of the disturbed production of and responsiveness to catabolic factors, but also the failure of cartilage repair once it begins to breakdown. Thus, therapy should begin early and target pivotal catabolic pathways without affecting normal homeostasis. Current procedures for repairing or transplanting articular cartilage that is more severely damaged do not provide long-term restoration of the normal cartilage surface (Buckwalter J A, et al. *Arthritis Rheum* 1998, 42:1331–1342.). Autologous chondrocyte transplantation has been used somewhat successfully in traumatic defects of knee cartilage in young adults. However, the repair of more extensive defects in OA patients will require the development of approaches for genetically engineering chondrocytes prior to transplantation to not only promote cartilage-specific matrix synthesis, but also to counteract the effects of inflammatory and catabolic cytokines (Evans C H, et al., *Arthritis Rheum* 1999, 42:1–16.).

Pharmacological interventions for OA have focused primarily on improving symptoms, although new agents may offer the possibility of preserving normal homeostasis. Since the increased synthesis of MMPs, prostaglandins, and other inflammatory and catabolic factors in OA tissues appears to be related to elevated levels of IL-1 and TNF-α, therapies that interfere with the expression or actions of these cytokines are most promising.

It would be useful to have effective methods of treating different types of inflammation, such as vascular inflammatory disorders, rheumatologic disorders, dermatologic inflammatory diseases, gastrointestinal inflammatory diseases and kidney disorders, to name a few. It would be especially useful to have methods of treating inflammation that modulate the transcription factors that mediate inflammation. It would also be useful to have methods of screening compounds that are capable of reducing an inflammatory response, especially methods that modulate the expression of the transcription factors involved in the response.

SUMMARY OF THE INVENTION

The present invention provides a method of treating inflammation in a mammal comprising altering the activity of a transcription factor involved in the inflammatory response. In preferred methods, the transcription factor is expressed in said mammal in response to a pro-inflammatory agent and the transcription factor is not normally expressed, or is expressed at a low level, in the absence of the pro-inflammatory agent. The methods of the present invention are useful for treating inflammation located in a tissue, organ or synovial fluid of the mammal. In certain methods of the present invention, altering the activity comprises decreasing the activity of the transcription factor. In certain of these embodiments, the step of decreasing the activity of a transcription factor further comprises either decreasing the function of the transcription factor or blocking the expression of the transcription factor.

In yet other methods, altering the activity comprises increasing the activity of the transcription factor. In certain of these methods, the step of increasing the activity of a transcription factor further comprises either increasing the function of the transcription factor or increasing the expression of the transcription factor.

As aforesaid, the transcription factor is one that is involved in an inflammatory response. Examples of transcription factors useful in the methods of the present invention include, but are not limited to an Ets transcription factor, a STAT transcription factor, C/EBPs, HMG protein, e.g., SOX protein, and other proteins having A/T hook domains, EGR-1 or AP-1. One of ordinary skill in the art can readily select useful transcription factors for use in the present methods, based on the teachings disclosed herein.

In preferred embodiments, the transcription factor is selected from the family of Ets transcription factors, including, ESE-1, and ESE-1 related factors, ESE-2, and ESE-3. In especially preferred methods of the present invention, the transcription factor comprises ESE-1. The methods and products of the present invention will be described with reference to ETS transcription factors, and ESE-1 in particular. However, it is to be understood that the invention is not limited thereto. Other transcription factors may also be useful in the present invention. Furthermore, it is to be understood that such reference to the ESE-1 polypeptide refers to naturally occurring and non-naturally occurring peptides and variants thereto. One of ordinary skill in the art can readily determine useful variants of the polypeptides.

The inflammation treated by the present methods, includes inflammation associated with an inflammatory disease, e.g., vascular inflammatory disorders, rheumatologic disorders, dermatologic inflammatory diseases, gastrointestinal inflammatory diseases and kidney disorders. Examples of the rheumatologic disorders include, but are not limited to, rheumatoid arthritis, osteoarthritis, vasculitis, sclereoderma, systemic lupus erthymotosus and collagen vascular disorder. Examples of vascular inflammatory disorders include, but are not limited to bacterial sepsis. Other examples of diseases that can be treated by the present methods include, but are not limited to, atherosclerosis, restenosis, transplantation associated arteriopathy, psoriasis, transplant rejection, multiple sclerosis, diabetes, and Alzheimer's disease and fever.

The step of blocking the expression of the transcription factor can be accomplished in many ways that are known to one of ordinary skill in the art, e.g., inhibiting the activation of the promoter for the gene encoding the transcription factor. In certain embodiments, the step of inhibiting activation further comprises providing a substance that blocks the function or expression of the transcription factor. The substance can be selected by one of ordinary skill in the art but include, e.g., small molecules, peptides, dominant negative mutants, antisense RNAs, and DNA viruses. Examples of a substance that inhibits activation of the ESE-1 transcription factor include ESE-1 dominant negative proteins, e.g., ESE-1 DN1 or ESE-1 DN2.

Similarly, in the methods in which the activity of the transcription factor is increased, this can be accomplished in many ways that are known to one of ordinary skill in the art, e.g., activating the promoter for the gene encoding the transcription factor. In certain embodiments, the step of increasing activation further comprises providing a substance that increases the function or expression of the transcription factor. The substance can be selected by one of ordinary skill in the art but include, small molecules, peptides, dominant positive mutants, antisense RNAs, and DNA viruses. Examples of such substances include, e.g., IκB kinase and p38 kinase. Preferred substances mimic or enhance the activity of the transcription factor.

In certain methods, the transcription factor comprises ESE-1 and the step of inhibiting activation further comprises preventing the binding of binding proteins, e.g., p50 and p65 subunits of NF-κB, to the ESE-1 promoter NF-κB site. In certain embodiments, the step of preventing binding comprises the step of mutating the ESE-1 promoter NF-κB site or otherwise blocking the binding site.

In other methods, the step of inhibiting ESE-1 function comprises preventing or enhancing ESE-1 phosphorylation or acetylation or preventing nuclear translocation.

The substance that alters the activity of the transcription factor can be provided in vivo systemically, or alternatively, the substance is provided to the site of inflammation, depending on the result desired. For example, the substance, e.g., small molecule drugs, peptides, dominant negative mutants by gene delivery mechanisms, antisense RNA, can be used to block the function or expression of the transcription factor, e.g., ESE-1, systemically to treat a disease such as atherosclerosis or rheumatoid arthritis. Alternatively, local delivery of an ESE-1 blocking agent can be used to treat localized inflammation as is seen in restenosis after balloon angioplasty for the treatment of coronary artery disease, or in the joints of rheumatoid arthritis patients or to treat transplant associated arteriopathy. Methods of in vivo administration, e.g., gene therapy are know to one of ordinary skill in the art.

The invention provides methods of screening compounds that are capable of reducing inflammation. One such method comprises: (a) providing cells which do not normally express a measurable transcription factor but do express the transcription factor in the presence of a pro-inflammatory agent; (b) providing to a portion of the cells a compound to be screened; (c) providing a portion of the cells as a control without the compound; (d) providing the pro-inflammatory agent to the cells; (e) measuring the expression of the transcription factor in the cells, and (f) comparing the amount of expression of the transcription factor in the cells containing the compound with the control portion of cells. In preferred methods, the transcription factor is an Ets transcription factor. In especially preferred methods, the transcription factor is ESE-1.

The invention further provides screening methods where the compound of interest is a small molecule, peptide, antisense RNA or viral DNA. The inflammatory agent can be selected by one of ordinary skill in the art. In preferred methods the inflammatory agent comprises a pro-inflammatory cytokine, endotoxin, IL-17, IL-18, oncostatin M, and leukemia inhibitory factor. Examples of pro-inflammatory cytokines include IL-1β, TNF-α, and IL-15, and examples of endotoxin include LPS. Another pro-inflammatory agent comprises a virus.

Examples of cells, which are useful in screening methods of the present invention include, but are not limited to, fibroblasts, synoviocytes, chondrocytes, murine monocytes, glioma cells, osteoblasts, smooth muscle cells, endothelial cells, monocytic cells, and keratinocytes. Examples of smooth muscle cells include vascular smooth muscle cells.

In accordance with another aspect of the present invention, there are provided ESE-1 agonists. Among preferred agonists are molecules that mimic ESE-1, that bind to ESE-1-binding molecules or receptor molecules, and that elicit or augment ESE-1-induced responses. Also among preferred agonists are molecules that interact with ESE-1 or ESE-1 polypeptides, or with other modulators of ESE-1 activities, and thereby potentiate or augment an effect of ESE-1 or more than one effect of ESE-1.

In accordance with yet another aspect of the present invention, there are provided ESE-1 antagonists. Among preferred antagonists are those which mimic ESE-1 so as to bind to an ESE-1 receptor or binding molecules, but not elicit an ESE-1-induced response or more than one ESE-1-induced response. Also among preferred antagonists are molecules that bind to or interact with ESE-1 so as to inhibit an effect of ESE-1 or more than one effect of ESE-1 or which prevent expression of ESE-1.

The invention also provides methods of diagnosing the presence of an inflammatory disease in a mammal comprising: (a) removing a sample from the mammal and (b) measuring the presence and/or amount of a transcription factor wherein the transcription factor is not present in detectable amounts in the sample in the absence of the inflammatory disease. In the methods of the present invention, the sample comprises tissue, synovial fluid, cerebrospinal fluid (CSF), urine or blood. Preferably, the transcription factor is an Ets transcription factor. In certain embodiments, the transcription factor is ESE-1. The inflammatory diseases diagnosed by the methods of the present invention include rheumatological or autoimmune diseases, atherosclerosis, restenosis, transplantation associated arteriopathy, psoriasis, for example. In certain methods, the rheumatological or autoimmune disease comprise rheumatoid arthritis, osteoarthritis, vasculitis, sclereoderma, systemic lupus erthymotosus. The presence or amount of the transcription factor can be measured by methods known in the art and also by methods described herein.

The invention further provides a method of monitoring the treatment of an inflammatory disease in a mammal comprising: removing a sample from the mammal subsequent to said treatment and measuring the presence or amount of a transcription factor wherein the transcription factor is not present in detectable amounts in the mammal in the absence of the inflammatory disease. In the methods of the present invention, the sample comprises tissue, synovial fluid, urine, CSF or blood. Preferably, the transcription factor is an Ets transcription factor. In certain embodiments, the transcription factor is ESE-1. The inflammatory diseases diagnosed by the methods of the present invention include rheumatological or autoimmune diseases, atherosclerosis, restenosis, transplantation associated arteriopathy, psoriasis, for example. Other examples of diseases include rheumatological or autoimmune disease such as rheumatoid arthritis, osteoarthritis, vasculitis, sclereoderma, systemic lupus erthymotosus. In certain embodiments of these methods, the method further comprises repeating the removing and measuring steps at subsequent intervals and comparing the amounts of the transcription factor to determine if the treatment is effective.

The present invention also relates to a pharmaceutical composition for the treatment of inflammation comprising a compound that alters the expression of a transcription factor, e.g., Ets, and a pharmaceutically acceptable carrier. Preferred compositions comprise compounds that alter the expression of ESE-1. Examples of compounds that are useful in such compositions include small molecules, peptides, or antisense RNA. In certain embodiments, the composition further comprises an agent that stimulates cartilage repair, e.g., a cartilage inducing growth and differentiation factor in a collagen scaffold or synthetic polymer.

The present invention further relates to altering the expression of an inflammatory response gene comprising modulating the expression of a transcription factor which affects the expression of the gene. In some embodiments, the step of altering the expression of an inflammatory response gene comprises decreasing the expression or the activity of the transcription factor. The step of decreasing the activity of the transcription factor further comprises either decreasing the function of the transcription factor or blocking the expression of the transcription factor. In other embodiments, altering the expression of an inflammatory response gene comprises increasing the activity of the transcription factor. In certain of these embodiments, the step of increasing the activity of a transcription factor further comprises either increasing the function of the transcription factor or increasing the expression of the transcription factor.

Preferably, the transcription factor is an epithelium specific, e.g., Ets, transcription factor. In certain embodiments, the transcription factor is ESE-1. Examples of inflammatory response genes comprise genes for metalloproteinases, genes associated with apoptosis, genes for nuclear orphan receptor (MINOR), inducible nitric oxide synthase (NOS-2), cyclooxygenase (COX-2), phospholipase A2, angiogenesis genes (VEGF and FGF and their receptors). Examples of metalloproteinases include, e.g., MMP-1, MMP-3, MMP-8, MMP-9, MMP-13, MMP-14, aggrecanases, e.g., ADAM-TS4, ADAM-TS5. Genes associated with apoptosis include FAS and DR5, for example.

A further approach would be to use the methods of the present invention to prevent the detrimental effects of proinflammatory cytokines on cartilage specific matrix protein synthesis by inhibiting expression or action of ESE-1. For example, the methods can be used to reverse the inhibitory effect of ESE-1 on Type II collagen gene expression.

The present invention also relates to a method of treating a disease comprising increasing the activity of a transcription factor, wherein the transcription factor is either not expressed in diseased tissue or expressed in low amounts. The transcription factor increases the expression of a product that is useful for treating the disease. For example, it would be useful to increase nitric oxide synthase (NOS-2), cyclooxygenase (COX-2) or Prostaglandin E2 (PGE2) in certain instances. For increasing PGE2 may actually counter act some of the IL-1 induced effects (e.g., inhibition of type II collagen) in osteoarthritis. Thus, by using the present methods to increase PGE2 activity, instead of other treatments, e.g., NSAIDS, which lose the protective effects of prostaglandins, treatments may be more effective.

BRIEF DESCRIPTION OF THE DRAWINGS

FIG. 1 shows ESE-1 induction to inflammatory stimuli. FIG. 1(a) shows RT-PCR analysis of ESE-1 expression in human aortic smooth muscle cells (HASMCs), human umbilical vein endothelial cells(HUVECs), and the THP-1 monocytic cell line at different time points after stimulation with IL-1β, TNF-α, or LPS (See methods for details of PCR). FIG. 1(b) shows Northern blot analysis of ESE-1 induction in primary human aortic smooth muscle cells. 10 ug of total RNA were used per lane. (See methods for details of Northern blot analysis).

FIG. 2 shows a schematic diagram of the human ESE-1 promoter demonstrating conserved transcription factor binding sites (Ets, NF-κB, Ap-1, and CRE) and the TATA box.

FIG. 3 shows ESE-1 promoter induction by LPS. FIG. 3(A) shows induction of the ESE-1 promoter in RAW 264.7 cells in response to LPS. FIG. 3(B) Effect of mutation in NF-κB site(m ESE-1 promoter) upon activation by LPS.

FIG. 4 shows electrophoretic mobility shift assays (EMSA) with ESE-1 promoter NF-κB site.

FIG. 5 shows ESE-1 transactivation of the promoters of potential target genes. FIG. 5(A) shows cotransfection of the mammalian expression plasmid with luciferase reporter constructs of different potential target genes, including CD44, interleukin-6, NOS2, E-selectin, and ICAM-2. FIG. 5(B) shows cotransfection of ESE-1 with the long (−1485 to +31) and short (−233 to +31) forms of the murine NOS2 promoter.

FIG. 7 shows Mutational analysis of NOS2 Ets binding site. FIG. 7(A) shows cotransfection of wild type NOS2 promoter or the mutated NOS2 promoter with pCI or pCI-ESE-1 mammalian expression vectors. FIG. 7(B) shows evaluation of effect of Ets site mutation on LPS induction.

FIG. 8 shows synergistic effect of NF-κB with ESE-1 upon NOS2 transactivation. Cotransfection experiments of different combinations of the pCI mammalian expression plasmid containing cDNAs encoding either ESE-1, p50, or p65, were performed in RAW 264.7 or RASMCs, with the NOS2 promoter luciferase reporter construct(short).

FIG. 9 shows ESE-1 interaction with p50. FIG. 9(A) shows $^{35}$S-methionine in vitro translated rabbit reticulocyte lysates of p50, p65, and unprogrammed lysate(control) separated by SDS gel electrophoresis. Molecular weight markers are shown on the left. FIG. 9(B) shows binding of p50 to ESE-1, another Ets factor NERF-2, and several deletion constructs, and the GST-fusion protein alone (control). FIG. 9(C) shows a schematic of ESE-1 constructs used in GST-fusion experiments. (See methods for details of the GST-pull down experiment).

FIG. 10 shows expression of ESE-1 in the rat aorta during acute inflammation. Immunohistological evaluation of ESE-1 protein expression in the rat aorta before and 24 hours after systemic administration of endotoxin(see methods for details). HP (high power) LP(low power).

FIGS. 11(a) and 1(b) show induction of ESE-1 mRNA in human chondrocytes by proinflammatory cytokines and endotoxin.

FIG. 11(c) shows induction of ESE-1 mRNA in human synovial fibroblasts by proinflammatory cytokines and endotoxin.

FIG. 11(d) shows induction of ESE-1 mRNA in human LB-12 osteoblasts by proinflammatory cytokines and endotoxin.

FIG. 11(e) shows induction of ESE-1 mRNA in THP-1 human monocytes by proinflammatory cytokines and endotoxin.

FIG. 11(f) shows induction of ESE-1 mRNA in U-138 MG and U-373 MG human glioma cells by proinflammatory cytokines and endotoxin.

Subconfluent cultures of the human costal chondrocyte cell lines, T/C28 a2, C28/I2, C20A4 were incubated in the absence or presence of IL-1β, TNF-α, or IFN-γ for 24 h (a) or for 0.5, 2, 6, 12, or 24 hours (b) and ESE-1 mRNA was analyzed by RT-PCR. Human synovial fibroblasts (c) at passage 4 were incubated in the absence or presence of IL-1β, indomethacin, or a combination of both for 6 hours, 24 hours, and 5 days. RT-PCR analysis was performed using ESE-1 and GAPDH specific primers. Northern blot analysis of ESE-1 mRNA expression in human osteoblasts (d) upon stimulation by IL-1β. Cultures of the human LB-12 osteoblast cell line were incubated in the absence or presence of cycloheximide, IL-1β, hydrocortisone, or combinations thereof for 1, 2, 6, and 24 hours. Stimulation of ESE-1 mRNA by LPS in human monocytes (e). THP-1 cells were grown in the absence or presence of LPS for 1, 2, 6, or 24 hours and ESE-1 mRNA was analyzed by RT-PCR. Kinetics of ESE-1 mRNA induction by IL-1β in human glioma cell lines (f). U-138 MG and U-373 MG glioma cells were grown in the absence or presence of IL-1β for 1, 2, 6, or 22 hours.

Figure 12:
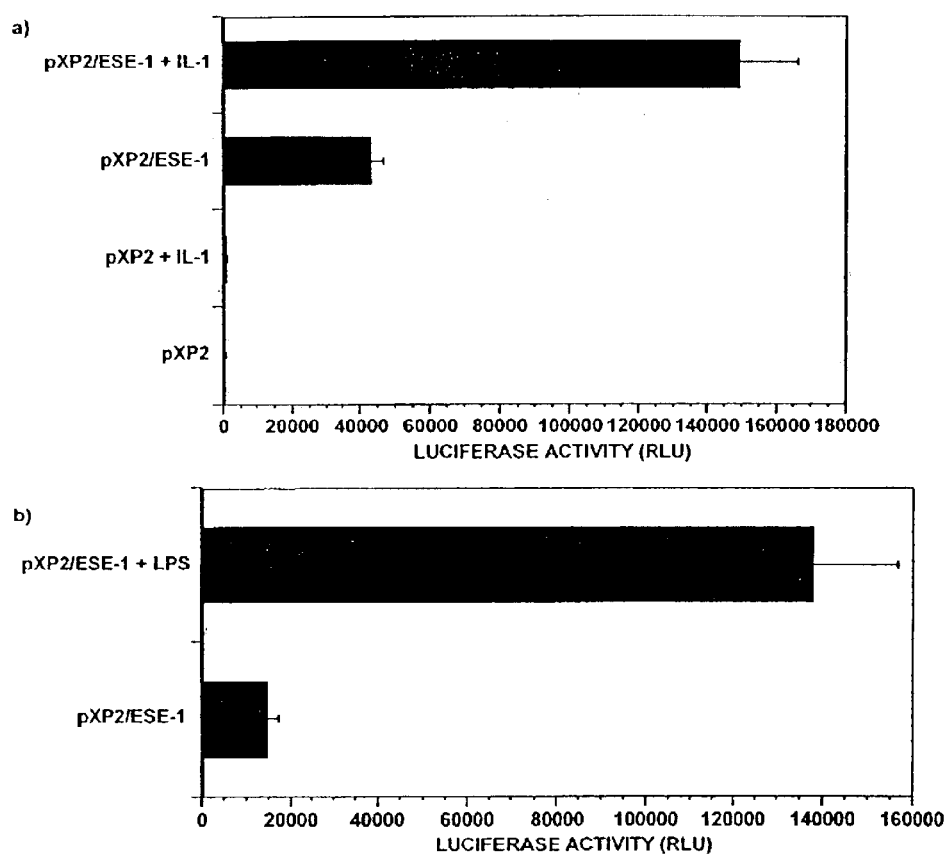
Figure 12:
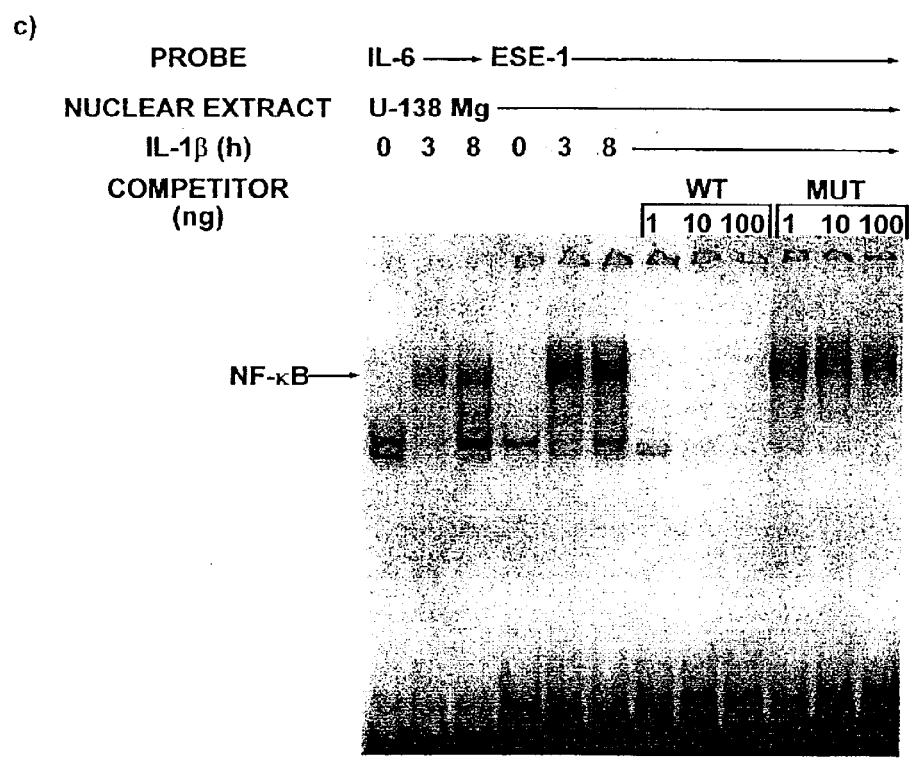
Figure 12:
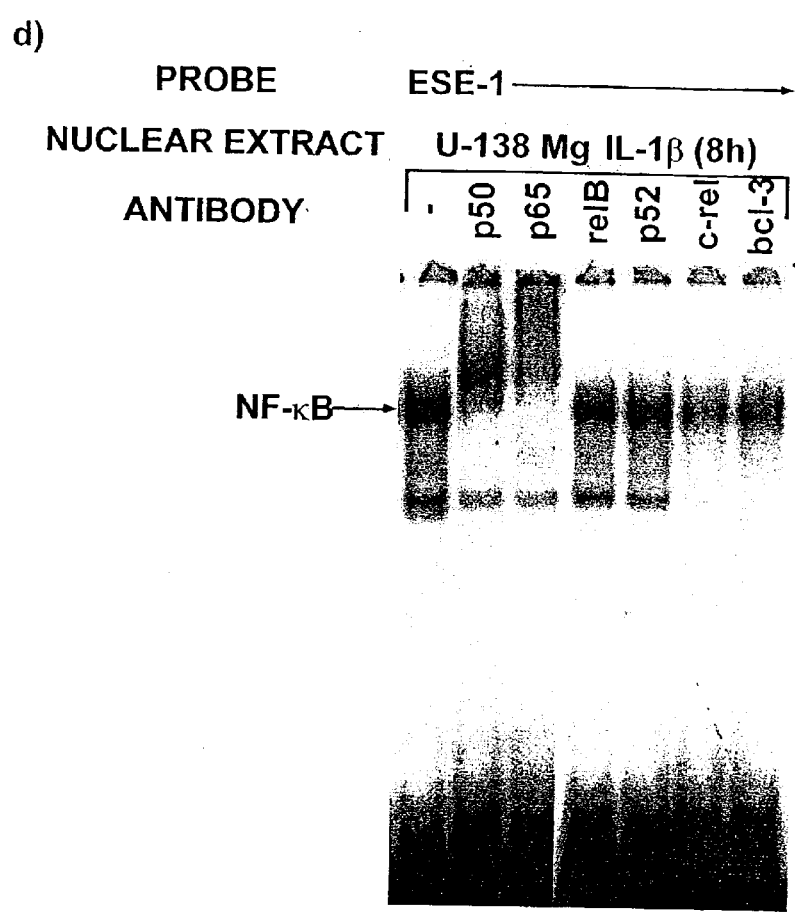
Figure 12:
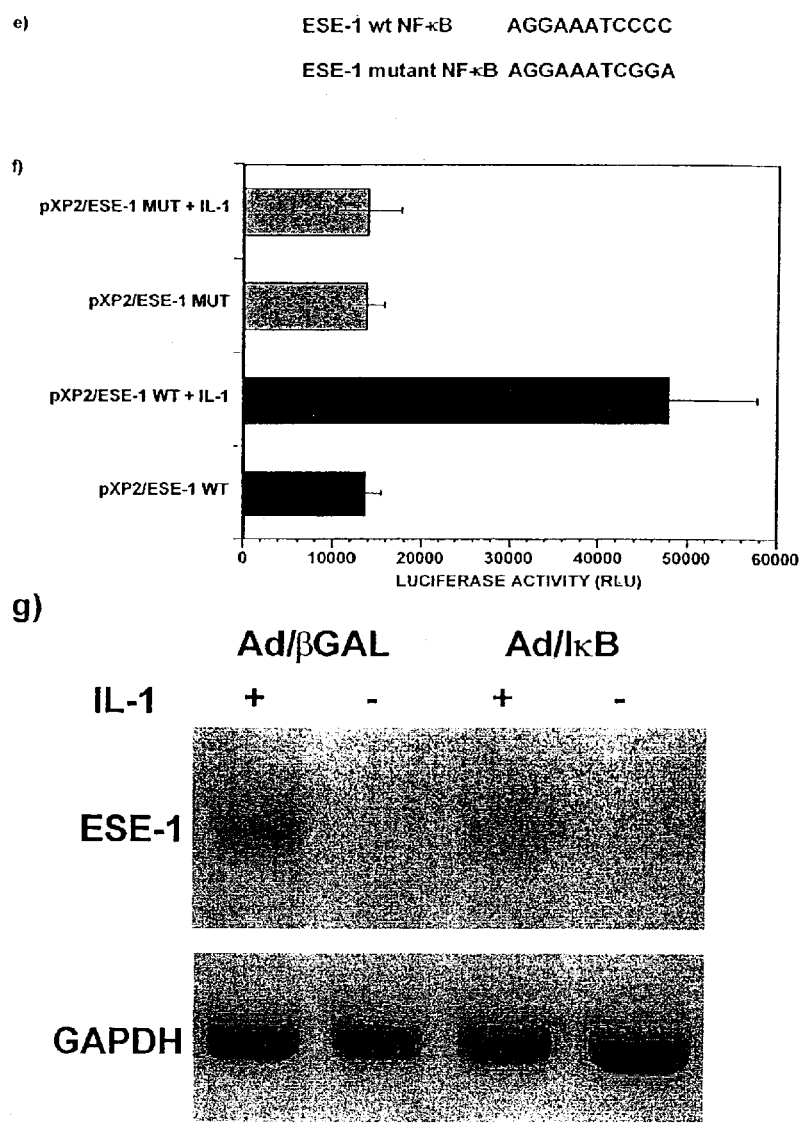

FIG. 12 shows transcriptional activation of the ESE-1 promoter by IL-1β and LPS involves NF-κB.

FIG. 12(a) shows U-138 MG cells which were transfected with either the parental pXP2 luciferase plasmid or the pXP2 luciferase construct containing the ESE-1 promoter (pXP2/ESE-1) and incubated in the absence or presence of IL-1β for 16 h.

FIG. 12(b) shows RAW cells which were transfected with the pXP2/ESE-1 construct and incubated in the absence or presence of LPS for 16 h. Data shown are means of duplicate measurements from one representative transfection. Experiments were repeated three times with different plasmid preparations with comparable results.

FIG. 12(c) shows interaction of NF-κB with the NF-κB binding site in the ESE-1 promoter. Whole cell extracts isolated from U-138 MG cells stimulated with IL-1β for 0, 3, and 8 hours were analyzed by EMSA using the labeled human ESE-1/NF-κB site oligonucleotide or the human IL6/NF-κB site oligonucleotide as probes. Competitions were carried out with either no competitor, or 1, 10, and 100 ng of unlabeled wild type or mutant ESE-1/NF-κB oligonucleotides.

FIG. 12(d) shows that the NF-κB/rel family members p50 and p65 interact with the NF-κB binding site in the ESE-1 promoter. Supershift-EMSAs using whole cell extracts from U-138 MG cells stimulated with IL-1β for 8 hours and the ESE-1/NF-κB probe were carried out with either no antibody, or antibodies against p50, p65, relB, p52, c-rel, and bcl-3. The arrow indicates the NF-κB DNA-protein complex.

FIG. 12(e) shows sequences of the wild type ESE-1/NF-κB site (SEQ ID NO: 24) and the mutation (SEQ ID NO: 25) introduced within the ESE-1 promoter.

FIG. 12(f) shows that mutation of the NF-κB site within the ESE-1 promoter abolishes induction by IL-1β. U-138 MG cells were transfected with the ESE-1 promoter/pXP2 luciferase construct containing either the wild type or a mutant NF-κB site and incubated in the absence or presence of IL-1β. Luciferase activity in the lysates was determined 16 h later. Data shown are means of duplicate measurements from one representative transfection. The experiment was repeated four times with different plasmid preparations with comparable results.

FIG. 12(g) shows that adenovirus-mediated overexpression of IκB inhibits ESE-1 induction by IL-1β. U-138 MG cells were infected with an adenovirus expressing IθB or as a control an adenovirus expressing β-galactosidase prior to stimulation by IL-1β for 8 hours. Total RNA was extracted and analyzed by RT-PCR using ESE-1 and GAPDH specific primers.

Figure 13:
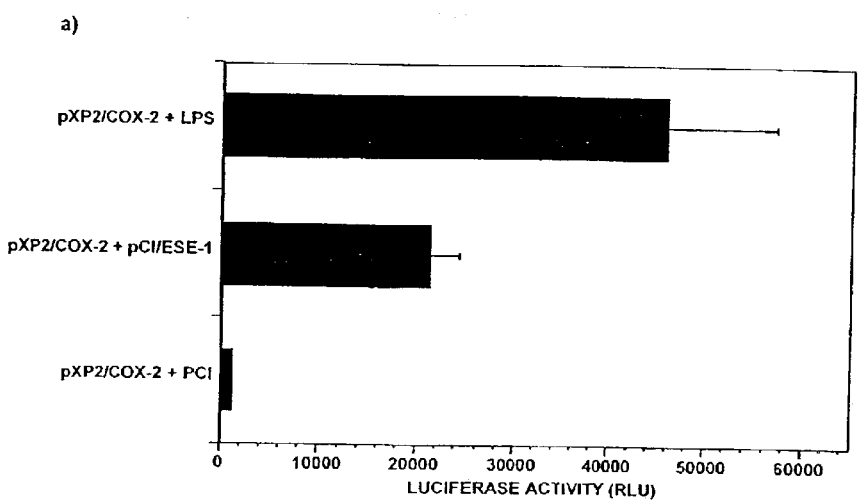
Figure 13:
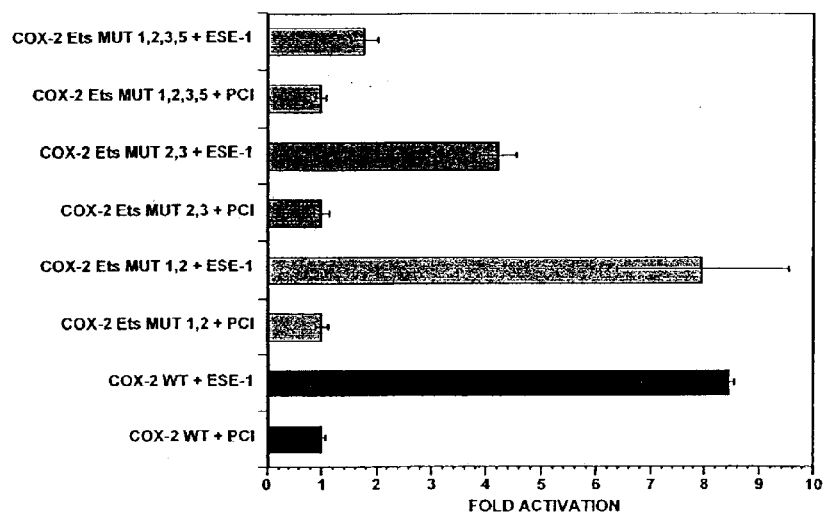
Figure 13:
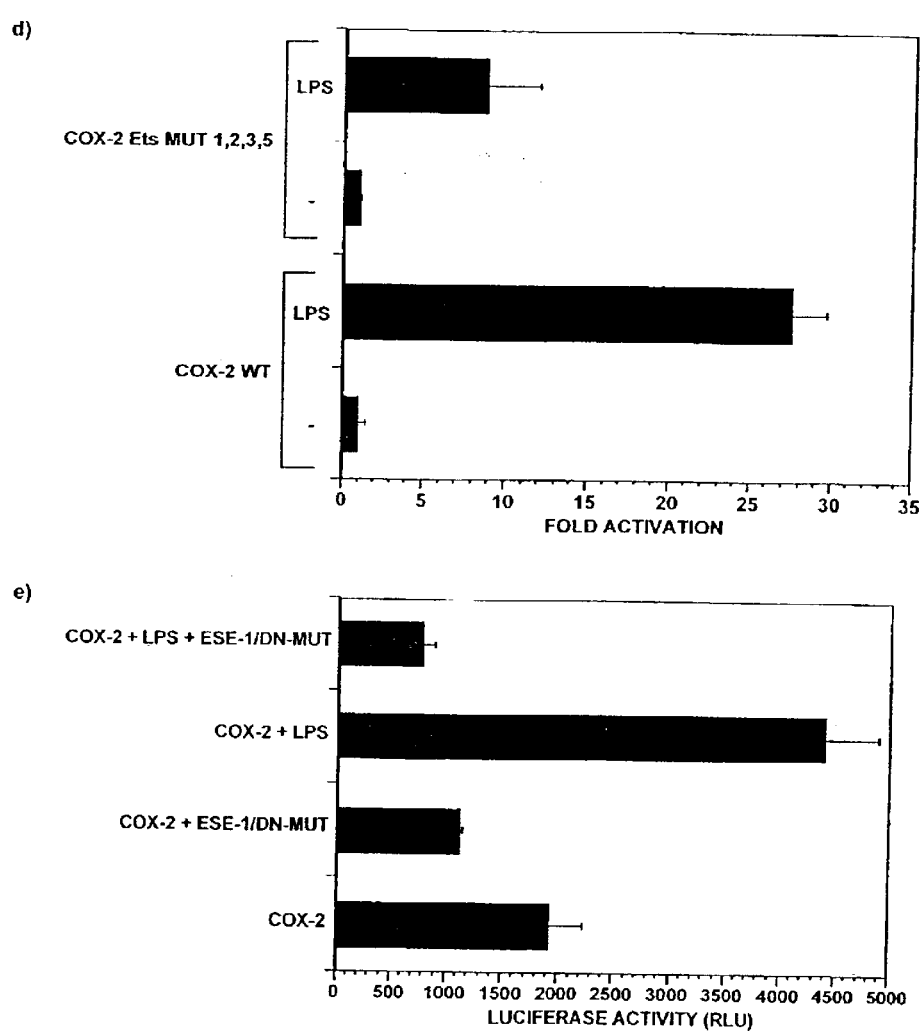

FIG. 13(a) shows RAW cells which were co-transfected with the pXP2 luciferase construct containing the COX-2 promoter (pXP2/COX-2) and the pCI/ESE-1 expression vector and incubated in the absence or presence of LPS. Luciferase activity in the lysates was determined 16 h later.

FIG. 13(b) shows the sequence of the COX-2 promoter (SEQ ID NO: 26). Five putative Ets binding sites are highlighted within the COX-2 promoter sequence.

FIG. 13(c) shows that mutation of multiple Ets binding sites within the COX-2 promoter inhibits induction by ESE-1. RAW cells were co-transfected with the pCI/ESE-1 expression vector and the COX-2 promoter luciferase constructs containing either wild type (WT) or combinations of multiple mutant Ets binding sites (Ets MUT). Luciferase activity in the lysates was determined 16 h later.

FIG. 13(d) shows that mutation of the Ets binding sites reduces LPS-induced transactivation of the COX-2 promoter. RAW cells were transfected with the wild type COX-2 promoter luciferase construct or the COX-2 promoter luciferase containing mutations in the Ets binding sites 1, 2, 3, and 5. Luciferase activity in the lysates was determined 16 h later.

FIG. 13(e) shows that dominant-negative mutant ESE-1 inhibits LPS mediated transactivation of the COX-2 promoter. RAW cells were co-transfected with the pCI expression vector containing a dominant-negative mutant of ESE-1 (ESE-1/DN-MUT) and the COX-2 promoter luciferase constructs. Cells were grown in the absence or presence of LPS. Luciferase activity in the lysates was determined 16 h later. Data shown are means of duplicate measurements from one representative transfection.

Figure 14:
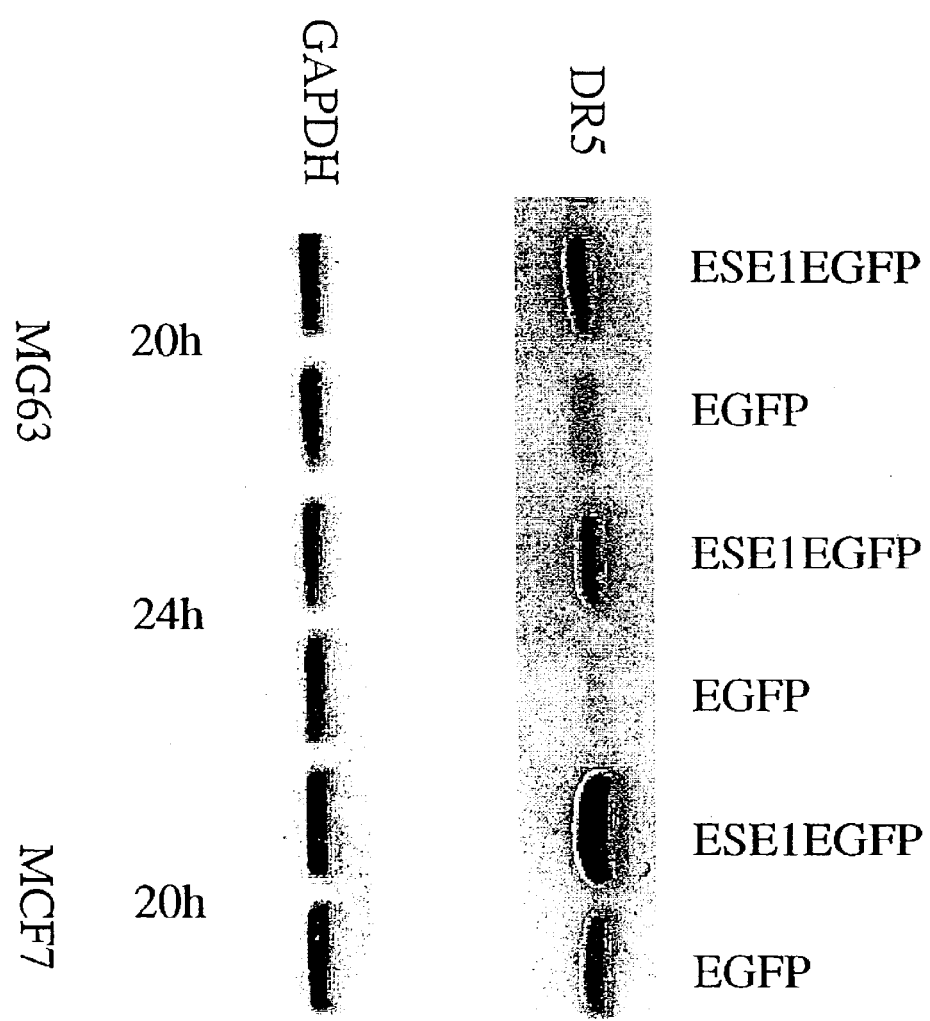

FIG. 14 shows stimulation of DR5 in the presence of ESE-1, EGFP.

Figure 15:
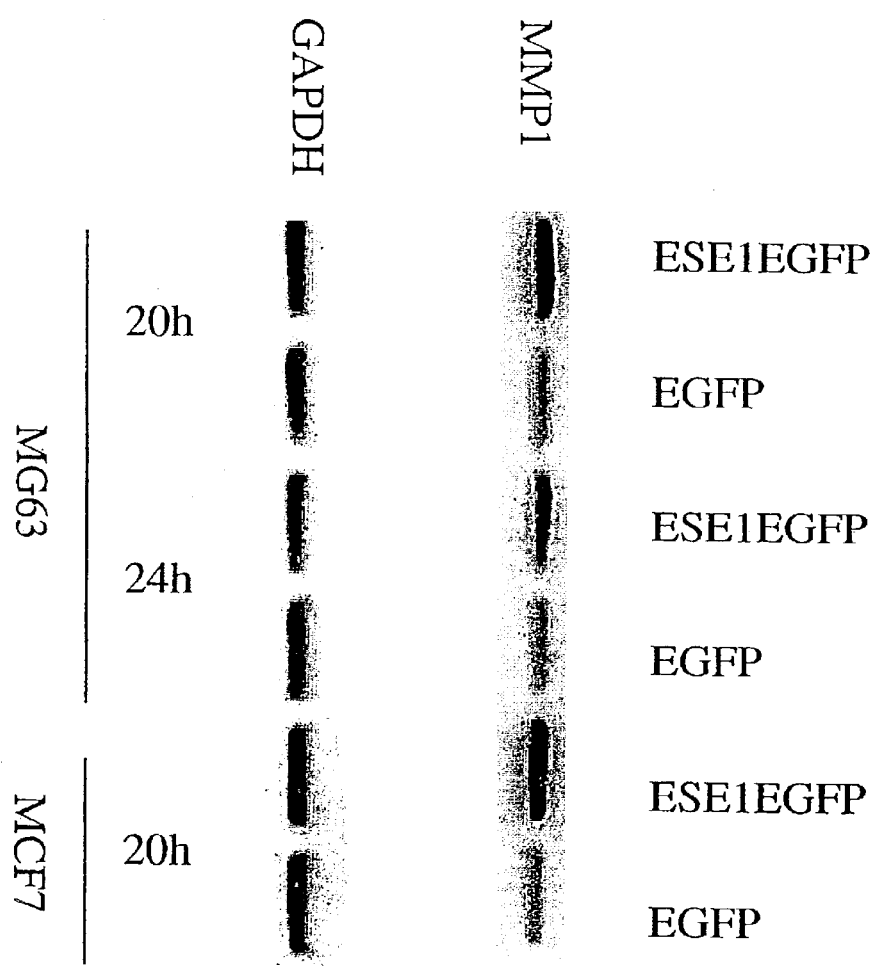

FIG. 15 shows the increase in MMP1 in the presence of ESE1, EGFP.

Figure 16:
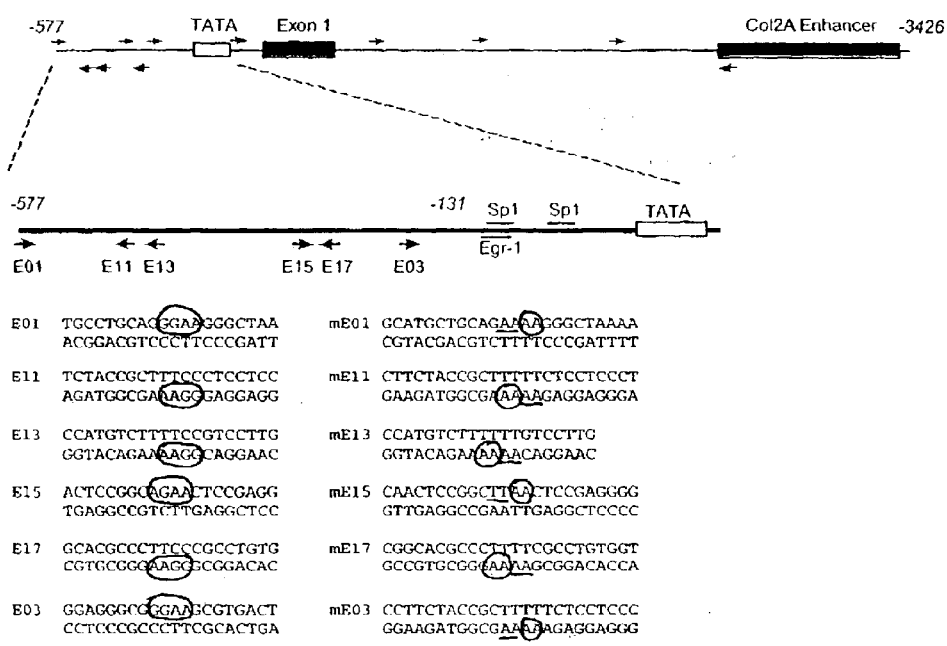

FIG. 16 shows the structure of the COL2A1 promoter. The ETS sites that are potential ESE-1 binding sites are previously identified Sp1, Egr-1/Sp1, and TATA-box sites are represented schematically. The oligonucleotides (SEQ ID NOS 27–38. respectively in order of appearance), containing wild-type and mutant COL2A1 sequences, which were use for EMSAs and site-directed mutagenesis, are listed below. The ESE-1 binding site is marked with a circle and mutations are underlined.

Figure 17:
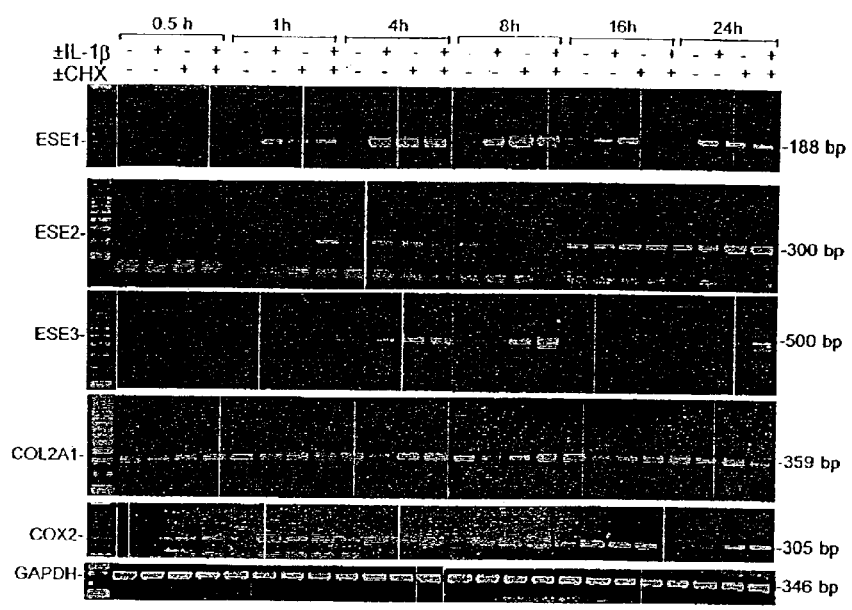

FIG. 17 shows the induction of ESE-1 mRNA by IL-1β in human chondrocytes.

FIG. 17 shows C-28/I2ells plated in serum-containing culture medium and cultured for 5 days, and confluent cultures were changed to serum-free medium containing 1% Nutridoma 24 h before treatment with IL-1β for the times indicated. Cycloheximide (10 μg/ml) was also added in the absence or presence of IL-1β.

FIG. 18 shows the effects of ESE-1, ELF-1 and NERF-2 overexpression on COL2A1 promoter activity in cotransfection assays. The T/C-28a2 cells were cotransfected with pGL2-COL2/4.0 and the empty vector, pCI, or (A) with increasing amounts of the pCI-ESE1 expression vector, (B) with an expression vector, pCI-ESE1, pCI-ELF1, or pCI-NERF2, or with increasing amounts of pCI-ESE1 or pCI-ESE3 (not shown). Cotransfections with the pGL2-basic vector gave values of <1.0 and did not respond to any of the expression vectors (not shown). After lipofection, the cells were incubated for 24 h prior to the addition of IL-1β for a further 18 h, cell harvest, and luciferase assay.

Figure 19:
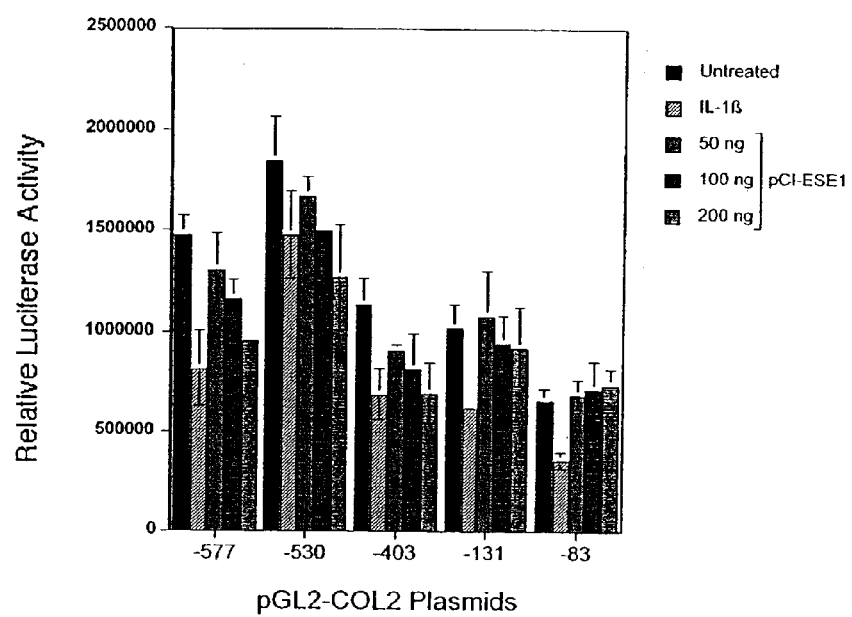

FIG. 19 is a deletion analysis of COL2A1 promoter activity and response to IL-1β and pCI-ESE1 in transient transfections. The C-28/I2 cells were transfected with pGL2 constructs containing COL2A1 sequences, −577/+127 bp, −530/+127 bp, −403/+127 bp, −131 /+127 bp, and −83/+127 bp. Cotransfection with 200 ng of pCI (empty vector) or 50, 100, or 200 ng of pCI-ESE1 was also performed. The cultures were then incubated for 24 h to permit expression of recombinant proteins. The cultures cotransfected with pCI were then treated without or with IL-1β and the incubations continued for a further 18 h. All cultures were harvested at the same time for luciferase assay of reporter gene expression.

Figure 20A:
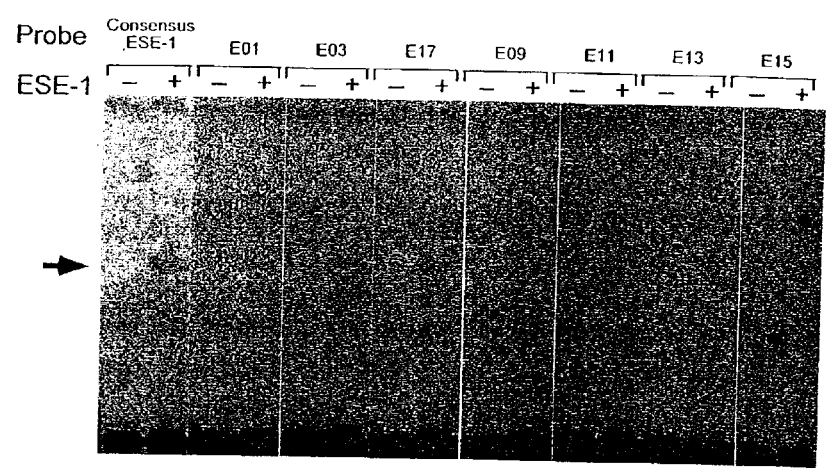

FIG. 20A is an EMSA analysis of ESE-1 binding to the ESE-1 consensus and COL2A1 promoter sequences. End-labeled double-stranded oligonucleotides containing the ESE-1 consensus or wild-type COL2A1 oligonucleotides (see FIG. 1) were incubated in the absence (−) or presence (+) of recombinant ESE-1.

Figure 20B:
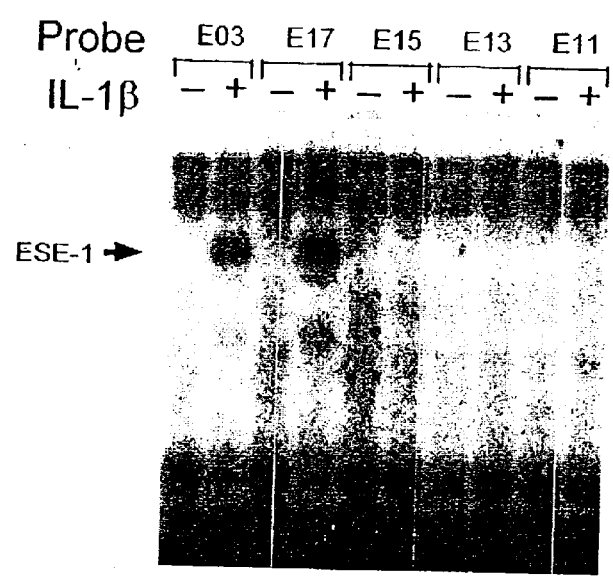

FIG. 20B is an EMSA analysis of nuclear protein binding to COL2A1 promoter sequences. End-labeled double-stranded oligonucleotides containing COL2A1 sequences (see FIG. 1) were incubated with nuclear extracts from untreated (−) or IL-1β-treated (+) C-28/I2 cells.

FIG. 21A shows the structure of an ESE-1 dominant negative protein (ESE-1 DN 1).

FIG. 21B shows the ability of ESE-1 DN1 to block ESE-1 in vitro.

FIG. 21C shows the effect of ESE-1 DN1 on LPS induction of the NOS2 promoter.

FIG. 22A shows the amino acid sequence of ESE-1 DN1 (SEQ ID NO: 39), a dominant negative protein of ESE-1.

FIG. 22B shows the amino acid sequence ESE-1 DN2 (SEQ ID NO: 40), a dominant negative protein of ESE-1.

DETAILED DESCRIPTION OF THE INVENTION

Definitions:

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

This invention relates to the use of a transcription factor, particularly an Ets transcription factor, for treating and/or diagnosing inflammatory diseases. It was previously believed that Ets transcription factor ESE-1 was implicated in the regulation of epithelial-specific genes and under normal physiological conditions ESE-1 expression is restricted to cells of the epithelial cell lineage. It was discovered that ESE-1 is a master switch of inflammation.

This invention pertains to the discovery that this transcription factor is inducible in non-epithelial cells and that stimulation by pro-inflammatory agents, e.g., IL-1β (interleukin-1β) and TNF-α (-α, tumor necrosis factor-α), and endotoxins, e.g., LPS, results in rapid induction of ESE-1 in various non-epithelial cell types. Examples of non-epithelial cell types include, but are not limited to, synovial fibroblasts, chondrocytes, osteoblasts, monocyte/macrophages, and glial cells, as well as endothelial cells and vascular smooth muscle cells.

The upregulation of ESE-1 by the pro-inflammatory agents, e.g., pro-inflammatory cytokines and endotoxin, indicates that certain transcription factors, e.g., ESE-1, are novel mediators of the inflammatory response. Further evidence of a role in inflammatory disorders is provided by the fact that ESE-1 is expressed in the synovium of rheumatoid arthritis patients and patients with Pigmented villonodular synovitis (PVNS) (see examples below). ESE-1 is also expressed in synovial tissues in osteoarthritis patients. Furthermore, ESE-1 is rapidly and transiently induced in non-epithelial cell types, i.e., synovial fibroblasts, chondrocytes, osteoblasts and monocytes/macrophages, by IL-1β, TNF-α and endotoxin (e.g., lipopolysaccharide (LPS)) via activation of NF-κB. See Grall, F., et al., "Responses to the Proinflammatory Cytokines IL-1 and TNF-α in Cells Derived from Rheumatoid Synovium and Other Joint Tissues Involves Nuclear Factor-κB-Mediated Induction of the Ets Transcription Factor ESE-1, *Arthritis & Rheumatism*, Vol. 48, No., 2003 (in press) (incorporated by reference in its entirety).

This invention relates to the use of transcription factors in modulating inflammation in response to many types of different stimuli. More specifically, the invention relates to ESE-1, a novel member of the Ets transcription factor, which is inducible in, e.g., vascular smooth muscle cells, endothelial cells, and cells of the monocyte-macrophage lineage in response to inflammatory stimuli. This induction appears to be mediated via NF-κB. ESE-1 is able to directly bind to the p50 subunit of NF-κB and can augment the NF-κB mediated activation of genes that are induced during inflammation.

While the inventors do not intend to be bound by theory, the following is a description of the basis for the invention. Proinflammatory cytokines and endotoxin bind to their respective cell surface receptors and elicit their pleiotropic responses. Activation of NF-κB is a common rapid response, which in turn leads to translocation of NF-κB from the cytoplasm to the nucleus and activation of a whole set of genes including genes for transcription factors. ESE-1 is one of these target genes related to the presence of a high affinity NF-κB binding site within the ESE-1 promoter. Induction of ESE-1 expression by NF-κB leads to the induction or repression of a set of genes that are regulated by ESE-1. Some of these ESE-1 target genes might be direct targets for NF-κB as well and, as shown below, ESE-1 directly interacts with and cooperates with NF-κB and thereby enhances the response. ESE-1 target genes represent only a subset of cytokine-responsive genes and may specify a functionally related class of genes. Thus, ESE-1 is an alternative target for anti-inflammatory drugs. See Grall, F., et al., J. Biol. Chem. (in press) (incorporated herein by reference).

In the methods of the present invention, the transcription factor modulates a variety of genes (target genes) that contribute to local inflammatory processes in disorders such as rheumatoid arthritis and other inflammatory diseases. Target genes include, but are not limited to, the COX-2 gene, inducible nitric oxide synthase (iNOS), matrix metalloproteinases (MMPs), adhesion molecules, other cytokines, and chemokines. Additional targets are likely to be found among other cytokine-responsive genes. The COX-2 gene is one example of a target for ESE-1, since ESE-1 binds to several sites within the COX-2 promoter and enhances COX-2 promoter activity. We show here that the COX-2 promoter is indeed a target for ESE-1, since a dominant-negative ESE-1 mutant as well as mutation in multiple ESE-1 binding sites efficiently inhibit LPS-mediated activation of the COX-2 promoter.

Unlike other Ets transcription factors, ESE-1 has two DNA binding domains, a classical Ets domain and an A/T hook domain found in HMG proteins. Both DNA binding domains are capable of binding to the p50 subunit of NF-κB. The p50 and p65 subunits of NF-κB can act synergistically with ESE-1 to enhance the transactivation of the NOS2 promoter by ESE-1. An ESE-1 binding site within the NOS2 promoter has been identified, the site directed mutagenesis of which completely abolishes the ability of ESE-1 to transactivate the NOS2 promoter, and leads to a 60% reduction in the inducibility of promoter by endotoxin. Finally in a rat model of endotoxemia, associated with acute vascular inflammation, ESE-1 is strongly expressed in vascular endothelium, and vascular smooth muscle cells by immunohistological analysis.

The inducible form of nitric oxide synthase (NOS2) is also a preferred target for ESE-1. NOS2 is induced in response to inflammatory cytokines in vascular smooth muscle cells, endothelial cells, and monocytes. Ets factors have not previously been shown to be important for the inducibility of the NOS2 gene. Although NOS2 is generally considered an inducible enzyme, that is not constituitively expressed, NOS2 has been shown to be highly expressed in fetal and adult bronchial epithelium (Sherman, T. S., et al. 1999, Am J Physiol 276:L383–90). Interestingly, we also determined the highest level of ESE-1 expression in bronchial epithelium. The functions of NO in the mature airways include smooth muscle relaxation, neurotransmission, bacteriostasis, and modulation of plasma exudation, mucin secretion, and ciliary motility. Constituitive expression of NOS2 has also recently been demonstrated at lower levels in both gastric and colonic epithelium, and is enhanced in association with infection or neoplasia (Ambs, S., et al. 1998, Cancer Res 58:334–41; Fu, S., et al. 1999, Gastroenterology, 116:1319–29).

Our results are the first demonstration that Ets factors may be able to regulate NOS2 gene expression. Rudders, S., et al., J. Biol. Chem. (in press) (incorporated herein by reference).

Other gene targets for ESE-1 include several keratinocyte terminal differentiation markers such as transglutaminase 3, SPRR1, SPRR2A (Oettgen et al., 1997), and profilaggrin, as well as the transforming growth factor β type II receptor (TGF-βRII) (Choi et al., 1998), endo-A/keratin-8, and HER-2 gene. Each of these genes contain a functionally relevant ESE-1 binding site within their regulatory regions that binds and responds to ESE-1.

Other genes, including urokinase-type plasminogen activator (U-PA), MMP-1, MMP-3, TNF-α, scavenger receptor, ICAM-1, ICAM-2, and IL-12 have been shown to depend on Ets factors for their inducibility by cytokines such as IL-1 or TNF-α, and are also useful targets in the present invention. Many additional cytokine-responsive genes contain putative Ets binding sites within their regulatory regions, including COX-2, NOS-2, and MMP-13.

Thus, any gene that contains a functionally relevant ESE-1 binding sites within its regulatory region that bind and respond to ESE-1 is a useful target in the methods of the present invention.

In addition to the role of ESE-1 as a transcriptional activator, ESE-1 also acts as a transcriptional repressor of various genes including the prostate specific antigen and keratin 4 gene. Several of these ESE-1 target genes have been associated with inflammatory processes. IL-1 induces SPRR1 expression in differentiating keratinocytes which directly correlates with the upregulation of ESE-1 and the IL-1 receptor type I during keratinocyte differentiation. ESE-1 is not expressed in undifferentiated keratinocytes.

In osteoarthritis, there is a two pronged effect caused by inflammatory cytokines, such as IL-1 which causes cartilage degradation. Briefly, an increase in Il-1 expression, increases products of inflammation, (e.g., proteases) which cause cartilage breakdown. Examples of these proteases include the MMPs, especially MMP-13. An increase in IL-1 also results in repression of cartilage matrix synthesis and repair via a decrease in type II collagen gene expression.

Presently known treatments for osteoarthritis address the first prong. That is, the treatments target the production of the proteases that breakdown the cartilage. However, the cartilage is not repaired, due to repression of the pathway that controls cartilage matrix synthesis. Thus, it would be desirable to be able to prevent or decrease repression of type II collagen gene expression, as well as inhibit protease production. Thus, it would be desirable to have treatments for osteoarthritis that prevent destruction (via proteases) and permit repair (via type II collagen gene expression). Similarly, it would be useful to decrease these effects during tissue engineering and cartilage implantation.

ESE-1 acts as a transcriptional repressor of the chondrocyte-specific type II collagen gene and may also decrease expression of aggrecan and other genes in association with cartilage matrix synthesis and repair. Thus, by blocking ESE-1 activity, the genes for synthesizing and repairing cartilage are transcribed. The methods of the present invention are useful for treating osteoarthritis. Inhibition or a decrease in expression or activity of ESE-1 will prevent destruction of cartilage via proteases that are induced by IL-1. In addition, repression of type II collagen gene expression, by ESE-1 is reduced. Thus, repair of cartilage can occur. Similarly, these methods can be used during tissue engineering and cartilage implantation to eliminate cytokine-induced effects, i.e., to prevent destruction of the cartilage by the proteases and reduce type II collagen gene repression.

Psoriasis is associated with the action of various inflammatory cytokines and strongly enhances expression of SPRR1 and SPRR2A. Similarly, enhanced levels of TGF-βRII are observed in synovial tissues of RA patients with an active inflammatory process, possibly correlating with increased levels of ESE-1. Interestingly, TNF-α downregulates PSA gene expression in LNCaP prostate cancer cells correlating with the repressor function of ESE-1 on the PSA promoter. ESE-1 represses the PSA promotor. TNF most likely enhances ESE-1 expression which then leads to repression of the PSA gene.

Thus, in certain diseases, it is desirable to increase the expression, or activity of, the transcription factor, e.g., ESE-1, in order to repress the expression of certain genes. In other cases, it is desirable to increase the expression, or activity of, the transcription factor, e.g., ESE-1, in order to increase the expression of certain genes. One of ordinary skill in the art can determine when it is desirable to do so, depending on the disease of interest.

As aforesaid, the methods of the present invention are directed to any transcription factor involved in the inflammatory process. Examples of such transcription factors include, but are not limited to Ets transcription factors, STAT transcription factors, C/EBPs, HMG proteins, e.g., SOX proteins, EGR-1 or AP-1. Ets transcription factor family includes ESE-1, ESE-2, ESE-3, PDEF and Ets-1, Ets-2, ERG, SAP-1, ELK-1, ERP-1, TEL-1, TEL-2, PU.1 and FLI-1.

As described above, ESE-1 has two binding domains including a classical Ets domain and an A/T hook domain. A/T hook domains are found in another family of transcription factors, the high mobility group(HMG) proteins. These factors are nonhistone chromosomal proteins that alter chromatin structure by binding to AT-rich DNA sequences. DNA binding of HMG proteins is mediated by A/T hook DNA binding domains which often exist in tandem clusters of two or three domains which facilitate stronger binding to two or more tandemly placed A/T rich DNA sequences. HMG proteins have recently been implicated in enhancing inflammatory responses. In addition to affecting DNA structure, they also act to enhance transcription by recruiting additional proteins such as NF-κB, ATF-2/c-Jun, and IRF-1 (Perrella, M. A., et al. 1999, J Biol Chem 274:9045–52). The binding of the p50 subunit of NF-κB has been shown to be mediated via one of these A/T hook domains (Zhang, X. M., and G. L. Verdine. 1999 J Biol Chem 274:20235–43). HMG-I(Y) expression is induced in vascular smooth muscle cells in response to inflammatory stimuli including endotoxin and an interleukin-1β (Pellacani, A., et al. 1999, J Biol Chem 274:1525–32.) The A/T hook domain within ESE-1 may facilitate mediation of the inflammatory response either by recruiting other proteins such as p50, or by enhancing binding of ESE-1 or other factors by altering DNA structure through binding to A/T rich sequences. Thus, other transcription factors, like HMG proteins, which contain this A/T hook domain may be useful in the present invention.

Other transcription factors for use in the present invention include those that are able to bind to the p50 subunit of NF-κB. One of ordinary skill in the art will be able to determine which transcription factors have this property. For example, the ability of other Ets factors to bind to the p50 subunit of NF-κB has been shown for other Ets factors including Ets1 and ELF-1 (Babaei, S., et al., 1998, Circ Res 82:1007–15; Gossen, M., and H. Bujard, 1992. Proc Natl Acad Sci U S A 89:5547–51). For both of these Ets factors the interaction occurs via the conserved Ets DNA binding domain. For the NOS2 gene, there was a marked synergistic effect with the combination ESE-1, p50, and p65.

Another family of transcription factors that have been shown to mediate both signal transduction and act as transcription factors is the STAT (signal transducers and activators of transcription) family (Ihle, J. N., et al., 1994, Trends Biochem Sci 19:222–7). Their association with specific phosphotyrosine peptides on the cytoplasmic domain of cytokine receptors activates these factors. Upon association with these peptides the STATs become phosphorylated by Jak tyrosine kinases. The activated STATs act as transcription factors and bind to DNA as dimers. The action of several cytokines including gamma interferon, interleukin-1, and interleukin-6, has been shown to be mediated at least in part by STAT proteins (Stahl, N., et al., 1995, Science 267:1349–53; Tsukada, J., et al., 1996, (published erratum appears in Mol Cell Biol 1996 Jun.;16(6):3233). Mol Cell Biol 16:2183–94).

CAAT/enhancer-binding proteins (C/EBPs) are a family of leucine zipper transcription factors, which have been shown to mediate various aspects of inflammation and immunity (Lekstrom-Himes, J., and K. G. Xanthopoulos. 1998, J Biol Chem 273:28545–8). Several of the cytokines including IL-6, IL-1, and TNF-α, have been shown to induce the expression of C/EBP (Poli, V. 1998, J Biol Chem 273:29279–82; Shirakawa, F., et al., 1993, Mol Cell Biol 13:1332–44). Some of the target genes that have been described for these transcription factors include GM-CSF, G-CSP, and NOS2 (Poli, V. 1998, J Biol Chem 273:29279–82). C/EBP factors have also been shown to be able to interact with NF-κB (Stein, B., et al., 1993, Mol Cell Biol 13:3964–74).

Methods of Treating Diseases:

The methods of the present invention for treating inflammation in a mammal comprise altering or modulating the activity of a transcription factor expressed in the cells of a tissue, organ or synovial fluid of the mammal. As described above, the transcription factor, e.g., ESE-1, is not normally expressed in these cells in the absence of a pro-inflammatory agent.

The term altering or modulating as defined above includes both up-regulation (i.e., turning on or increasing) and down regulation (i.e., turning off or decreasing) expression or activity of the transcription factor.

Thus, decreasing the activity of a transcription factor includes either decreasing, i.e., down-regulating, the activity of the transcription factor or down regulating, including blocking, the expression of the transcription factor. Methods of down-regulating expression of the transcription factor can be accomplished in many ways that are known to one of ordinary skill in the art, e.g., inhibiting the activation of the promoter for the gene encoding the transcription factor, using dominant negative mutants, antisense RNAs, and DNA viruses.

Methods of downregulating activity of the transcription factor include adding inhibitors that prevent binding of the transcription factor to its target genes prevent interaction of ESE-1 with other proteins, prevent phosphorylation or acetylation of ESE-1, prevent nuclear translocation of ESE-1. Examples of such inhibitors include small molecules, ESE-1 polypeptide antagonists, antibodies that bind to ESE-1 binding regions and other substances that can be selected by one of ordinary skill in the art based on their knowledge and the teachings herein.

In certain diseases, treatment may require up-regulating the activity of the transcription factor and/or expression of the transcription factor. For example, in certain diseases, it has been found that induction of ESE-1 represses the expression of certain genes, e.g., PSA. Thus, it would be desirable to increase expression of ESE-1 or the activity of the ESE-1 polypeptide to treat diseases associated with the increase in PSA production, e.g., prostate cancer. In other diseases, it is desirable to increase blood flow to an area, e.g., in cases of stroke or heart attack. Thus, it would be useful to increase ESE-1 production in a localized area, which in turn would increase vasodilation in that area, e.g., in cases of stroke. In cancer, increasing ESE-1 may lead to inflammatory responses that destroy the cancer.

In other methods of treating diseases, the expression of an inflammatory response gene is altered by modulating the expression of a transcription factor, which affects the expression of the gene. Examples of inflammatory response genes comprise genes for metalloproteinases, genes associated with apoptosis, genes for nuclear orphan receptor (MINOR), inducible nitric oxide synthase (NOS-2) and cyclooxygenase (COX-2). Examples of metalloproteinases include, e.g., MMP-1, MMP-3, MMP-8, MMP-9, MMP-13, MMP-14, and aggrecanases (e.g., ADAM-TS4, ADAM-TS5). Genes associated with apoptosis include e.g., FAS, and DR5. These methods can be used to prevent detrimental effects of proinflammatory cytokines on cartilage by inhibiting expression or action of ESE-1.

In some embodiments, the expression of the inflammatory response gene is decreased by decreasing the expression or the activity of the transcription factor. Methods of decreasing the activity of the transcription factor are known in the art and include, e.g., decreasing the function of the transcription factor or blocking the expression of the transcription factor. In other embodiments, altering the expression of the inflammatory response gene involves increasing the activity of the transcription factor. The activity of a transcription factor can be increased by methods known in the art, e.g., either increasing the function of the transcription factor or increasing the expression of the transcription factor. Preferably, the transcription factor is an Ets transcription factor, most preferably ESE-1.

The inflammation treated by the present methods includes inflammation associated with an inflammatory disease, e.g., vascular inflammatory disorders, rheumatologic disorders, dermatologic inflammatory diseases, gastrointestinal inflammatory diseases and kidney disorders. Examples of the rheumatologic disorders include, but are not limited to, rheumatoid arthritis and osteoarthritis, vasculitis, scleroderma, and systemic lupus erythematosus. Examples of vascular inflammatory disorders include, but are not limited to bacterial sepsis. Other examples of diseases that can be treated by the present methods include, but are not limited to, atherosclerosis, restenosis, transplantation associated arteriopathy, psoriasis, autoimmune diseases and Alzheimer's Disease.

In the methods in which the activity of the transcription factor is increased, this can be accomplished in many ways that are known to one of ordinary skill in the art, e.g., activating the promoter for the gene encoding the transcription factor. In certain embodiments, the step of increasing activation further comprises providing a substance (agonist) that increases the function or expression of the transcription factor. The substance can be selected by one of ordinary skill in the art but include, e.g., small molecules and peptides. Examples of such substances include, e.g., IKB kinase, p38 kinase and proinflammatory agents, such as cytokines and endotoxins. Preferred substances mimic or enhance the activity of the transcription factor.

In certain methods, the transcription factor comprises ESE-1 and the step of inhibiting activation further comprises preventing the binding of binding proteins, e.g., p50 and p65 subunits of NF-κB to the ESE-1 promoter NF-κB site. The step of preventing binding may comprise the step of mutating the ESE-1 promoter NF-κB site or otherwise blocking the binding site.

The substance that alters the activity of the transcription factor can be provided in vivo systemically, or alternatively, the substance is provided to the site of inflammation, depending on the result desired. For example, the substance, e.g., small molecule drugs, peptides, dominant negative mutants by gene delivery mechanisms, antisense RNA, can be used to block the function or expression of the transcription factor, e.g., ESE-1, systemically to treat a disease such as atherosclerosis or rheumatoid arthritis. Alternatively, local delivery of an ESE-1 blocking agent can be used to treat localized inflammation as is seen in restenosis after balloon angioplasty for the treatment of coronary artery disease, or in the joints of rheumatoid arthritis patients.

Methods of Screening for Agonist and Antagonist Compounds

As shown herein, up-regulation of ESE-1 turns on, i.e., transactivates, genes under ESE-1 control and down-regulation of ESE-1 will turn off genes under ESE-1 control.

Transcription factors such as ESE-1 function by activating or repressing genes that they regulate. As aforesaid, ESE-1 controls a number of genes involved in the inflammatory process. Also as aforesaid, modulation of this function is useful in developing therapeutics to control inflammatory disease conditions. Thus, one embodiment of the invention provides for screening for compounds that modulate ESE-1 expression or ESE-1 polypeptide activity. The term modulate includes both up-regulation (i.e., turning on or increasing) and down regulation (i.e., turning off or decreasing) expression or activity. Thus, ESE-1 may be employed in a screening process for compounds which activate (agonists) or inhibit activation (antagonists) of this transcription factor and/or the genes that it regulates.

Certain methods involve contacting a cell or an isolated system (e.g., a solution) containing ESE-1 gene or polypeptide with the agent that is to be screened for ESE-1 modulatory activity and detecting the binding of that agent to the gene or polypeptide. Methods of assaying for binding interactions are well known to those of ordinary skill in the art.

Compounds that bind to ESE-1 nucleic acid or polypeptide are expected to provide lead compounds for therapeutic evaluation and/or development.

The invention provides methods of screening compounds that are capable of reducing inflammation (i.e., ESE-1 antagonists). One such method involves the use of cells, which do not normally express a measurable transcription factor but do express the transcription factor in the presence of a pro-inflammatory agent. In this method a portion of the cells are contacted with a compound to be screened and another portion of the cells is used as a control without the compound. A proinflammatory agent is also added to the cells and the expression of the transcription factor in the cells is measured. The amount of expression of the transcription factor in the cells containing the compound is compared with the control portion of cells. Methods of measuring the expression of the transcription factor are known in the art and are examples are described herein. In one example of such screening methods, the transcription factor is an Ets transcription factor, preferably ESE-1. However, the use of other transcription factors is envisioned as well.

Examples of cells which are useful in screening methods of the present invention include, but are not limited to, fibroblasts, synoviocytes, chondrocytes, monocytes, glioma cells, osteoblasts, smooth muscle cells, endothelial cells and monocytic cells. Examples of smooth muscle cells include vascular smooth muscle cells.

Another method uses cells which do not normally express the transcription factor of interest, e.g., ESE-1, but are transfected to express the transcription factor in the presence of a pro-inflammatory agent. Such transfection methods are known in the art. Useful cells include cells from mammals, yeast, Drosophila or E. coli. In particular, a polynucleotide encoding ESE-1 is employed to transfect cells that do not normally express ESE 1 to thereby express the ESE-1. Cells expressing the polypeptide are then contacted with a test compound to observe binding, stimulation or inhibition of a functional response. In one embodiment, this technique is employed to screen for compounds which inhibit activation of ESE-1 by contacting the cells which encode the polypeptide with a proinflammatory agent, a molecule that binds ESE-1 and a compound to be screened. Inhibition of the signal generated by the ESE-1 binding molecule indicates that a compound is a potential antagonist for the ESE-1, i.e., inhibits activation of the polypeptide. The technique may also be employed for screening of compounds which activate the polypeptide by contacting such cells with compounds to be screened and determining whether such compound generates a signal, i.e., activates the polypeptide.

The pro-inflammatory agent can be selected by one of ordinary skill in the art. In preferred methods the inflammatory agent comprises a pro-inflammatory cytokine, endotoxin, IL-17, IL-18, oncostatin ne, and leukemia inhibitory factor. Examples of pro-inflammatory cytokines, include IL-1β, IL-1S and TNF-α, and examples of endotoxin include LPS.

In another method cells are transfected with an ESE-1 response reporter construct and the response to cytokines is measured in the absence or presence of the test compound.

Similar methods can also be used for screening for compounds that up-regulate (e.g., a pro-inflammatory agent) or down regulate (e.g., an ESE-1 repressor agent) the expression or activity of the transcription factor and therefore modulate inflammatory response. For example, in one such method to screen for pro-inflammatory agents, cells that do not normally express the trasncription factor are used. A portion of the cells are contacted with a compound to be screened for increased ESE-1 expression and another portion of the cells is used as a control without the compound. Expression of the transcription factor in the cells is measured. The amount of expression of the transcription factor in the cells containing the compound is compared with the control portion of cells. If the expression increases in the presence of the compound, it is a proinflammatry agent. This agent can then be retested, if desired, in the previous methods in order to find compounds that prevent inflammation caused by this agent. Or this agent can be used when it is desirable to increase ESE-1 expression, e.g., to repress PSA expression.

Another method involves screening for compounds which are antagonists and thus inhibit activation of the ESE-1 by determining inhibition of binding of labeled ligand to cells which have the polypeptide on the surface thereof. Such a method involves transfecting a eukaryotic cell with DNA encoding ESE-1 such that the cell expresses the polypeptide on its surface. The cells are then contacted with a compound in the presence of a labeled form of a known ligand, e.g., p50. The ligand can be labeled, e.g., by radioactivity. The amount of labeled ligand bound to the polypeptide is measured, e.g., by measuring radioactivity associated with transfected cells or membrane from these cells. If the compound binds to the ESE-1, the binding of labeled ligand to the polypeptide is inhibited as determined by a reduction of bound labeled ligand.

The present invention also provides a method for determining whether a ligand not known to be capable of binding to an ESE-1 can bind to such polypeptide. This method comprises contacting a mammalian cell which expresses an ESE-1 with the ligand under conditions permitting binding of ligands to the ESE-1, and detecting the presence of a ligand which binds to the polypeptide thereby determining whether the ligand binds to the ESE-1. The systems hereinabove described for determining agonists and/or antagonists may also be employed for determining ligands which bind to the ESE-1.

The compounds of to be tested include small molecules, peptides, antisense RNA or viral DNA. Examples of potential ESE-1 polypeptide antagonists include antibodies or, in some cases, oligonucleotides which bind to the polypeptide but do not elicit a response, e.g., inflammatory response, such that the activity of the polypeptide is prevented.

Potential antagonists also include proteins which are closely related to ESE-1, i.e. a fragment of ESE-1, or a mutated ESE-1 which have lost biological function or acts as a dominant negative and, when binding to ESE-1 target genes or to ESE-1 interacting proteins, elicit no response or compete with wild type ESE-1.

A potential antagonist also includes an antisense construct prepared through the use of antisense technology. ESE-1 gene regulation can be downregulated or entirely inhibited by the use of antisense molecules. An "antisense sequence" or "antisense nucleic acid" is a nucleic acid is complementary to the coding ESE-1 mRNA nucleic acid sequence or a subsequence thereof.

Binding of the antisense molecule to the ESE-1 mRNA interferes with normal translation of the ESE-1 polypeptide.

Examples of antisense molecules that can be used in the present invention include oligonucleotides and oligonucleotide analogs that are hybridizable with ESE-1 messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of ESE-1 polypeptides.

Another potential antagonist is a small molecule, which binds to the ESE-1 polypeptide, making it inaccessible to ligands such that normal biological activity is prevented. Examples of small molecules include, but are not limited to, small peptides or peptide-like molecules, and non-peptide molecules.

It was found that a mutated version of an ESE-1 construct can act as a "dominant-negative" transcription factor to silence ESE-1 regulated genes, e.g., the COX-2 promoter and NOS2 promoter in response to endotoxin (see Examples 1M and 2H below). Using the information provided herein and known in the art ESE-1 polypeptide variants can be routinely produced. Methods of making other such polypeptide variants or muteins are well known to those of skill. Screening of such polypeptides (e.g., in DNA binding assays or for competitive inhibition of full-length normal ESE-1 polypeptides) can be accomplished with only routine experimentation. Using high-throughput methods, as described herein, literally thousands of agents can be screened in only a day or two.

Alternatively, antagonists or agonists of the present invention may comprise molecules which activate or repress genes regulated by this transcription factor. Electrophoretic mobility shift assays where ESE-1 binding sites in promoters are used together with ESE-1 recombinant proteins can be used to identify genes regulated by ESE-1. Modulation of the expression of these genes by test compounds to identify potential antagonists and agonist can then be performed in accordance with the above described methods.

New chemical entities with useful properties are generated by identifying a chemical compound (called a "lead compound") with some desirable property or activity, creating variants of the lead compound, and evaluating the property and activity of those variant compounds. High throughput screening methods are replacing conventional lead compound identification methods because they enable quick and efficient testing of large numbers of compounds. In one example of a high throughput screening method, a library containing a large number of potential therapeutic compounds (candidate compounds) is used. These are termed "combinatorial chemical libraries" and can be screened using any of the methods described herein. The compounds thus identified can serve as conventional "lead compounds" or can themselves be used as potential or actual therapeutics. Preparation and screening of combinatorial chemical libraries is well known to those of skill in the art.

High throughput assays for the presence, absence, or quantification of particular nucleic acids or protein products are well known to those of skill in the art. Similarly, binding assays and reporter gene assays are similarly well known, as are high throughput screening methods for proteins, high throughput screening methods for nucleic acid binding (i.e., in arrays), and methods of screening for ligand/antibody binding. In addition, high throughput screening systems are commercially available Any of the assays for compounds modulating ESE-1 gene expression and/or ESE-1 protein activity described herein are amenable to high throughput screening. Preferred assays thus detect enhancement or inhibition of ESE-1 gene transcription, inhibition or enhancement of ESE-1 polypeptide expression, inhibition or enhancement of DNA binding by ESE-1 polypeptide inhibition or enhancement of protein interaction with ESE-1, inhibition or enhancement of ESE-1 phosphorylation or aceylation, inhibition or enhancement of ESE-1 nuclear 1 cytoplasmic translocation, or inhibition or enhancement of expression of native genes (or reporter genes) under control of the ESE-1 polypeptide.

Antagonists for ESE-1 may be employed for a variety of therapeutic and prophylactic purposes for such diseases or disorders as described herein.

Methods of Diagnosing Disease and Monitoring Treatment

The invention also relates to methods of diagnosing the presence of an inflammatory disease in a mammal. In one example of such a method, a sample of blood, tissue, synovial fluids urine or CSF or organ is removed from the mammal. The presence and/or amount of a transcription factor of interest, e.g., ESE-1 is then measured using methods known in the art, and described herein. The sample tested does not normally express the transcription factor of interest in detectable amounts in the absence of the inflammatory disease.

Examples of inflammatory diseases that can be diagnosed by the methods of the present invention include rheumatological or autoimmune diseases, atherosclerosis, restenosis, transplantation associated arteriopathy, psoriasis, for example. Examples of rheumatological or autoimmune disease include e.g., rheumatoid arthritis, osteoarthritis, vasculitis, sclereoderma, and systemic lupus erythematosus.

Similarly, the invention also provides methods of monitoring the treatment of an inflammatory disease. In one such methods, a sample is removed from the mammal subsequent to treatment and the presence or amount of a transcription factor is measured. Again, the transcription factor is not present in the sample in detectable amounts in the absence of the inflammatory disease. As above, the sample can be tissue, synovial fluid, blood, urine, CSF or an organ sample. This procedure can be repeated at subsequent intervals and the amounts of the transcription factor compared in order to monitor the effectiveness of the treatment over time.

Pharmaceutical Compositions

The present invention also relates to pharmaceutical compositions for the treatment of inflammation comprising a compound that alters or modulates the expression of a transcription factor and a pharmaceutically acceptable carrier. Preferred compositions comprise compounds that alter the expression or function of ESE-1. Examples of compounds that are useful in such compositions include small molecules, peptide, or antisense RNA. In certain embodiments, the composition further comprises an agent that stimulates cartilage repair, e.g., a cartilage-inducing growth/differentiation factor, with or without a collagen scaffold or synthetic polymer.

By pharmaceutically acceptable carrier, it is meant to include, but is not limited to, saline, buffered saline, dextrose, water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration of Compounds

Polypeptides and other compounds of the present invention may be employed alone or in conjunction with other compounds, such as therapeutic compounds.

The ESE-1 polypeptides, anti-ESE-1 antibodies, or other ESE-1 modulators of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the ESE-1 polypeptides and related compounds described of, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for localized administration to areas of inflammation, in particular, joints or inflamed tissues. In another embodiment, the compositions are useful for parenteral administration, such as intravenous administration or administration into a body cavity or lumen of an organ. The compositions for administration will commonly comprise a solution of the ESE-1 polypeptide, antibody, or agonist or antagonist dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compounds in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art.

The compositions containing the present ESE-1 polypeptides, antibodies or antibody, antagonists, or agonists, or a cocktail thereof (i.e., with other proteins), can be administered for therapeutic treatments. To treat inflammation characterized by over expression of ESE-1, one can administer an anti-ESE-1 antibody or an abnormal ESE-1 protein that is not biologically active, e.g., a dominant negative ESE-1 protein, such as ESE-1 DN1 or ESE-1 DN2. Such inactive ESE-1 polypeptides can, for example, interfere with binding of native ESE-1 polypeptide to its DNA binding site, or to RNA polymerase or other protein through which the ESE-1 transcription factor activity is mediated. The truncated dominant negative proteins can be tailored to be able to cross the cell membranes for administration to animals or humans. These proteins van be modified by methods known in the art, e.g., by adding a short peptide sequence to the amino or carboxy terminus of the proteins. Examples of such membrane permeable sequences and the methods for use are described in Zhang, L., et al., *Proc. Natl. Acad. Sci.*, Vol. 95, pp. 9184–9189 (August, 1998). Specific examples of such sequences include, e.g., AAVALLPAVL-LALLAKS (SEQ ID NO: 1) and VTVLAL-GALAGVGVGKS (SEQ ID NO: 2), but others are known in the art.

In therapeutic applications, compositions are administered to a patient suffering from a disease (e.g., an inflammatory disease) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of interest to effectively treat the patient. Among various uses of the ESE-1 polypeptides, polypeptide subsequences, anti-ESE-1 antibodies and small molecules, and are treatment a variety of inflammatory disease conditions, including rheumatoid arthritis, vascular inflammation, etc., as described above.

Gene Therapy

The ESE-1 polynucleotides, polypeptides, agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide may be engineered for expression in a replication defective retroviral vector. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Such vectors will include one or more promoters for expressing the polypeptide. The selection of a suitable promoter will be apparent to those skilled in the art from the teachings contained herein.

For example, to determine whether forced expression of wild type ESE-1 in the air pouch mouse model of inflammation could induce inflammation or dominant-negative ESE-1 could inhibit inflammation, it is desirable to be able to express ESE-1 in the majority of cells in particular inflammatory cells. We have, therefore, introduced the wild type and dominant negative mutant ESE-1 cDNAs into a retroviral vector (Cone, R. D., et al. 1987. Science 236:954–7; Scharfmann, R., et al. 1991. Proc Natl Acad Sci U S A 88:4626–30.). This vector can be introduced after packaging into a retrovirus. High titer amphotropic retroviruses can be produced to be used for infection. The retroviruses are a tool to infect various types of replicating cells in the airpouch with high efficiency. We have generated several replication-deficient adenoviral expression vectors for wild type and dominant-negative ESE-1 under the transcriptional control of the CMV promoter. cDNAs inserted into the pACCMV-pLpA shuttle vector were co-transfected together with the pJM 17 adenovirus backbone vector into 293 cells (Becker, T. C., et al., 1994. Methods Cell Biol 43:161–189; McGrory, W. J., et al. Virology 163:614–7.). Recombinant virions were isolated by a plaque assay (Becker, T. C., et al., 1994. Methods Cell Biol 43:161–189) and have been analyzed for correct recombination, high titer, and ability to express the recombinant proteins.

Adenoviral vectors can be used for gene therapy according to known methods in the art, including the following: Muruve D, Manfro R C, Strom T B, and Libermann T A. Ex vivo adenovirus-mediated gene delivery leads to long-term expression in pancreatic islet transplants. Transplantation; 1997; 64: 542–546; Muruve D A, Nicholson A G, Manfro R C, Strom T B, Sukhatme V P, and Libermann T A. Adenovirus mediated expression of FAS ligand induces hepatic apoptosis after systemic administration and apoptosis of ex vivo infected pancreatic islet allografts and isografts. Human Gene Ther.; 1997; 8: 953–965 and Sata M, Perlman H, Muruve D A, Silver M, Ikebe M, Libermann T A, Oettgen P, and Walsh K. Fas ligand gene transfer to the vessel wall inhibits neointima formation and overrides the adenovirus-mediated T cell response. 1998: Proc. Natl. Acad. Sci. USA; 95: 1213–1217.

A variety of adenoviral vectors have been generated which have been used in various in vivo gene therapy settings (Muruve D, M. R. C., et al., 1997. Transplantation 64:542–546; Muruve, D. A., et al., 1999. Hum Gene Ther 10:965–76; Muruve D A, N. A., et al., 1997. Human Gene Ther. 8:953–965; Sata M, P. H., et al., 1998. Proc. Natl. Acad. Sci. USA 95:1213–1217). We have used replication deficient adenovirus type 5, one of the most efficient vectors for transducing non-replicating and replicating eukaryotic cells, to transfer genes into murine pancreatic islets in an allogeneic organ transplant model as a tool to prevent allograft rejection. We have demonstrated that we can achieve long term gene expression in pancreatic islet transplants using adenovirus-mediated gene delivery. We also demonstrated that adenovirus mediated expression of FAS ligand induces hepatic apoptosis after systemic administration and apoptosis of ex vivo infected pancreatic islet allografts and isografts. We have used Fas ligand gene transfer to the vessel wall to inhibit restenosis after balloon angioplasty.

The present invention is further illustrated by the following Examples. The Examples are provided to aid in the understanding of the invention and are not construed as a limitation thereof.

Certain terms used herein are explained in the foregoing glossary. All examples are carried out using standard techniques, which are well known and routine to those of skill in the art, except where otherwise described in detail. Routine molecular biology techniques of the following examples can be carried out as described in standard laboratory manuals.

EXAMPLE 1

Role of ESE-1 in Vascular Inflammation

Experimental Prodedures

Cell Culture:

Primary human umbilical vein endothelial cells and primary human smooth muscle cells were obtained from Clonetics and grown according to the manufacturers recommendations. THP-1 (human monocyte line) and RAW(rat monocytic line) cells were grown in DMEM supplemented with 10% FCS. Rat aortic smooth muscle cells (RASMCs) were harvested from male Sprague-Dawley rats by enzymatic dissociation according to the method of Gunther et. al.(Gunther, 1982).

RNA Isolation and Northern Blot Analysis

Total RNA was isolated using the RNAeasy kit(Quiagen). Northern blots were hybridized with random prime labeled, ESE-1, and GAPDH cDNA in QuickHyb solution (Stratagene) according to the manufacturers recommendations and washed at 50° C. with 0.2×SSC, 0.2% SDS.

RT/PCR Analysis:

CDNAs were generated from I jig mRNA isolated from different cells or tissues using oligo $dT_{12-18}$ priming (Gibco BRL Grand Island, N.Y. USA) and M-MLV reverse transcriptase (Gibco BRL) in deoxyribonuclease I (Gibco BRL) treated samples. Each PCR used equivalent amounts of 0.1 ng cDNA, 4 ng/ul of each primer, 0.25 units of Taq polymerase (Promega, Madison, Wis. USA), 150 uM of each dNTP, 3 mM of $Mgcl_2$, reaction buffer and water to a final volume of 25 ul and were covered with mineral oil.

The sequences of the ESE-1 primers were:
sense: 5'-CTGAGCAAAGAGTACTGGGACTGTC-3'. (SEQ ID NO: 3)
antisense: 5'-CCATAGTTGGGCCACAGCCTCGGAGC-3' (SEQ ID NO: 4)
with an expected amplification product of 188 bp.
The sequences of the primers for GAPDH were:
sense: 5'-CAAAGTTGTCATGGATGACC-3' (SEQ ID NO: 5)
antisense: 5'-CCATGGAGAAGGCTGGGG-3' (SEQ ID NO: 6)
with an expected amplification product of 200 bp.

RT/PCR amplifications were carried out using a Perkin-Elmer Cetus thermal cycler 480 as follows: 20–30 cycles of 1 min at 94° C., 1 min at 56° C. and 1 min at 72° C. followed by 15 min at 72° C. Lower numbers of cycles were used to verify linearity of the amplification signal. 10 µl of the amplification product was analyzed on a 2% agarose gel.

In vitro Transcription/translation

Full length cDNA encoding the whole open reading frame of p50 and p65 were inserted downstream of the T7 promoter into the pCRII TA cloning vector (InVitrogen). Coupled in vitro transcription/translation reactions were performed as previously described.

Electrophoretic mobility shift assays were performed as previously described(Dube, 1999). In brief, 2 µl in vitro translation product and 0.1–0.2 ng $^{32}$P-labeled doublestranded oligonucleotide probes (5000–20000 cpm) in the presence or absence of competitor oligonucleotides (1 and 10 ng) and run on 4% polyacrylamide gels, containing as buffer 0.5×TGE as described.

Oligonucleotides used as probes and for competition studies are as follows:
1) murine PSP promoter WT oligonucleotide

```
5'-TCGACGAACATCCAGGAAATAGGGCTC-3'     (SEQ ID NO: 7)

3'-GCTTGTAGGTCCTTTATCCCGAGAGCT-5'     (SEQ ID NO: 8)
```

2) INOS Ets site.

Expression Vector and Luciferase Reporter Gene Constructs

A 1516 and 265 bp fragment corresponding to nucleotides (−1485 to +31) and (−234 to +31) of the murine NOS2 gene promoter were subcloned into the PGL2 luciferase reporter (Promega).

Site Directed Mutagenesis:

DNA transfection assays:

Co-transfections of $2\times10^5$ RAW cells or RASMCs were carried out with 0.6 µg reporter gene construct DNA and 0.6 µg expression vector DNA using 6 µl lipofectamine (Gibco-BRL) as described (Oettgen, P., et al. 1996. Characterization of NERF, a novel transcription factor related to the Ets factor ELF-1. Mol Cell Biol 16:5091–106). The cells were harvested 16 hours after transfection and assayed for luciferase activity. Transfections for every construct were performed independently in duplicates and repeated 3 times with two different plasmid preparations with similar results. Cotransfection of a second plasmid for determination of transfection efficiency was omitted because potential artifacts with this technique have been reported and because many commonly used viral promoters contain potential binding sites for ets factors (Farr, A., and A. Roman. 1992. A pitfall of using a second plasmid to determine transfection efficiency. Nucleic Acids Res 20:920).

GST Pull-down Assay:

A series of GST-ESE-1 fusion proteins were generated by PCR with specific primers to contain in frame restriction enzyme sites and sequenced to confirm that there were no mutations introduced by the PCR. GST-ESE-1 fusion proteins were prepared as previously described. 35S-methionine labeled in vitro translated full-length p50 and p65 were incubated with equal amounts of GST-ESE-1 fusion proteins or GST on agarose beads in 200 ul of NETN(0.5% Nonidet P-40, 1 mM EDTA, 20 mM Tris-HCl, pH 8.0, 100 mM NaCl) for 3 h at 4 degrees C. with gentle shaking. Bound p50 or p65 proteins were then eluted after three washings with NETN buffer and analyzed on a 12% SDS-polyacrylamide gel.

The rat model of endotoxemia is as previously described (Pellacani, A., et al., 1999, J Biol Chem 274:1525–32). In brief, male Sprague-Dawley rats (200–250 g) were treated with either *Salmonella typhosa* LPS(10 mg/kg intraperitoneally) or control vehicle. Aortas will be harvested at 8 to 48 hours after injections and fixed and stained for ESE-1 and NOS-2 protein expression as described below.

Immunohistochemistry:

Using the models described above, the mice were euthanized at different time points and the blood vessels were perfusion fixed with 2% paraformaldehyde. Following fixation, the blood vessels will be paraffin embedded. 10 um sections will be digested with 0.02% protease XXIV (Sigma) for 6 minutes and incubated with a rabbit polyclonal anti-ESE-1 antibody. The primary antibody will be applied for 1 hour at room temperature, and then washed 3 times with PBS.

EXAMPLE 1A

ESE-1 is Lnducible in Response to Inflammatory Stimuli

We have previously shown that under basal conditions ESE-1 expression is restricted to cells of epithelial origin. To examine whether ESE-1 could be induced in nonepithelial cells, ESE-1 expression was evaluated in human aortic smooth muscle cells, human umbilical endothelial cells, and the human monocyte-macrophage cell line(RAW 264.7). As is shown in FIG. 1A ESE-1 expression is induced in response to the inflammatory cytokines interleukin-1 and TNF-α, and endotoxin. Interestingly, depending on the cell type, ESE-1 expression was induced as early as one hour in the RAW cells, to as late as four hours in the human aortic smooth muscle cells. In the HUVECs induction of expression is dependent on the stimulus. Whereas TNF-α stimulation led to early induction by 1–2 hours, IL-1 led to an induction of ESE-1 at 4 hours and peaked at 6 hours. In the primary cells ESE-1 expression was almost completely absent by 24 hours after stimulation, suggesting that ESE-1 expression in these cell types is strongly linked to stimulation by inflammatory stimuli. To confirm this, we performed Northern blot analysis of ESE-1 using total RNA derived from human aortic smooth muscle cells stimulated with interleukin-1 beta. As is shown in FIG. 1B, ESE-1 expression is absent prior to induction with IL-1β and expression peaks about 4 hours after stimulation.

EXAMPLE 1B

The ESE-1 Promoter is Inducible in Response to Inflammatory Cytokines

We have previously isolated and characterized the human ESE-1 promoter (Oettgen, P., et al. 1999. Genomic organization of the human ELF3 (ESE-1/ESX) gene, a member of the Ets transcription factor family, and identification of a functional promoter. Genomics 55:358–62). As is shown in FIG. 2, the ESE-1 promoter contains a putative NF-κB binding site, in addition to sites for other known transcription factors. To test whether the ESE-1 promoter was responsive to an inflammatory stimulus, the a luciferase reporter construct containing the ESE-1 promoter was transfected into RAW 264.7 cells. As is shown in FIG. 3, is the ESE-1 promoter is inducible to LPS in the RAW cells and a mutation in the NF-κB binding site significantly reduces this inducibility, suggesting that binding of NF-κB or related Rel proteins is required for inducible ESE-1 expression. The same results were obtained in the rat aortic smooth muscle cells (data not shown).

EXAMPLE 1C

ESE-1 Induction is NF-κB Mediated

Figure 4A:
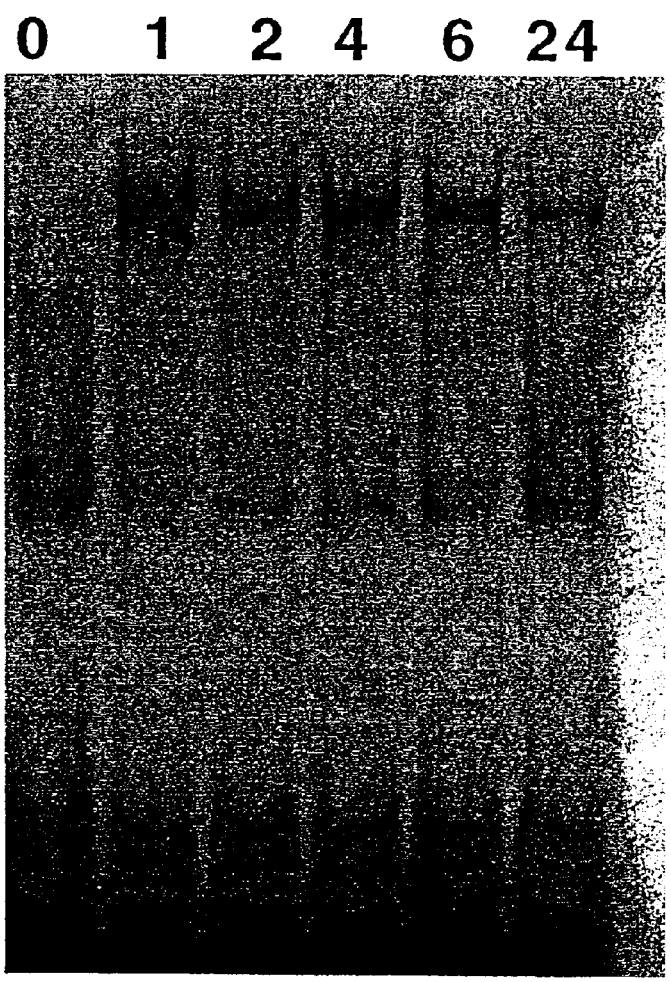
FIG. 4(A) shows EMSA using an oligonucleotide probe encoding the ESE-1 promoter NF-κB site, with whole cell extracts derived from human aortic smooth muscle cells at different time points (0,1,2,4,6,24 hours).
Figure 4B:
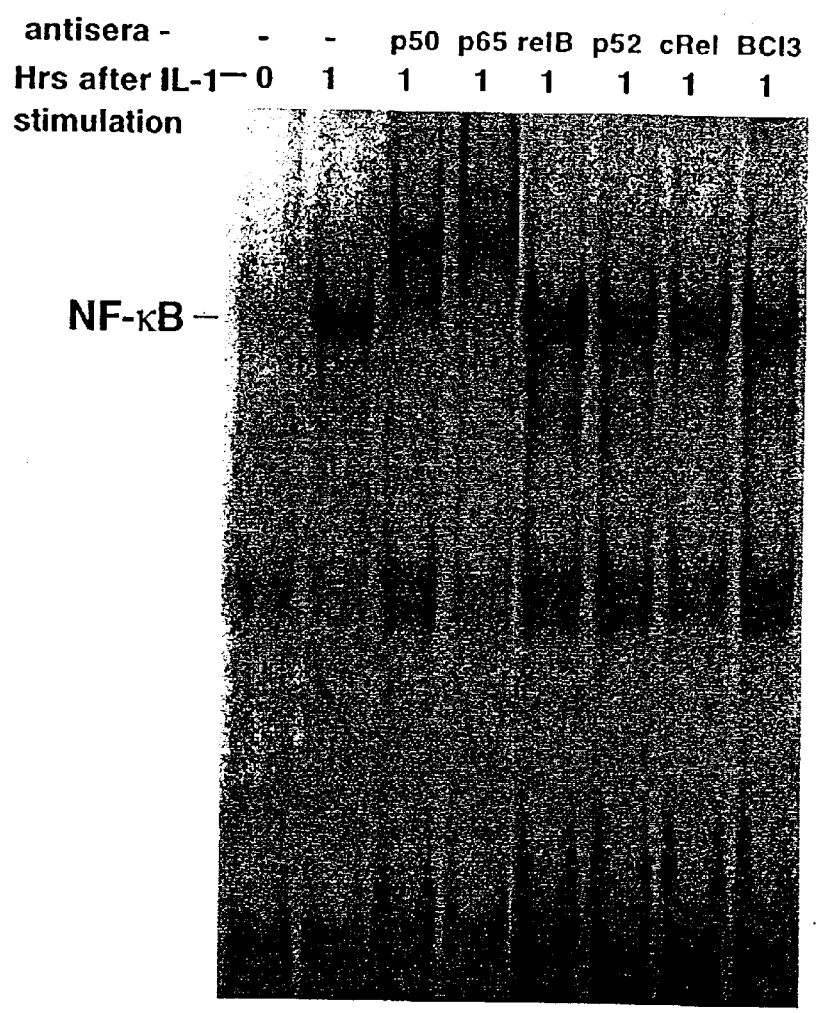
FIG. 4(B) shows EMSA using ESE-1 NF-κB oligonucleotide probe and whole cell extracts derived from IL-1 stimulated cell at 0 hours(control) or 1 hour, in the presence or absence of antibodies to the different Rel family members. An antibody to the unrelated Bcl-3 protein is used as a negative control.

To identify the specific proteins binding to the ESE-1 NF-κB site, electrophoretic mobility shift assays(EMSA) were performed using whole cell extracts derived from human aortic smooth muscle cells stimulated with IL-1β. As is shown in FIG. 4A, Il-1β stimulation is associated with an inducible change in binding pattern to the ESE-1 NF-κB binding site. Interestingly, this binding occurs as early as one hour, despite the fact that ESE-1 expression was only detected in Il-1β stimulated HASMCs at about 4 hours. To identify the proteins specifically binding to this site, EMSAs were performed in the presence or absence of antisera to the different Rel family members. As is shown in FIG. 4B, the only two proteins recognized in this complex are p50 and p65. This suggests that the induction of ESE-1 is mediated by inducible binding of the dimeric NF-κB proteins p50 and p65 to the ESE-1 promoter.

EXAMPLE 1D

NOS2 is a Potential Target Gene for ESE-1

In an attempt to identify target genes for ESE-1, the ability of ESE-1 to transactivate the promoters of several genes that are induced in response to inflammatory stimuli were tested. As is shown in FIG. 5A, ESE-1 significantly transactivates the NOS2 promoter but not E-selectin, CD44, or the interleukin-6 promoters. Transactivation of the ICAM-2 promoter by ESE-1 led to a 3.5 fold induction. The promoter of another gene, flt-1, which is known to be regulated by Ets factors, flt-1, but which is not induced in response to inflammatory cytokines was used as another control was mildly induced by ESE-1. The NOS2 gene promoter has two important regulatory regions, one that is upstream (−1100 to −800) and one that is in the more proximal promoter (−234 to +31). To test whether ESE-1 transactivation occurred principally through the upstream region or within the proximal promoter, cotransfections were performed with ESE-1 reporter constructs were tested encoding either a long fragment of the NOS2 promoter containing both regions, or containing just the proximal promoter. As is shown in FIG. 5B, transactivation was similar with both NOS2 promoter constructs suggesting that most of transactivation by ESE-1 occurs through the proximal promoter region.

EXAMPLE 1E

ESE-1 can Bind to an Ets Site within the NOS2 Promoter

Figure 6:
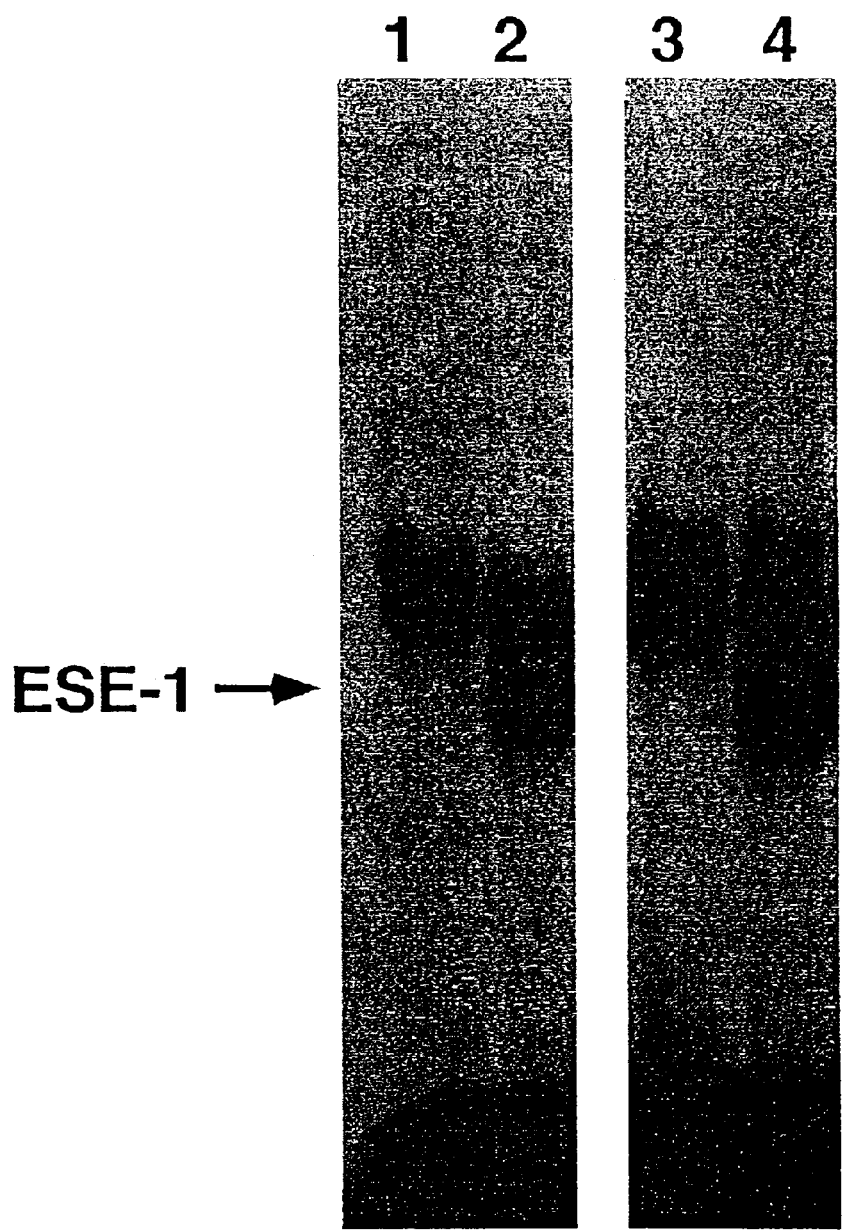
FIG. 6 shows Electrophoretic Mobility Shift Assay (EMSA) of in vitro translated ESE-1 with an oligonucleotide probe encoding either the PSP promoter Ets site(lane 2), or the NOS2 promoter Ets site(lane 4) compared with unprogrammed reticulocyte lysate control(lanes 1 and 3).

Having identified putative targets for ESE-1 we were also interested to determine whether ESE-1 could specifically bind to Ets sites within the NOS2 promoter. An Ets binding site was identified which is highly homologous to the Ets consensus binding site for ESE-1 (Oettgen, P., et al., 1999, J Biol Chem 274:29439–52). Using in vitro translated ESE-1 protein, EMSA was performed comparing the potential binding of ESE-1 to the NOS2 ets site compared to binding to an Ets site in the epithelial-specific PSP gene which has previously been shown to bind to ESE-1. As is shown in FIG. 6, ESE-1 binds equally well to both Ets sites.

EXAMPLE 1F

Mutational Analysis of the NOS2 Promoter Ets Site

To determine the functional importance of the NOS2 promoter ESE-1 binding site, site directed muatgenesis of this site, substituting "TTAA" for the core "GGAA" sequence was performed. Two independent constructs were verified by DNA sequencing. The effect of this mutation upon the ability of ESE-1 to transactivate the mutated NOS2 promoter was first examined. As is shown in FIG. 7A, this mutation completely abolished the ability of ESE-1 to transactivate the NOS2 promoter. The functional importance of this mutation was next evaluated in the context of induction with an inflammatory stimulus. As is shown in FIG. 7B, the same mutation led to a 60% reduction in inducibility of the promoter with LPS. This reduction is similar to that seen with mutation of the NF-κB or Oct sites(Perrella).

EXAMPLE 1G

ESE-1 Synergizes with p50 and p65 to Transactivate the NOS2 Promoter

Because p50 and p65 are also activated in response to inflammatory stimuli, we were interested to examine whether the interaction of the Rel domain proteins with ESE-1 had any functional effect upon transactivation. Cotransfection experiments with ESE-1, p50, and p65 were performed with the NOS2 and COX-2 promoters. As is shown in FIG. 8, p65 and ESE-1 had independent effects upon promoting the transactivation of the two promoters. Although combinations of ESE-1 and either the p50 or p65 proteins enhanced transactivation, there was a marked synergistic response with the combination of p50, p65, and ESE-1 for both promoters. Furthermore, this combined effect was substantially greater than with the combination of p50 and p65 alone. Thus, ESE-1 substantially augments the NF-κB mediated transcriptional response to inflammatory stimuli.

EXAMPLE 1H

ESE-1 Binding to Rel Domain Proteins

It has previously been shown that both Ets factors and HMG proteins are capable of binding to the Rel family members. Interestingly, the binding regions where these protein-protein interactions occur are within the DNA binding domain of both types of transcription factors. For the HMG(I)Y protein, this region of interaction has been precisely mapped within one of the A/T hook domains (Verdine). There is significant protein sequence homology between the A/T hook domain of ESE-1 and the region responsible for binding with p50 in the HMG(I)Y protein. Although the Ets domain is known to interact with p50, the precise region within this domain has not been determined. In order to identify whether ESE-1 can bind to either the p50 or p65 Rel domain proteins, 35S-methionine labeled p50 and p65 were generated by in vitro translation(See FIG. 9A). Several GST-ESE-1 fusion constructs and the GST protein alone were made. A diagram of the constructs is shown in FIG. 9C. As is shown in FIG. 9B, not only did the full length ESE-1 protein bind to p50, but both the A/T hook and the Ets domain were capable of interacting with p50. In contrast, there was no significant binding of any of the constructs to p65 (data not shown).

EXAMPLE 1I

ESE-1 is Induced in Acute Vascular Inflammation

To examine the vascular expression of ESE-1 in response to an inflammatory stimulus, ESE-1 expression was evaluated by immunohistochemical analysis in a rat model of endotoxemia in which marked vascular inflammation occurs within hours of endotoxin administration. As is shown in Figure, ESE-1 expression was markedly induced 24 hours after exposure to endotoxin. Intense expression of ESE-1 is shown in the vascular endothelium and first layer of the vascular smooth muscle cells. Some expression is also evident in some of the other layers of vascular smooth muscle cells. In contrast, minimal to no ESE-1 expression was observed in the rat aorta at baseline. These studies confirm the inducibility of ESE-1 in response to inflammatory stimuli, in vivo as well as in vitro.

EXAMPLE 1M

Inhibition of ESE-1 by Dominant Negative Protein

A cDNA encoding a mutated ESE-1 protein was made by excising a fragment encoding amino acids 26 through 192, leaving the remainder of the encoded cDNA intact (see FIG. 21A). This cDNA was incorporated into the mammalian expression plasmid PCI (Promega) to produce the dominant negative protein (ESE-1 DN1)(See FIG. 22A).

The ability of ESE-1 DN 1 to block transactivation of the NOS2 promoter was tested in RAW cells. Cotransfection of ESE-1 with the NOS2 promoter led to an approximate 12-fold increase in transactivation. This was blocked by 60–70% when ESE-1 DN1 was cotransfected with ESE-1. (See FIG. 21B).

NOS2 is one of the main targets of ESE-1, and is rapidly induced in RAW cells in response to endotoxin (LPS), resulting in an approximate 14-fold increase in promoter activity. Cotransfection of ESE-1 DN1 with the promoter prior to LPS induction leads to slight reduction of basal promoter activity. In the presence of LPS, the ESE-1 DN1 protein blocked induction of the NOS2 promoter by LPS by approximately 70–75%. (See FIG. 21C).

Dominant-negative forms of ESE-1 may provide novel therapeutic compounds for blocking the induction of genes that are upregulated during inflammation. FIG. 22B shows another dominant negative protein of ESE-1, ESE-1 DN2.

EXAMPLE 2

Role of ESE-1 in Inflammation in Nonepithelial Cells Material and Methods

Cell Culture and Patient Ssamples

U-87 Mg and U-138 Mg (human glioma), THP-1 (human monocytic), RAW 264.7 (murine monocytic), LB-12 (human osteoblast-like large T antigen transformed bone marrow stromal cells), and human chondrocytes were grown and treated with cytokines as described (Apperley, J., et al. 1990. J Bone Mineral Res. 5:S93; Goldring, M. B., et al. 1994. J Clin Invest 94:2307–16; Goldring, S. R., et al. 1983. J Bone Joint Surg 65:575–84; Libermann, T. A., et al. 1987. Embo J. 6:1627–1632).

Tissues from patients with rheumatoid arthritis (RA) were obtained as discarded materials from total joint replacement surgery or synovectomy. RA synovial tissue samples were cultured for the generation of adherent synovial fibroblasts. Dispersed synovial tissues were prepared by a previously published method (Goldring, S. R., et al. 1983. The synovial-like membrane at the bone-cement interface in loose total hip replacements and its proposed role in bone lysis. J Bone Joint Surg 65:575–84). Cells were subjected to 2–4 passages and stimulated with IL-1β (R&D Systems) at 100 pg/ml or with TNF-α (R&D Systems) at 5 ng/ml.

Northern Blot and RT-PCR Analysis

Total RNA was harvested using QIAshreder (Qiagen) and RNeasy® Mini Kit (Quiagen) or Trizol (Gibco BRL). Poly A+ RNA was prepared with MicroPoly(A) Pure (Ambion). Northern blots (5 μg total RNA) were hybridized using a full length ESE-1 cDNA probe as described (Oettgen, P., et al. et al. 1997, Mol Cell Biol 17:4419–33.).

cDNAs were generated from 1 μg of total RNA using Ready-To-Go™ You-prime First-Strand Beads (Amersham Pharmacia Biotech Inc). RT-PCR amplifications of 0.1 μg cDNA were carried out using a MJResearch thermal cycler PTC-100 as follows: 5 min at 94° C., 20–37 cycles of 30 sec at 94° C., 30 sec at 56° C., and 30 sec at 72° C., followed by 5 min at 72° C. (Oettgen, P., et al. 2000, J Biol Chem 275:1216–25). The sequences of the human ESE-1 primers and the primers for human GAPDH were as described (Oettgen, P., et al. 1999, J Biol Chem 274:29439–52).

Expression Vector and Luciferase Reporter Gene Constructs

Full-length and dominant-negative mutant ESE-1 cDNAs were inserted into the pCI (Promega) eukaryotic expression vector as described (Oettgen, P., et al. et al. 1997, Mol Cell Biol 17:4419–33). The human COX-2 promoter spanning −170 to +103, kindly provided by Dr. Leslie J. Crofford, University of Michigan, (14) was cloned into the pXP2 luciferase vector (pXP2/COX-2).

Electrophoretic Mobility Shift Assays (EMSA)

In vitro transcription-translation was performed in TNT rabbit reticulocyte lysate (Promega) using the pCI/ESE-1 vector as described (Oettgen, P., et al. et al. 1997, Mol Cell Biol 17:4419–33). EMSAs and supershift assays were performed using 2 μl of in vitro translation product or 3 μl of whole cell extract and ($^{32}$P)-labeled double stranded oligonucleotide probes in the presence or absence of competitor oligonucleotides (1, 10 or 100 ng) or antibodies as described (Akbarali, Y., et al. 1996. J Biol Chem 271:26007–12). Whole cell extracts were made from U-138 Mg cells after incubation with IL-1β for 0, 3, and 8 hours using as lysis buffer 1% Triton X-100, 25 mM glycylglycine pH7.8, 15 mM MgSO$_4$, 4 mM EGTA, 1 mM dithiothreitol, phenylmethylsulfonyl fluoride, Aprotinin, and Pepstatin. All antibodies for super-shift assays (2 μl per assay) were obtained from Santa-Cruz Technologies (CA) (Oettgen, P., et al. 1996, Mol Cell Biol 16:5091–106).

Oligonucleotides used as probes and for competition studies are:

```
1) ESE-1 promoter wild type NF-kB:
5'-AGGCCAGGAAATCCCCTCCATC-3'        (SEQ ID NO: 9)
3'-TCCGGTCCTTTAGGGGAGGTAG-5'

2) ESE-1 promoter mutant NF-kB:
5'-AGGCCAGGAAATCGGATCCATC-3'        (SEQ ID NO: 10)
3'-TCCGGTCCTTTAGCCTAGGTAG-5'

3) IL-6 promoter NF-kB:
5'-TCGACATGTGGGATTTTCCCATGAC-3'     (SEQ ID NO: 11)
3'-AGCTGTACACCCTAAAAGGGTACTG-5'

4) COX-2 promoter Ets site #1:
5'-GCACGTCCAGGAACTCCTCAGC-3'        (SEQ ID NO: 12)
3'-CGTGCAGGTCCTTGAGGAGTCG-5'

5) COX-2 promoter Ets site #2:
5'-GAGAGAACCTTCCTTTTTATAA-3'        (SEQ ID NO: 13)
3'-CTCTCTTGGAAGGAAAAATATT-5'

6) COX-2 promoter Ets site #3:
5'- CGAAAAGGCGGAAAGAAACAGT-3'       (SEQ ID NO: 14)
3'-GCTTTTCCGCCTTTCTTTGTCA-5'

7) COX-2 promoter Ets site #4:
5'-GAGAGGAGGGAAAAATTTGTGG-3'        (SEQ ID NO: 15)
3'-CTCTCCTCCCTTTTTAAACACC-5'

8) COX-2 promoter Ets site #5:
5'-TCTCATTTCCGTGGGTAAAAA-3'         (SEQ ID NO: 16)
3'-AGAGTAAAGGCACCCATTTTT-5'
```

Mutations in the ESE-1 promoter NF-κB site and different CQX-2 promoter ETS sites were generated by site-directed mutagenesis with the QuikChange Site-directed Mutagenesis kit (Stratagene) and confirmed by sequencing. The following primer sets were used:

```
1) ESE-1 promoter NF-kB site:       (SEQ ID NO: 17)
5'-CTAAAGGCCAGGAAATCGGATCCATCCAATGAGACAC-3'

2) COX-2 promoter Ets site #1:      (SEQ ID NO: 18)
5'-GCTGAGGAGTAGCTGGACGTGCTCCTGAC-3'

3) COX-2 promoter Ets site #2:      (SEQ ID NO: 19)
5'-CAGTCTTATAAAAACCAAGGTTCTCTCGGTTAGCGACC-3'

4) COX-2 promoter Ets site #3:      (SEQ ID NO: 20)
5'-GACGAAATGACTGTTTCTTTGAGCCTTTTCGTACCCC-3'

5) COX-2 promoter Ets site #5:      (SEQ ID NO: 21)
5'-GGGTTTTTTACCCACGCTAATGAGAAAATCGGAAACC-3'
```

DNA Transfection Assays

Cotransfections of 3–8×10$^5$ cells were carried out with 600 ng reporter gene construct DNA and 200 ng expression vector DNA using LipofectAMINE PLUS (Gibco-BRL) for 16 hours as described (Oettgen, P., et al. et al., 1997, Mol Cell Biol 17:4419–33). Transfections were performed independently in duplicate and repeated 3 to 4 times with different plasmid preparations with similar results.

Adenovirus Infection

U-138 MG cells were infected with the IκB adenovirus (kindly provided by Fionula Brennan) (Bondeson, J., et al. 1999, Proc Natl Acad Sci U S A 96:5668–73) for 1 hour in serum-free medium using a multiple of infection of 1000. After infection the cells were washed with medium and incubated for 16 hours in DMEM containing 10% fetal calf serum in the absence or presence of IL-1β.

EXAMPLE 2A

ESE-1 is Induced by IL-1B, TNF-α and LPS in Non-epithelial Cells

Figure 11:
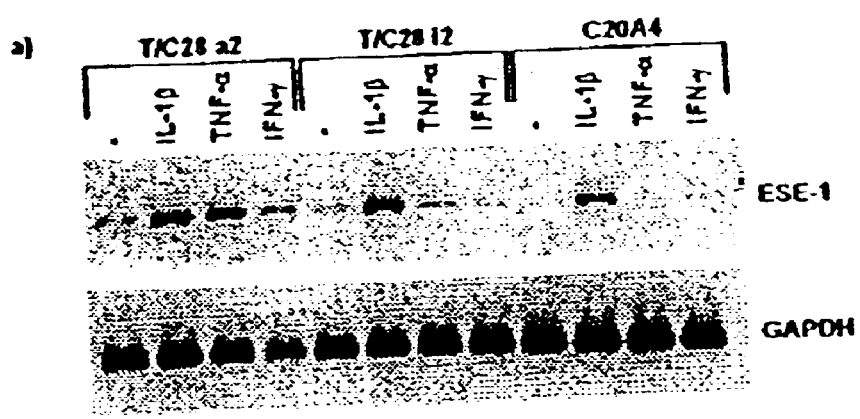
FIG. 11 shows induction of ESE-1 mRNA in patients with rheumatoid arthritis and PVNS and in non-epithelial cells by inflammatory stimuli.
Figure 11:
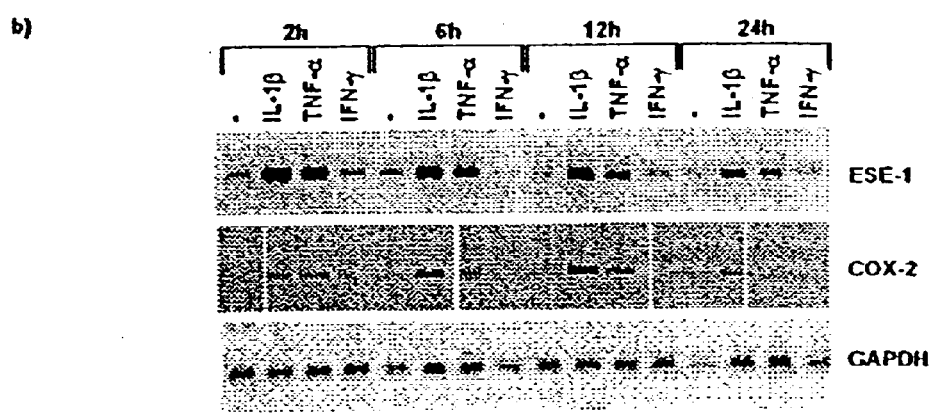
Figure 11:
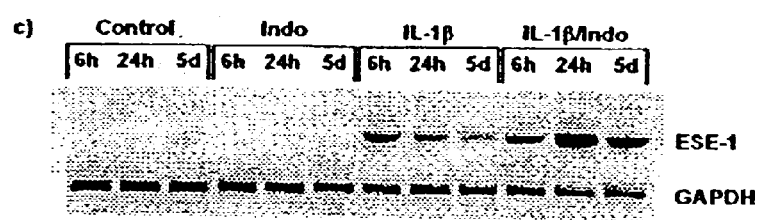
Figure 11:
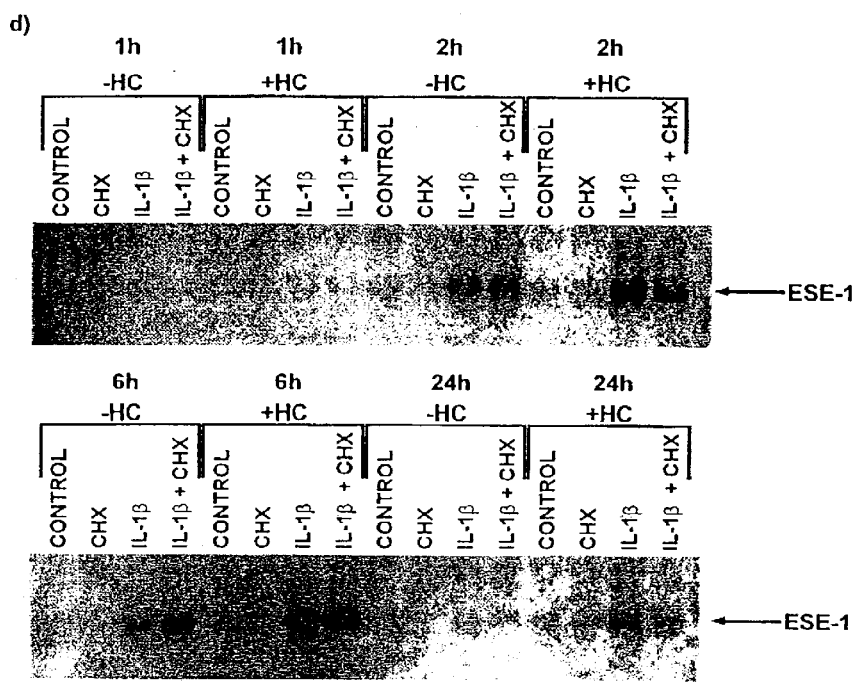
Figure 11:
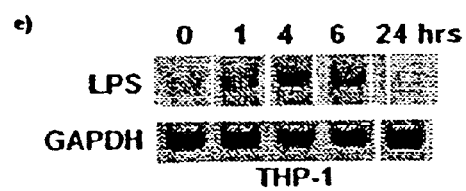
Figure 11:
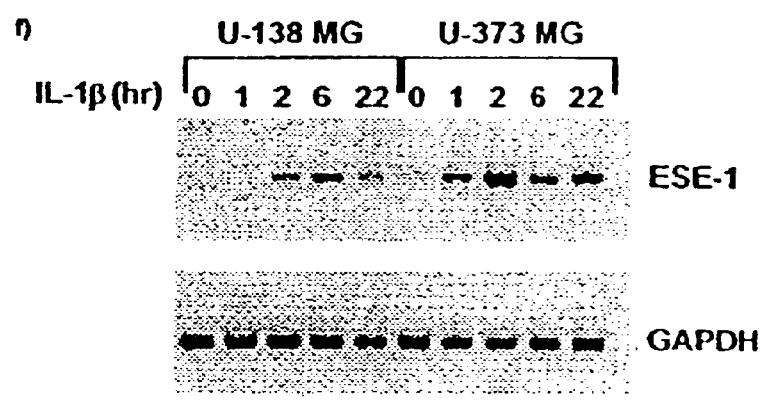

Previous reports had indicated that under normal physiological conditions ESE-1 expression is restricted to epithelial cells and that expression of ESE-1 in epithelial cells is under the control of growth and differentiation factors (Andreoli, J. M., et al. 1997. Nucleic Acids Res 25:4287–95; Chang, C. H., et al. 1997. Oncogene 14:1617–22; Oettgen, P., et al. et al. 1997. Mol Cell Biol 17:4419–33). To test the hypothesis that ESE-1 is a mediator of cytokine responses in non-epithelial cell types, we analyzed ESE-1 expression in response to a variety of cytokines in several connective tissue cell types. Immortalized human chondrocytes, T/C28a2, C28/I2, and C20/A4 (Goldring, M. B., et al. 1994, J Clin Invest 94:2307–16), were stimulated with IL-1β, TNF-α and IFN-γ for 24 hours. IL-1β induced ESE-1 expression in all chondrocyte cell lines (FIG. 11a). TNF-α stimulated ESE-1 expression in T/ C28a2 cells to similar levels as IL-1β, but only weakly in C28/I2 and C20/A4 cells. IFN-γ failed to induce ESE-1 expression, indicating that some, but not all proinflammatory cytokines are capable of inducing ESE-1 expression (FIG. 11a). The kinetics of ESE-1 induction was explored in a time course experiment with T/ C28a2 chondrocytes. RT/PCR analysis revealed rapid induction of ESE-1 mRNA by both IL-1β and TNF-α reaching a peak within two hours and declining gradually thereafter (FIG. 11b).

The synovium in RA is comprised of heterogeneous cell populations including monocyte/macrophages, lymphocytes and synovial fibroblasts. To evaluate whether ESE-1 expression in synovial fibroblasts is regulated by proinflammatory cytokines, 4th passage synovial fibroblasts isolated from RA synovium were stimulated for different times with IL-1β in the absence or presence of indomethacin. RT/PCR analysis revealed that unstimulated or indomethacin-treated cells did not express detectable ESE-1 mRNA (FIG. 11c); however, IL-1β strongly induced transient ESE-1 expression in synovial fibroblasts within 6 hours (FIG. 11c) which declined after 24 hours and was very low after 5 days. In the presence of indomethacin, which inhibits basal or IL-1-induced prostaglandin synthesis (Goldring, M. B. 1987, J Rheumatol 14:64–6), IL-1β-induced ESE-1 mRNA levels were stabilized and did not decline even after 5 days. These results demonstrate that IL-1β induces transient expression of ESE-1 in non-epithelial cells and implicate ESE-1 in cytokine-mediated responses. They also indicate that cytokine-induced prostaglandins may modulate steady state ESE-1 mRNA levels. Unlike chondrocytes TNF-α produced minimal ESE-1 induction in synovial fibroblasts (data not shown). We, therefore, focused our attention in further studies on IL-1β.

Osteoblasts, the bone cells responsible for bone formation, represent another connective tissue cell target of inflammatory cytokines in joint disorders (Bogoch, E. R., and E. Moran. 1998, Can J Surg 41:264–71). We have previously characterized an immortalized osteoblast-like bone marrow stromal cell line, LB-12, and showed that these cells exhibit an osteoblastic phenotype Goldring, S. R., et al. 1983 J Bone Joint Surg 65:575–84). LB-12 cells were incubated for different times in the absence or presence of IL-1β. Northern blot analysis demonstrated that ESE-1 was not expressed in unstimulated LB-12 cells, but was rapidly induced by IL-1β with a peak between 2 to 6 hours, and rapidly declined by 24 hours after stimulation (FIG. 11d). Since the rapid, but transient induction of ESE-1 resembles that of immediate early genes, we tested the effect of the protein synthesis inhibitor cycloheximide which superinduces expression of certain genes due to mRNA stabilization. Cycloheximide alone had no effect, but superinduced IL-1β-mediated ESE-1 mRNA expression (FIG. 11d). Hydrocortisone, which enhances the osteoblast phenotype in these cells, by itself did not induce ESE-1 mRNA, but strongly enhanced IL-1β-induced expression (FIG. 11d) (Kassem, M., et al. 1996, J Bone Miner Res 11:193–9).

Macrophages represent an additional cell type present within RA synovial tissues and are a major target of bacterial endotoxin. We, therefore, examined the effects of lipopolysaccharide (LPS) on ESE-1 expression in monocytes using the human monocytic cell line, THP-1 (FIG. 11e). Within one hour LPS induced ESE-1 expression, thus indicating that endotoxins are inducers of ESE-1 and that monocytes are able to express ESE-1 upon activation by proinflammatory stimuli (FIG. 11e).

In addition to their role in joint diseases, TNF-α and IL-1β have been shown to be important regulators of inflammatory processes that affect the central nervous system (Lee, S. C., et al. 1995, Brain Behav Immun 9:345–54). We, therefore, examined the effects of IL-1β on ESE-1 expression in human cells of glial origin. IL-1β rapidly induced transient expression of ESE-1 in the U-138 MG and U-373 MG glioma cells (FIG. 11f). IL-1β-mediated ESE-1 induction was highly specific for this member of the Ets family, since screening with a panel of Ets factors in IL-1β-stimulated U-138 MG cells revealed that ESE-2, PDEF, GABP-□, Tel, ERP, ELK-1, SAP-1, ELF-1, NERF, MEF, ERF, E4TF160, E1-AF, Fli-1, Erg, and Erm mRNAs were not induced by IL-1β at any time point (data not shown). Only Ets-1 was weakly upregulated by IL-1β (data not shown).

EXAMPLE 2B

The ESE-1 Promoter is Inducible by IL-1β and LPS

To investigate the molecular mechanism by which IL-1 β and LPS regulate ESE-1 expression, we examined the response of an ESE-1 promoter luciferase construct after transfection using two cytokine responsive non-epithelial cell types, U-138 MG human glial cells and RAW 264.7 cells, a murine macrophage cell line (Oettgen, P., et al. 1999, Genomics 55:358–62). Whereas the parental pXP2 vector was not stimulated by IL-1β, in U-138 MG cells, IL-1β increased ESE-1 promoter activity up to 5-fold (FIG. 12a). Similarly, LPS enhanced ESE-1 promoter activity ~9-fold in RAW 264.7 cells (FIG. 12b).

EXAMPLE 2C

IL-1β Induces the ESE-1 Promoter via Binding of the NF-κB Family Members p50 and p65 to a High Affinity Site Within the ESE-1 Promoter NF-κB has been shown to be a critical regulatory molecule involved in transducing cell responses to IL-1β and endotoxin. Using EMSA we compared the ability of the highly conserved human ESE-1 promoter NF-κB site (ESE-1/NF-κB), previously identified by us between nucleotides −79 and −88 upstream of the transcription start site (Oettgen, P., et al. 1999, Genomics 55:358–62), and the well characterized IL-6 promoter NF-κB site (IL6/NF-κB) (Libermann, T. A., and D. Baltimore. 1990, Mol Cell Biol 10:2327–34) to form complexes with proteins present in whole cell extracts from unstimulated and IL-1β-stimulated U-138 MG cells (FIG. 12c). Using the ESE-1/NF-κB probe we observed an inducible, high affinity protein-DNA complex in IL-1β-treated, but not unstimulated U-138 MG extracts, that comigrated with a complex formed by the IL6/NF-κB site (FIG. 12c). Competition with either wild type or mutant ESE-1/NF-κB oligonucleotides confirmed the specificity of the inducible complex (FIG. 12c). Using an EMSA supershift assay we determined that antibodies against the NF-κB/rel family members p50 and p65, but not other family members, completely shifted the inducible complex formed using extracts from the IL-1β stimulated U-138 MG cells (FIG. 12d).

EXAMPLE 2D

Inducibility of the ESE-1 Promoter by IL-1β is Mediated via the NF-κB Site

To examine whether the NF-κB site was responsible for IL-1-mediated activation of the ESE-1 gene, we introduced a mutation into the ESE-1/NF-κB site (FIG. 12e). U-138 MG cells transfected with wild type or mutant ESE-1 promoter/luciferase plasmids were incubated in the absence or presence of IL-1β. In contrast to the wild type ESE-1 promoter, which was induced by IL-1β, inducibility of the mutant promoter was completely abolished (FIG. 12f). These results demonstrated that the inducibility of the ESE-1 gene by pro-inflammatory stimuli such as IL-1β may be explained by activation of NF-κB.

EXAMPLE 2E

Inhibition of NF-κB Activation by an Adenovirus expressing IκB Blocks IL-1β Mediated Induction of Endogenous ESE-1 Expression To support the hypothesis that NF-κB may be required for IL-1β-mediated induction of endogenous ESE-1 gene expression, we tested the effect of blocking NF-κB activation by overexpressing IκB. U-138 MG cells were infected with either an adenovirus expressing the IκB inhibitor (Bondeson, J., et al. 2000, J Rheumatol 27:2078–89) or, as a control, an adenovirus expressing β-galactosidase and subsequently stimulated with IL-1β. The IκB adenovirus drastically reduced ESE-1 induction by IL-1β, although some residual ESE-1 transcript was detectable (FIG. 12g). These data confirmed NF-κB activation as a critical step involved in ESE-1 induction by IL-1β, although additional factors may contribute to ESE-1 induction.

EXAMPLE 2F

ESE-1 Enhances Transactivation of the COX-2 Promoter

We were interested to know which genes that are associated with inflammatory responses are targeted by ESE-1. We focused on the COX-2 gene, an important target for IL-1β, TNF-α, and LPS in inflammation. Furthermore, the COX-2 promoter contains multiple putative Ets binding sites that are potential targets for ESE-1. A COX-2 promoter luciferase construct, pXP2/COX-2, was transfected into RAW 264.7 cells in the absence or presence of the ESE-1 expression vector, pCI/ESE-1. ESE-1 enhanced COX-2 promoter activity more than 10-fold (FIG. 13a). As a positive control, cells were stimulated with LPS, which resulted in a more than 20-fold induction of the COX-2 promoter (FIG. 13a).

EXAMPLE 2G

Mutation of multiple ESE-1 Binding Sites Drastically Reduces Activation of the COX-2 Promoter by ESE-1 and by LPS To examine whether the putative Ets sites in the COX-2 promoter were responsive to ESE-1 and whether they mediated LPS induction of the COX-2 promoter, we introduced mutations into individual or multiple Ets sites simultaneously within the context of the COX-2 promoter (FIG. 13b). Transfection into RAW 264.7 cells in the absence or presence of LPS or pCI/ESE-1 indicated that mutation of any individual Ets site did not significantly affect ESE-1-mediated transactivation of the COX-2 promoter (data not shown). Combined mutations of two sites, 2 and 3, showed only a partial effect resulting in a 50% decrease in inducibility (FIG. 13c). Simultaneous mutation of sites 1, 2, 3, and 5 almost completely eliminated inducibility by ESE-1 suggesting that ESE-1 acts on the COX-2 promoter via multiple Ets sites (FIG. 13c). EMSA analysis with in vitro translated ESE-1 and oligonucleotides encoding all five COX-2 promoter Ets sites confirmed that sites 1 and 3 form a strong specific protein/DNA complex with ESE-1, whereas sites 2 and 5 form only weak complexes (data not shown). Mutation of the Ets binding sites 1, 2, 3, and 5 also drastically reduced LPS-mediated induction by almost 70% (FIG. 13d) indicating that LPS-mediated activation of the COX-2 promoter is partially dependent on ESE-1 expression.

EXAMPLE 2H

A dominant-negative ESE-1 Mutant Inhibits LPS Mediated Activation of the COX-2 Promoter RAW 264.7 cells were cotransfected with pXP2/COX-2 and a dominant-negative mutant of ESE-1 and stimulated with LPS. The mutant ESE-1 contains the Ets DNA binding domain, but lacks the transactivation domain and, therefore, can bind, but not transactivate ESE-1-dependent promoters. Dominant-negative ESE-1 completely eliminated LPS-mediated induction of the COX-2 promoter, further confirming the involvement of ESE-1 in LPS-mediated activation of the COX-2 promoter (FIG. 13e) (See Grall, F. T., et al., "Regulation Of The Inducible COX-2 Gene In Monocytic Cells By The Ets Transcription Factor ESE-1", J. Biol. Chem., (2003) (in press).

To further demonstrate the involvement of ESE-1 in COX-2 regulation, the osteosarcoma derived MG-63 cell line was used. This cell line has measurable endogenous COX-2 expression. COX-2 mRNA levels were assessed by real-time quantitative PCR following transfection with the dominant negative form of ESE-1 or its parental vector. A decrease of around 50% in the expression of COX-2 in the presence of dominant-negative ESE-1 was observed.

EXAMPLE 3

In Vivo Expression of ESE-1 in Animal Models of Vascular Inflammation

The biological role of ESE-1 in vascular inflammation is examined in three models of vascular inflammation. Preliminary studies demonstrated that the ESE-1 protein is strongly expressed in vascular endothelium and vascular smooth muscle cells within 24 hours in an acute model of vascular inflammation where rats have been injected with endotoxin.

The second model, a more chronic model of vascular inflammation, is the ApoE knockout mouse, in which animals develop accelerated atherosclerosis over several weeks to months.

Finally, as more subacute form of vascular injury, a model of transplantation arteriopathy is examined. NOS2 gene expression has been shown to be upregulated in all of these forms of vascular inflammation. Colocalization of ESE-1 expression with NOS2 and other identified ESE-1 target genes is also examined. The results of these experiments will help to define the biological role of ESE-1 in different types of inflammation by establishing the temporal relationship and colocalization of ESE-1 expression with the ESE-1 target genes associated with inflammation.

Animal Models of Vascular Inflammation:

EXAMPLE 3A

Rat Model of Endotoxemia

The rat model of endotoxemia is as previously described (Pellacani, A., et al. 1999, J Biol Chem 274:1525–32). In brief, male Sprague-Dawley rats (200–250 g) are treated with either *Salmonella typhosa* LPS(10 mg/kg intraperitoneally) or control vehicle. Aortas are harvested at 8, 24, and 48 hours after injections and fixed in 4% paraformaldehyde. After they are embedded in paraffin, serial sections are stained for ESE-1 and NOS2 protein expression as described below.

EXAMPLE 3B

ApoE –/–Mouse Model of Atherosclerosis

Male apoE –/– mice(Jackson Labs) are fed a 0.15% cholesterol diet(Western type No. 88137 Teklad). Monocyte adherence to endothelial cells in lesion prone areas of the aorta begin about 6 to 8 weeks of age. By 12 weeks fatty-streak lesions are apparent, and by 20 weeks of age many lesions progress beyond the fatty-streak stage and develop into fibro-proliferative intermediate lesions containing smooth muscle cells and abundant extracellular matrix, forming a cap over the foam-cell core. (Breslow, J. L. 1996, Science 272:685–8; Smith, J. D., and J. L. Breslow. 1997, J Intern Med 242:99–109). These lesions are often large and have necrotic regions in their core. Animals are euthanized at different time points after initiation of the model and evaluated for ESE-1 and NOS2 protein expression as shown below.

EXAMPLE 3C

Vascular Transplantation Model

The vascular transplant model is as previously described (Shi, C., et al. 1994, Circ Res 75:199–207). In brief, a portion of the left carotid artery is dissected out of donor mice(B10A(2R)(H-$2^{h2}$). This artery segment is transplanted paratopically as an end to side anastomosis to a carotid artery in the recipient(C57BL/6J (H-2b), such that blood flow through the artery segment is maintained. Grafts are harvested at serial time points after transplantation(2, 7, 15, and 30 days). Within 7 days of the transplantation, allografts form a neointima composed of mononuclear leukocytes. By thirty days there is a marked increase in size of the neointima where the mononuclear cells have largely been replaced by vascular smooth muscle cells (Shi, C., et al. 1994, Circ Res 75:199–207). In addition to a generalized inflammatory response this process also involves the activation of humoral and cellular immune mechanisms (Shi, C., et al. 1996. Immunologic basis of transplant-associated arteriosclerosis. Proc Natl Acad Sci U S A 93:4051–6).

EXAMPLE 3D

Immunohistochemistry

Using the models described above, the mice are euthanized at different time points and the blood vessels will be perfusion fixed with 4% paraformaldehyde. Following fixation, the blood vessels are paraffin embedded. Sections 4 μm in thickness will be mounted on glass slides. For single staining, either diaminobenzidine(DAB, brown color, DAKO), or immuno alkaline phosphatase(red color, Kierkegard and Perry) are used. After sections are washed in Tris buffered saline and blocked with 10–20% serum, sections are incubated for one hour or overnight at 4 degrees with the rabbit polyclonal anti-ESE-1 antibody as performed in the preliminary results, and then washed 3 times with PBS. A biotinylated goat anti-rabbit IgG antibody (Amersham), is used as the secondary antibody, and after serial washes is labeled with horseradish peroxidase(HRP)-conjugated streptavidin. To determine the timing and possible colocalization of expression of ESE-1 with NOS2 gene, the localization and timing of NOS2 protein expression is examined, as well as for other identified ESE-1 targets. For double staining, sections are incubated with the second primary antibody(e.g. NOS2 antibody, SantaCruz), followed by biotinylated secondary antibody and StreptABCmplex/AP(DAKO), followed by DAB (DAKO) and Fast Red(DAKO) chromogens respectively. Tissue sections are counterstained with Mayer's hematoxylin.

EXAMPLE 4

The Role of ESE-1 in Chronic Inflammation

Several animal models of inflammation have been successfully employed to study various aspects of inflammation and have been useful as screening tools for anti-inflammatory drugs. We have demonstrated that ESE-1 is rapidly induced in a rat endotoxemia model of inflammation.

The widely used rodent air pouch model of chronic inflammation fulfills all the criteria of a local inflammatory disease that can be easily manipulated (Dalhoff, A., G., et al., 1982. Infection 10:354–60; Ellis, L., V., et al., 2000. Ann Rheum Dis 59:303–7; Jackson, J. R., et al., 1998. J Pharmacol Exp Ther 284:687–92; Kimura, M., J., et al., 1985. J Pharmacobiodyn 8:393–400; Miller, A. J., et al.,. 1997. Br J Pharmacol 120:1274–9; Miller, A. J., et al.,1997. Am J Physiol 272:R857–61). This model provides a well-defined in vivo assay with which to quantify the systemic effects of compounds capable of altering the activity of ESE-1. This model is used in order to test that ESE-1 is a critical mediator of the inflammatory response. Results from this and the previous examples provide the basis for a rational drug design to interfere with ESE-1 function or induction in inflammatory diseases.

To evaluate the function of ESE-1 in inflammation the murine chronic granulomatous tissue air pouch model is used (Dalhoff, A., G., et al., 1982. Infection 10:354–60; Ellis, L., V., et al., 2000. Ann Rheum Dis 59:303–7; Jackson, J. R., et al., 1998. J Pharmacol Exp Ther 284:687–92; Kimura, M., J., et al., 1985. J Pharmacobiodyn 8:393–400; Miller, A. J., et al.,. 1997. Br J Pharmacol 120:1274–9; Miller, A. J., et al.,1997. Am J Physiol 272:R857–61.). The murine chronic granulomatous tissue air pouch model of chronic inflammation involves the subcutaneous injection of 3 ml sterile air into the dorsum of female Balb/C mice (20±2 g) followed 24 h later by the intrapouch injection of an inflammatory stimulus (0.5 ml of Freund's complete adjuvant containing 0.1% croton oil or 5 ng murine IL-1β) (Jackson, J. R., et al., 1998. J Pharmacol Exp Ther 284:687–92; Kimura, M., et al., 1985. J Pharmacobiodyn 8:393–400; Miller, A. J., et al.,1997. Am J Physiol 272:R857–61). Within 3 days, a cohesive granulomatous tissue encases the adjuvant mixture. Between days 5 to 7 the phenotype switches from an acute to a chronic inflammatory phenotype (Jackson et al., 1997). Moreover, at around day 14 there is another phenotypic change in the granuloma, when the chronic inflammatory phenotype gives way to a fibrotic phenotype (Jackson et al., 1997). 10 mice are used for each experimental condition in these and the following experiments. At different time intervals after the injection of the inflammatory stimulus into the air pouch, the mice are killed by cervical dislocation and the exudate in the pouch is collected with 1 ml of saline. In the inflammatory air pouch model, over the course of granuloma development up to 28 days, measure the cytokine profile (IL-6, IL-8, IL-1β and TNF-α etc.) and metalloproteinase levels (MMP-1, MMP-3, MMP-13) are measured, which are expected to be elevated during the inflammatory phase, using specific ELISAs or RNAse protection assays. The granulomas are evaluated by weight, histology and vascular index (mg of carmine dye/g of dry tissue), as a measure of the extent of angiogenesis (Jackson, J. R., et al., 1998. J Pharmacol Exp Ther 284:687–92; Kimura, M., et al., 1985. J Pharmacobiodyn 8:393–400; Miller, A. J., et al.,1997. Am J Physiol 272:R857–61). Leukocytes present in exudates are measured using a Coulter counter and differential counting are performed. Immunohistochemistry with antibodies specific for monocyte/macrophages, neutrophils, B and T cells etc. are used to evaluate the types and numbers of infiltrating inflammatory cells. RNA is isolated from the exudate at different time points and analyzed for ESE-1 expression by Northern blot analysis and RT/PCR. Similarly, RNA from the surrounding synovium and vasculature is analyzed for ESE-1 expression. In situ hybridization and immunohistochemistry for ESE-1 is performed on sections of the air pouch at different times to determine the cellular distribution of ESE-1 and to correlate ESE-1 expression with inflammation. Since IL-1β and TNF-α are being induced in this inflammation model, ESE-1 will be induced as well.

EXAMPLE 4B

Inhibition of ESE-1 Function Interferes with Chronic Inflammation

To evaluate the role of ESE-1 in inflammation in vivo ESE-1 function in the air pouch model is interfered with by gene transfer of dominant-negative mutants of ESE-1. Results from these studies provide ample evidence as to the relevance of ESE-1 for inflammation. To determine whether inhibition of ESE-1 function can completely block inflammation in the air pouch model or can inhibit certain aspects of inflammation such as angiogenesis etc., into the air pouch is injected either the adenovirus vector encoding dominant-negative ESE-1 or a retrovirus encoding dominant-negative ESE-1 prior to injection of the inflammatory stimulant or different times after initiation of granuloma formation. In order to evaluate whether gene transfer is efficient in the air pouch model and whether the adenovirus or the retrovirus efficiently infect the majority of cells that express ESE-1 during inflammation, GFP expressing adenoviral and retroviral vectors are first used. This enables us to determine the most efficient viral titer for gene transfer. Adenoviruses and retroviruses differ in their cell type specificity and efficiency of infection of different cell types. Whereas adenovirus can infect replicating and non-replicating cells, retrovirus is limited to replicating cells. However, adenovirus can infect only cells that express the CAR receptor on their surface which includes mesenchymal cells, vascular smooth muscle and endothelial cells, and epithelial cells, but not all hematopoietic cells (Barr, E., et al., 1994. Gene Ther 1:51–58; Fujita, A., et al., 1995. J Virol 69:6180–6190; Haddada, H., et al., 1993. Biochem Biophys Res Commun 195:1174–83; Setoguchi, Y., et al., 1994. J Invest Dermatol 102:415–421). Retroviruses are very efficiently infecting hematopoietic cells. We, thus, might be able to target specific cellular components of the inflammatory response and test the effect of inhibiting ESE-1 in one cellular component on inflammation.

We have already generated the adenovirus for dominant-negative ESE-1. Another alternative is lentivirus vectors. Dominant-negative ESE-1 is expected to compete with endogenous wild type ESE-1 and to inhibit activity of endogenous ESE-1. The expression level of dominant-negative ESE-1 is evaluated by Western blotting and RT/PCR. The effect of blocking ESE-1 is compared to the effect of empty adeno- and retrovirus vectors in the air pouch model. The same experimental approaches described above are used to assess at various time points throughout the inflammatory lesion granuloma weight, histology, vascular index, cytokine production, upregulation of adhesion molecule expression, stimulation of matrix metalloproteinase expression, increased prostaglandin production, composition of exudates, cellular infiltration, apoptosis etc. Croton oil or murine IL-1β is applied to see if inhibition of ESE-1 will attenuate the polymorphonuclear leukocyte accumulation into air pouches.

RNA is also isolated from various cellular components and expression of various inflammatory response genes using RT/PCR are compared and eventually microarrays.

EXAMPLE 5

ESE-1 Mediates Inhibition of IL-1 of COL2A1 Promote Activity in Chondrocytes Materials The synthetic oligonucleotides that were used for electrophoretic mobility shift assays and site-directed mutagenesis are listed in FIG. 16 and were purchased from Operon Technologies, Inc., Alameda, Calif. The ESE-1 expression plasmids were described previously.

Cell Culture

The immortalized human chondrocyte cell lines T/C-28a2 and C-28/I2 (Goldring M B, et al., J Clin Invest 1994;94:2307–16) were cultured in Dulbecco's modified Eagle's medium (DMEM)/Ham's F12 (1/1, v/v; Life Technologies) containing 10% fetal calf serum (FCS; Biowhitaker) and passaged using trypsin-EDTA solution (Life Technologies) at >95% confluency every 5 to 6 days. The temperature-sensitive tsT/AC62 cells (Robbins J R, et al., Arthritis Rheum 2000;43:2189–201) were grown in DMEM/Ham's F12 (1/1, v/v) supplemented with 10% FCS, 10 IU/ml penicillin, 100 µg/ml streptomycin and maintained at 32° C. in 5% $CO_2$ and the culture medium was changed every 3 to 4 days. The cells were grown to confluence and passaged by treatment with trypsin/EDTA as described previously (Robbins J R, et al., Arthritis Rheum 2000;43:2189–201). Suspensions of tsT/AC62 were embedded in alginate and cultured for X days. For experiments, confluent monolayer cultures or alginate cultures were changed to medium containing 1% Nutridoma-SP (Boehringer-Mannheim) for 24 h prior to incubation in the absence or presence of IL-1β at 200 pg/ml (or TNF-α at 5 ng/ml for the times indicated. Cells in alginate were released by depolymerization of the alginate as described previously (Robbins J R, et al., Arthritis Rheum 2000;43:2189–201).

RNA Extraction and Analysis.

Total RNA was isolated by a one-step extraction procedure using the TRIzol reagent (GIBCO-Life Technologies) and 0.9 µg was reversed transcribed in 20 µl containing Moloney murine leukemia virus RT (2.4 IU/µl), oligo $(dT)_{16}$ (2.5 µM), and RNasin Ribonuclease Inhibitor (1 U/ml; Promega), as described previously (Robbins J R. et al. Immortalized human adult articular chondrocytes maintain cartilage-specific phenotype and responses to interleukin-1 b. Arthritis Rheum 2000;43:2189–201). The primers for human ESE-1 were 5'-CTGAGCAAAGAGTACTGGGACTGTC-3' (SEQ ID NO: 22)(sense) and 5'-CCATAGTTGGGCCACAGCCTCGGAGC-3' (SEQ ID NO: 23)antisense) with an expected amplification product of 188 bp (Oettgen P, et al., Mol Cell Biol 1997;17:4419–33). The primers for COL2AJ and GAPDH were as described previously (Robbins J R, et al., Arthritis Rheum 2000;43:2189–201). POR amplification (35 cycles) was performed using 5 µl of the RT product in a final volume of 50 µl containing 1 mM $MgCl_2$, 200 µM dNTPs, 0.2 µM of each sense and antisense primer, and 2.5 U of Taq DNA polymerase (Promega) using a Perkin Elmer Gene Amp PCR System 9600. Following an initial denaturation at 95° C. for 2 min, amplification was performed at 95° C. for 30 sec and 70° C. for 1 min for 35 cycles, with a final extension at 72° C. for 7 min (Oettgen P, et al., J Biol Chem 1999;274:29439–52). The PCR products, 30 µl of PCR reaction per well, were separated on 1.5% agarose gels.

Electrophoretic Mobility Shift Assays (EMSA) and Supershift Analysis

For preparation of nuclear extracts, T/C-28a2 or C-28/I2 cells were passaged and grown to confluence, changed to medium containing 1% Nutridoma-SP overnight, and treated with IL-1β for the times indicated. The cells were lysed in hypotonic buffer with Nonidet P-40 at a final concentration of 0.5%, as described (McCaffrey P G, J Biol Chem 1992;267:1864–71). Nuclear proteins were extracted in buffer C according to the modified method of Dignam et al. (Dignam J D, et al., Nucleic Acids Res 1983;1 1: 1475–89), dialyzed against low salt buffer D, and used for analysis of binding to DNA. Double-stranded DNA oligonucleotide probes (FIG. 16) were end-labeled using T4 polynucleotide kinase and ($\alpha$-$^{32}$P)dATP. Binding reactions were carried out for 30 min at room temperature using 5 µg of nuclear extract and 0.8 pmol (~10,000 cpm) of labeled probe in a final volume of 20 µl containing 12 mM HEPES-KOH (pH 7.9), 0.94 mM EDTA, 7 mM $MgSO_4$, 100 mM KCl, 0.85 mM DTT, 12.5% glycerol, 0.5 mg/ml bovine serum albumin (BSA), and 1.25 µg poly(dI-dC). The protein-DNA complexes were separated in low ionic strength 4% polyacrylamide gels using Tris/glycine-EDTA buffer (25 mM Tris-HCl, pH 8.5, 190 mM glycine, and 1 mM EDTA), and autoradiographed. The wild-type COL2A1 promoter and mutant oligonucleotides containing putative ETS binding sites, listed in FIG. 16, were used at 50-fold excess in competition EMSAs. For supershift analysis, antibodies were incubated with the binding reaction mixture for 30 min at room temperature before electrophoresis. The consensus and mutant ESE-1 oligonucleotides were used both as labeled probes and as unlabeled competitors in EMSAs.

Plasmid Constructions and Mutagenesis

The COL2A1 sequence spanning −577 to +3428 bp (Goldring M B, et al, J Cell Biochem 1994;54:85–99, 39) was cloned into the pGL2-basic (pGL2B) luciferase reporter gene vector (Promega,) and named pGL2-COL2/4.0. Deletion constructs containing −577/+125 bp, −131/+125 bp, −87/+125 bp were prepared by enzyme digestion of pGL2-COL2/4.0 using PstI, ApaI, and PuuII, followed by ligation. For the deletion constructs −45/+125 bp, −83/+7 bp, and −45/+7 bp, PCR products were generated as described (Osaki et al.) and cloned into the pGL2-Basic luciferase vector. These reporter constructs were used as templates to generate point mutations or internal deletions by PCR mutagenesis employing the oligonucleotides listed in FIG. 16 and the QuikChange™ Site-Directed Mutagenesis Kit (Stratagene, La Jolla, Calif.). DNA fragments containing point mutations were then cloned into the pGL2B vector and confirmed by DNA sequencing using a G2 primer on pGL2 DNA. Deletions were also made in the −577/+127 bp COL2A1 promoter construct using the ExSite™ PCR-Based Site-Directed Mutagenesis Kit (Stratagene).

To generate recombinant proteins for analysis of binding to specific DNA sequences by EMSA, the full-length and dominant-negative mutant ESE-1 cDNAs were inserted into the pCI (Promega) eukaryotic expression vector downstream of the CMV promoter as described (Oettgen P, et al., Mol Cell Biol 1997;17:4419–33). Proteins were produced by in vitro translation using the TNT Quick Coupled Transcription/Translation System (Promega). The sequences of all constructs were confirmed by DNA sequencing performed at the Beth Israel Deaconess Medical Center DNA sequencing facility using the ABI Prism BigDye™ Primer Cycle Sequencing Kit (Applied Biosystems) and the Automatic DNA Sequencer Model 373A (Applied Biosystems).

Transient Transfection and Luciferase Assays

Transient transfection experiments were carried out in C-28/I2 cells using LipofectAMINE PLUS™ Reagent (Life Technologies). Cells were seeded in 6-well tissue culture plates at $3.5 \times 10^5$ cells/well in DMEM/F12 containing 10% FCS 24 h prior to transfection. For each well, 1 µg of COL2A1-luciferase construct, 6 µl of PLUS reagent and 92 µl of serum-free DMEM/F12 were mixed and incubated for 15 min at room temperature. LipofectAMINE+ reagent (4 µl) in 100 µl of serum-free medium was then added to each reaction mixture and incubation was continued for an additional 30 min at room temperature. Finally, the transfection mixture was combined with 800 µl of serum-free medium and the lipid-nucleic acid complex was transferred to the washed cell monolayer in each well. After incubation for 4 h at 37° C., the transfection mix was diluted with an equal volume of DMEM/F12 containing 2% Nutridoma-SP, and incubation continued for 18 h in the absence or presence of IL-1β. For cotransfections, the cells were incubated for 24 h to permit expression of recombinant proteins prior to treatment with IL-1β for a further 18 h. Cell lysates were prepared by extraction with 200 µl of Reporter Lysis Buffer (Promega) and the protein content was determined using the Coomassie Plus Protein Assay Reagent (PIERCE). Luciferase activities were determined by chemiluminescence assay using the Autolumat LB953 luminometer (EG&G Berthold, Oak Ridge, Tenn.), normalized to the amount of protein. Each data point was calculated as the mean±standard deviation for three independently transfected cultures from one representative of at least three experiments.

Adenoviral Infection

Adenoviral infections were performed 18 h after lipofection of the reporter construct and incubation in medium containing 10% FCS. Transduction with adenovirus was performed for 90 min. using a multiple of infection of 1:125 in a 1-ml volume of serum-free medium per well in 6-well plates. After infection the cells were incubated for 18 hours in medium containing 10% FCS. The cultures were then changed to medium containing 1% Nutridoma, incubated for 1 h, and treated with 200 pg/ml IL-1β for 18 h. The IκBα adenovirus was kindly provided by Fionula Brennan (Foxwell B, et al., Proc Natl Acad Sci U S A 1998;95:8211–5).

EXAMPLE 5A

ESE-1 is Inducible by IL-1β in Human Chondrocytes

We first examined the time course of ESE-1 expression at the mRNA level in the C-28/I2 human chondrocyte cell line after treatment with IL-1β for periods of time between 0.5 and 24 h (FIG. 17). In IL-1β-treated quiescent cultures, ESE-1 mRNA was detected at 30 min, increased to peak levels within 4 h, and declined gradually thereafter. Incubation with cycloheximide stabilized the levels of ESE-1 mRNA and augmented control and IL-1β-stimulated expression at least up through 8 h. IL-1 also induced mRNAs encoding two other members of the ESE family, ESE-2 and ESE-3, with peak induction by 4 h and stabilization by cycloheximide. Constitutive levels of COL2A1 mRNA increased with time throughout the 24 h time course. COL2A1 mRNA levels were strongly inhibited by IL-1β by 2 h. Cycloheximide appeared to abolish this inhibition at the earlier time points, although it had no effect by 24 h in either the absence or the presence of IL-1β, as we had found previously (Goldring M B, et al., J Cell Biochem 1994;54:85–99, Goldring M B, et al., J Clin Invest 1994;94:2307–1). A survey of mRNAs for IL-1β inducible genes showed that COX-2 and MMP-1, 3 and 13 mRNAs were increased in treated C-28/I2 cells.

To determine the role of chondrocyte differentiation on the expression of ESE-1, the immortalized human articular chondrocyte cell line, tsT/AC62 (Robbins J R, et al., Arthritis Rheum 2000;43:2189–201), was examined in monolayer and alginate cultures. Chondrocytes are known to dedifferentiate in proliferating monolayer cultures, while culture in alginate has been shown to restore the differentiated phenotype (Hauselmann H J, et al., J Cell Science 1994; 107:17–27). The temperature-sensitive tsT/AC62 cells grown in monolayer were induced by IL-1β to express ESE-1 at both the permissive (32° C.) and nonpermissive (39° C.) temperatures for proliferation (data not shown). However, ESE-1 mRNA was not present in cells in alginate culture in either the absence or presence of IL-1β. The mRNA encoding NERF, another ETS factor, was also not expressed in alginate cultures, but it was present in monolayer cultures at similar levels in both untreated and IL-1β-treated cells (data not shown). An extensive analysis of mRNAs encoding several ETS factors revealed no consistent pattern similar to ESE-1 in response to IL-1β.

EXAMPLE 5B

Figure 18A:
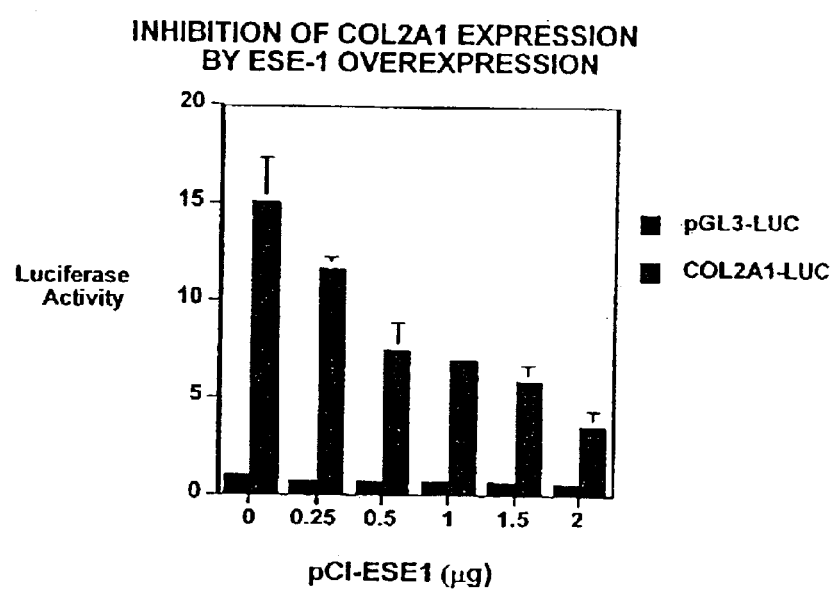
Figure 18B:
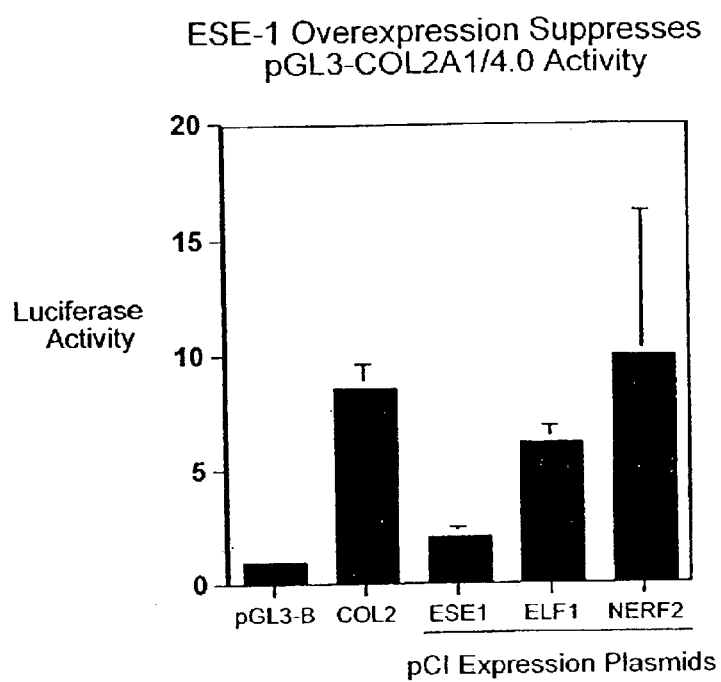

ESE-1, but not ELF-1 or NERF-2, Decreases COL2A1 Promoter Activity in Cotransfection Assays As described above, we observed induction of ESE-1 mRNA preceding the inhibition of COL2A1 mRNA by IL-1β. To determine whether the COL2A1 5'-flanking regulatory region could be a direct target for ESE-1, we performed cotransfection experiments. The T/C-28a2 cells were cotransfected with a luciferase reporter construct containing the COL2A1 promoter and first intron regions spanning −577 bp to +3426 bp. Expression of COL2A1/4.0 was approximately 10- to 15-fold higher than that of the pGL3-basic vector used to make the construct (FIG. 18). Cotransfection of the expression vector, pCI-ESE1, produced a dose-dependent inhibition of COL2A1/4.0 activity, which was 20% (FIG. 18A). Cotransfection expression vectors for two other ETS factors, pCI-ELF1 or pCI-NERF2, produced only 65 and 40% inhibition, respectively, compared to pCI-ESE1 at the highest concentrations tested (FIG. 18B). These results indicate that the COL2A1 gene is a target for transcriptional repression by ESE-1.

We had determined previously that the COL2A1 region spanning −577 to +3426 bp was responsive to IL-1β in both primary and immortalized human chondrocytes when either CAT (Goldring M B, et al., J Cell Biochem 1994;54:85–99, Goldring M B, et al., J Clin Invest 1994;94:2307–1) or luciferase (Robbins J R, et al., Arthritis Rheum 2000;43:2189–201) reporter constructs were used. However, control experiments showed that the pGL3-basic vector appeared to respond directly to IL-1β by increasing activity. Thus, the COL2A1 regulatory sequences were transferred to the pGL2-basic vector for use in all subsequent experiments.

ESE-3 was also found to inhibit COL2A1/4.0 activity, but less effectively than ESE-1. Cotransfection with pCI-ESE 1 produced dose-dependent inhibition of pGL2-COL2/4.0 similar to that observed on the pGL3 construct used in the experiment shown in FIGS. 18A and B. Overexpression of ESE-3 also produce dose-dependent inhibition, but to a lesser extent than pCI-ESE 1, that was ~60% at the highest concentration tested. These results indicate that ESE-3, which is induced by IL-1β and interacts with the same binding sites as ESE-1, can also target the COL2A1 gene.

EXAMPLE 5 C

The Inhibitory Responses to IL-1β and ESE-1 Colocalize in the COL2A1 Promoter Region To determine the regions responsive to IL-1β and ESE-1, pGL2-COL2constructs containing various portions of the promoter and first intron were compared in transient transfections in C-28/I2 cells. A representative experiment is shown in FIG. 19. The pGL2P+2370/+2672, containing the SV40 promoter and chondrocyte-specific COL2A1 enhancer region with binding sites for SOX proteins, expressed at a very low level but still exhibited an inhibitory response to IL-1β. The pGL2B-28/+2122 construct, encompassing the minimal promoter with the TATA box but with the enhancer region deleted also expressed at a low level but responded to IL-1β. Both constructs, however, increased expression ~10-fold in response to pCI-ESE1 overexpression. These results suggest that the ESE-1 response in COL2/4.0 may be mediated by sites in the promoter region.

To localize the responses to IL-1β and ESE-1 in the COL2A1 promoter, we made several 5'-deletions of the −577/+127 bp promoter construct, which we had previously determined to be responsive to IL-1β. As shown in FIG. 19, all five promoter constructs responded to IL-1β showing at least 50% inhibition. The activities of the constructs, −577/+127 bp, −530/+127 bp, and −403/+127 bp, were also inhibited in a dose-dependent manner by pCI-ESE overexpression. Cotransfection with the highest amount of pCI-ESE1 used, 200 ng, produced levels of inhibition similar to IL-1β. In contrast, the −131/+127 bp, −83/+127 bp constructs did not respond to pCI-ESE1 either positively or negatively. We showed previously that inhibition by IL-1β of the −131 bp promoter region is mediated via a binding site for Egr-1 (Tan et al., submitted). These results indicate that the COL2A1promoter region spanning −403 to −131 bp contains elements that respond to both IL-1β and ESE-1.

EXAMPLE 5D

EMSA Analysis of ESE-1 Binding to the COL2A1 Promoter

Computer analysis of the COL2A1 promoter sequence identified 4 potential binding sites for ESE-1 at positions at the positions listed in FIG. 16. In initial screens, recombinant ESE-1 or a nuclear factor from IL-1β-treated cells formed complexes with the labeled sequences, X, Y, Z, which corresponded in mobility and time course of induction with ESE-1 binding to the ESE-1 consensus.

The invention has been described in detail with particular references to the preferred embodiments thereof. However, it will be appreciated that modifications and improvements within the spirit and scope of this invention may be made by those skilled in the art upon considering the present disclosure.

The references cited herein are incorporated by reference.

We claim:

1. A method of screening compounds that are capable of reducing inflammation comprising:
   (a) providing cells which do not normally express a measurable amount of a transcription factor except in the presence of a pro-inflammatory agent;
   (b) providing two portions of said cells to form a control and exoerimental group of cells;
   c) providing the experimental group of cells with said compound;
   (d) providing the pro-inflammatory agent to both the control and experimental group of cells;
   (e) measuring the expression of the transcription factor in both the control and the experimental group of cells; and
   (f) comparing the amount of expression of said transcription factor in the experimental group of cells with the control group of cells,
   wherein decreased expression of said transcription factor in the experimental group of cells when compared to the control group of cells indicates that the compound may be capable of reducing inflammation in vivo.

2. The method according to claim 1, wherein the transcription factor comprises a STAT transcription factor, C/EBPs, HMG protein, EGR-1 or AP-1.

3. The method according to claim 1, wherein the transcription factor comprises an Ets transcription factor.

4. The method according to claim 3, wherein the Ets transcription factor comprises ESE-1 or ESE-1 related factors, e.g., ESE-2 and ESE-3.

5. The method according to claim 3, wherein the Ets transcription factor comprises Ets-1, Ets-2, ERG, SAP-1, ELK-1, Erp-1, TEL-1, TEL-2, PU.1 and FLI-1.

6. The method according to claim 1, wherein the compound comprises a small molecule, peptide, antisense RNA or viral DNA.

7. The method according to claim 1, wherein the inflammatory agent comprises a pro-inflammatory cytokine, endotoxin or a virus.

8. The method according to claim 7, wherein the pro-inflammatory cytokine comprises IL-1, IL-1β, TNF-α, and IL-15, IL-17, IL-18, oncostatin M, and leukemia inhibitory factor.

9. The method according to claim 1, wherein the cells comprises fibroblasts, synoviocytes, chondrocytes, murine monocytes, glioma cells, osteoblasts, smooth muscle cells, endothelial cells, or monocytic cells.

10. The method according to claim 9, wherein the smooth muscle cells comprises vascular smooth muscle cells.

11. The method according to claim 7, wherein the endotoxin comprises LPS.

* * * * *